United States Patent
Adams et al.

(10) Patent No.: US 9,957,254 B2
(45) Date of Patent: May 1, 2018

(54) CYCLOHEXEN-1-YL-PYRIDIN-2-YL-1H-PYRAZOLE-4-CARBOXYLIC ACID DERIVATIVES AND THE USE THEREOF AS SOLUBLE GUANYLATE CYCLASE ACTIVATORS

(71) Applicants: Christopher M. Adams, Arlington, MA (US); David B. Belanger, Lexington, MA (US); Doug Bevan, Chelmsford, MA (US); Philippe Bolduc, Cambridge, MA (US); Takeru Ehara, Arlington, MA (US); Luciana Ferrara, Stoughton, MA (US); Nan Ji, Arlington, MA (US); Mitsunori Kato, Cambridge, MA (US); Erik Meredith, Hudson, MA (US); Muneto Mogi, Waltham, MA (US); James J. Powers, Waltham, MA (US); Ganesh Prasanna, Acton, MA (US)

(72) Inventors: Christopher M. Adams, Arlington, MA (US); David B. Belanger, Lexington, MA (US); Doug Bevan, Chelmsford, MA (US); Philippe Bolduc, Cambridge, MA (US); Takeru Ehara, Arlington, MA (US); Luciana Ferrara, Stoughton, MA (US); Nan Ji, Arlington, MA (US); Mitsunori Kato, Cambridge, MA (US); Erik Meredith, Hudson, MA (US); Muneto Mogi, Waltham, MA (US); James J. Powers, Waltham, MA (US); Ganesh Prasanna, Acton, MA (US)

(73) Assignee: Novartis AG, Basel (CH)

( * ) Notice: Subject to any disclaimer, the term of this patent is extended or adjusted under 35 U.S.C. 154(b) by 0 days. days.

(21) Appl. No.: 15/320,815

(22) PCT Filed: Jul. 2, 2015

(86) PCT No.: PCT/IB2015/055009
§ 371 (c)(1),
(2) Date: Dec. 21, 2016

(87) PCT Pub. No.: WO2016/001878
PCT Pub. Date: Jan. 7, 2016

(65) Prior Publication Data
US 2017/0197941 A1    Jul. 13, 2017

Related U.S. Application Data

(60) Provisional application No. 62/020,187, filed on Jul. 2, 2014, provisional application No. 62/127,535, filed on Mar. 3, 2015, provisional application No. 62/168,651, filed on May 29, 2015.

(51) Int. Cl.
C07D 401/14    (2006.01)
C07D 401/04    (2006.01)

(52) U.S. Cl.
CPC ......... *C07D 401/14* (2013.01); *C07D 401/04* (2013.01)

(58) Field of Classification Search
CPC .................................................. C07D 401/14
See application file for complete search history.

(56) References Cited

U.S. PATENT DOCUMENTS

| 6,335,334 B1 | 1/2002 | Schindler et al. | |
| 2009/0209556 A1* | 8/2009 | Bittner | C07D 401/04 514/255.05 |

(Continued)

FOREIGN PATENT DOCUMENTS

| EP | 1420023 A1 | 5/2004 |
| WO | 02070462 A1 | 9/2002 |
| WO | 02070510 A2 | 9/2002 |

(Continued)

OTHER PUBLICATIONS

Glaucome [online], retrieved from the internet on May 29, 2017; URL: http://www.mayoclinic.org/diseases-conditions/glaucoma/basics/deinition/con-20024042?.*

(Continued)

*Primary Examiner* — Shawquia Jackson
(74) *Attorney, Agent, or Firm* — Shawn D. Britt

(57) ABSTRACT

The present invention provides a compound of formula (I) or a pharmaceutically acceptable salt thereof; a method for manufacturing the compounds of the invention, and its therapeutic uses. The present invention further provides a combination of pharmacologically active agents and a pharmaceutical composition.

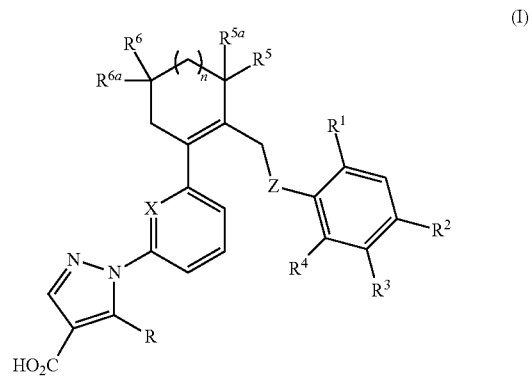

(I)

17 Claims, No Drawings

(56) References Cited

U.S. PATENT DOCUMENTS

2010/0216764 A1 8/2010 Kim et al.
2011/0028493 A1 2/2011 Matsunaga et al.

FOREIGN PATENT DOCUMENTS

| WO | 03086407 A1 | 10/2003 |
|---|---|---|
| WO | 2008073452 A1 | 6/2008 |
| WO | 08119458 A1 | 10/2008 |
| WO | 2009032249 A1 | 3/2009 |
| WO | 2009068652 A1 | 6/2009 |
| WO | 2009071504 A1 | 6/2009 |
| WO | 09127338 A1 | 10/2009 |
| WO | 10102717 A1 | 9/2010 |
| WO | 2010099054 A2 | 9/2010 |
| WO | 2011051165 A1 | 5/2011 |
| WO | 2012058132 A1 | 5/2012 |
| WO | 2012076466 A2 | 6/2012 |
| WO | 2012122340 A1 | 9/2012 |
| WO | 2012139888 A1 | 10/2012 |
| WO | 13025425 A1 | 2/2013 |
| WO | 201457740 A1 | 10/2014 |
| WO | 2015011086 A1 | 1/2015 |
| WO | 2015033307 A1 | 3/2015 |

OTHER PUBLICATIONS

Shie, et al., "Puring derivatives as potent Bruton's tyrosine kinase (BTK) inhibitors for autoimmune diseases", Bioorganic & Medicinal Cemistry Letters, 24(9):2212-2221 (2014).

Abdel-Rahman, et al., "Synthesis of Novel Fluorine Substituted isolated and Fused Heterobicyckic Nitrogen Systems Bearing 6-(2'-Phosphorylanilido)-1,2,4-Triazin-5-One Moiety as Potential Inhibitor towards HIV-1 Activity", International Journal of Organic Chemistry, 4(4):247-268 (2014).

Stasch, et al., "Renal effects of soluble guanylate cyclase stimulators and activators: A review of the preclinical evidence", Current Opinion in Pharmacology, 21:95-104 (2015).

Bucolo, Claudio et al. "Pharmacological management of ocular hypertension: current approaches and futre prospective." Pharmacology. SciVerse Science Direct. 2012, 13, pp. 1-6.

Toris, Carol B. et al. "Aqueous dynamics, IOP, blood flow, clinical studies." ARVO 2015 Annual Meeting Abstracts. May 6, 2015, Exhibit Hall Poster Session. 10 pages.

Drug Label for ADEMPAS. Oct. 8, 2013. NDA 204819. 28 pages.

* cited by examiner

CYCLOHEXEN-1-YL-PYRIDIN-2-YL-1H-PYRAZOLE-4-CARBOXYLIC ACID DERIVATIVES AND THE USE THEREOF AS SOLUBLE GUANYLATE CYCLASE ACTIVATORS

This application is a U.S. National Phase filing of International Application No. PCT/IB2015/055009 filed 2 Jul. 2015, which claims priority to U.S. Application No. 62/020,187 filed 2 Jul. 2014, also claims priority to U.S. Application No. 62/127,535, filed Mar. 3, 2015, and also claims priority to U.S. Application No. 62/168,651, Filed May 29, 30216, the content of all of which are incorporated herein by reference in their entireties.

FIELD OF THE INVENTION

The present invention is related generally to compounds which activate soluble guanylate cyclase (sGC). The invention further relates to the use of said sGC activators in the treatment of glaucoma and in the lowering intraocular pressure such as that associated with glaucoma and ocular hypertension.

BACKGROUND OF THE INVENTION

The eye disease glaucoma is characterized by a permanent loss of visual function due to irreversible damage to the optic nerve. The several morphologically or functionally distinct types of glaucoma are typically characterized by an undesirable elevation of intraocular pressure (IOP), which is considered to be causally related to the pathological course of the disease. Continuously elevated IOP has been associated with the progressive loss of retinal ganglion cells, optic nerve damage ultimately resulting in the loss of visual function. In some cases, ocular hypertension, a condition in which IOP is elevated, can present without apparent loss of visual function. However, patients with ocular hypertension are considered to be at a high risk for eventually developing the visual loss associated with glaucoma. Therefore, lowering IOP is the current treatment objective for the of glaucoma patients and for patients with ocular hypertension in order to decrease the potential for, or severity of, glaucomatous retinopathy. Unfortunately, many individuals do not respond well when treated with existing glaucoma therapies.

Patients known as normotensive or low-tension glaucoma patients have relatively low IOP, yet present with glaucomatous visual field loss. These patients may benefit from agents that lower and control IOP, because glaucoma that is detected early and treated promptly may have reduced or delayed loss of visual function. Conventional therapeutic agents that have proven to be effective for the reduction of IOP include both agents that decrease aqueous humor production and agents that increase the outflow facility. Such agents are in general administered by one of two routes; topically by direct application to the eye, or orally. However, many of these agents have associated side effects which may render them undesirable as ocular therapeutic agents.

Soluble guanylate cyclase (sGC) is a receptor enzyme for the second messenger, nitric oxide (NO), in several cell types including muscle, epithelia, neuronal, and endothelial cells. In humans, functional sGC is a heterodimer composed of either an alpha 1 or alpha 2 subunit combined with the beta 1 subunit which has a heme prosthetic group. Under physiological conditions, NO binds to the prosthetic heme of sGC which activates the enzyme to catalyze the conversion of guanosine-5'-triphosphate (GTP) to cyclic guanosine monophosphate (cGMP). cGMP is a second messenger which in turn exerts its effects by activating cGMP dependent protein kinase (PKG) isoforms, phosphodiesterases, and cGMP gated ion channels. In doing so, sGC can thus modulate numerous pathways associated with diseases including hypertension (arterial and pulmonary), heart failure, atherosclerosis, erectile dysfunction, liver cirrhosis, and renal fibrosis. Under aforementioned pathologic conditions prolonged oxidative stress can cause the oxidation of the heme group of sGC (from ferrous to ferric state) which is incapable of being activated by NO and can contribute to exacerbation of disease processes. As a consequence of sGC oxidation and unresponsiveness to NO, endothelial dysfunction, atherosclerosis, hypertension, stable or unstable angina pectoris, thromboses, myocardial infarction, strokes or erectile dysfunction are worsened. Therefore, pharmacological stimulation or activation of sGC offers a possibility to normalize cGMP production and therefore makes possible the treatment and/or prevention of such disorders.

To this effort, there are two classes of compounds have been identified, including NO-independent/reduced heme-dependent sGC stimulators and NO-independent/heme-independent sGC activators. sGC stimulators are dependent on heme, but they are not active once sGC become oxidized. sGC activators on the other hand can still activate the enzyme to generate cGMP even in the absence of nitric oxide (NO) and/or under oxidative stress induced oxidation of sGC in disease tissue. Thus, the activity of sGC in these situations will be corrected by sGC activators, but not by sGC stimulators, and will have the potential to provide benefit in many diseases caused by defective signaling in the NO pathway especially following oxidative stress.

SUMMARY OF THE INVENTION

The present invention in part relates to new activators of sGC and the use thereof in the treatment of disease. In one aspect the sGC activators provided herein are suitable for use in methods of treating glaucoma in human patients or other mammals. The present invention also relates to methods of lowering or controlling normal or elevated IOP in a human patient or other mammals. In particular, the invention provides methods of treating and/or preventing glaucoma by administration of a sGC activator compound described infra.

In the eye, the trabecular outflow pathway by which 70-80% of aqueous humor would normally leave the anterior chamber of the eye and lower intraocular pressure (IOP), is pathologically compromised in primary open angle glaucoma (POAG). Oxidative stress is thought to be an underlying factor that can adversely affect trabecular meshwork function, resulting from/in IOP elevation in POAG. Reactive oxygen species (ROS) not only decrease the bioavailability of nitric oxide (NO) but also shift the sGC redox equilibrium to its oxidized form, which as mentioned before is unresponsive to NO. Selective activation of the oxidized form of sGC should target only the diseased state of the target enzyme in the putative target tissue, trabecular meshwork/Schlemm's canal tissue, thus offering a highly innovative therapy for glaucoma that should work adjunctively with current therapies.

In one aspect of the invention, sGC activators, and salts thereof, are provided which have the structure of formula (I):

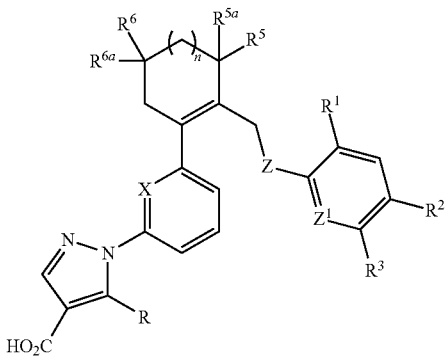

Wherein the variables are defined infra.

Certain embodiments of the present invention comprise compositions or methods which include or use compounds capable of activating sGC thereby modulating intraocular pressure in the eye. By activating sGC receptor activity, subject compounds according to certain embodiments of the present invention are accordingly useful for lowering and/or controlling IOP associated with normal-tension glaucoma, ocular hypertension, and glaucoma, including primary open-angle glaucoma in humans and other warm-blooded animals. When used in such applications, the compounds may be formulated in pharmaceutical compositions suitable for topical delivery to the eye.

The foregoing brief summary broadly describes the features and technical advantages of certain embodiments of the present invention. Additional features and technical advantages will be described in the detailed description of the invention that follows.

DESCRIPTION OF THE INVENTION

As the term is used herein, a "sGC activator" is a compound capable of modulating sGC activity to generate cGMP signaling which would otherwise be unresponsive to nitric oxide. In contrast, "sGC stimulators" refers to compounds that are capable of synergizing with nitric oxide and can directly stimulate cGMP production so long as the reduced heme domain is present in the enzyme.

In a first embodiment, the invention provides a compound according to Formula (I)

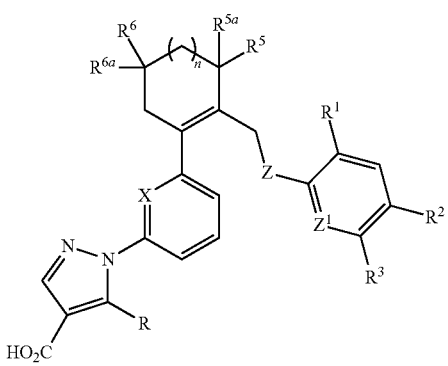

Or a pharmaceutically acceptable salt thereof, wherein
n is 0 or 1;
X is N or CH;
Z is N(H), O or $CH_2$;
$Z^1$ is $CR^4$ or N;
R is hydrogen, $C_1$-$C_4$alkyl, monofluoromethyl, difluoromethyl or trifluoromethyl;
$R^1$ is hydrogen, halogen, $C_1$-$C_4$alkyl or trifluoromethyl
$R^2$ is piperidinyl which is N-substituted with $C_1$-$C_4$alkyl, $C_3$-$C_6$cycloalkyl, halo$C_1$-$C_4$alkyl, C(O)$C_1$-$C_4$alkyl, S(O)$_2$$C_1$-$C_4$alkyl, C(O)$C_3$-$C_6$cycloalkyl, C(O)halo$C_1$-$C_4$alkyl, C(O)$C_1$-$C_4$alkoxy, C(O)$C_1$-$C_4$alkenoxy, heteroaryl or CO(O)$_2$benzyl, wherein each cycloalkyl is optionally substituted by hydroxy and each alkyl or alkoxy is optionally substituted by hydroxyl, $C_1$-$C_4$alkoxy or $C_3$-$C_6$cycloalkyl and wherein each heteroaryl has 5 or 6 ring atoms, 1, 2 or 3 ring heteroatoms independently selected from N, O and S and is optionally substituted with 1 or 2 $C_1$-$C_4$alkyl substituents, which piperidinyl ring is further optionally substituted by hydroxyl;
$R^3$ is hydrogen, halogen or $C_1$-$C_4$alkyl; or
$R^2$ and $R^3$, taken in combination, form a 5 or 6 member fused saturated azacyclic ring optionally substituted with benzyl or 5 or 6 member heteroarylmethyl, which heteroaryl has 1 or 2 ring heteroatoms independently selected from N, O and S;
$R^4$ is hydrogen or $C_1$-$C_4$alkyl;
$R^5$ and $R^{5a}$ are independently selected from the group consisting of hydrogen and $C_1$-$C_4$alkyl; or
$R^5$ and $R^{5a}$, taken in combination form a spirocyclic cyclopropyl ring; and
when n is 0, $R^6$ and $R^{6a}$ are each hydrogen and when n is 1, $R^6$ and $R^{6a}$ are independently selected from the group consisting of hydrogen and $C_1$-$C_4$alkyl; or
$R^6$ and $R^{6a}$, taken in combination form a spirocyclic cyclopropyl ring.

Certain compounds of the first embodiment, include compounds of the formula:

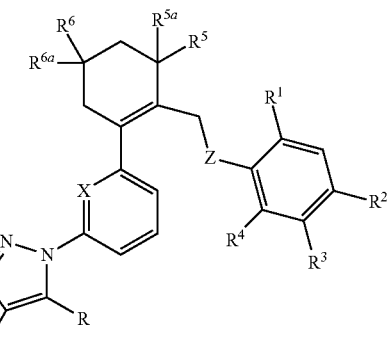

Or a pharmaceutically acceptable salt thereof, wherein
X is N or CH;
Z is O or $CH_2$;
R is $C_1$-$C_4$alkyl or trifluoromethyl;
$R^1$ and $R^4$ are each independently selected from hydrogen, halogen or $C_1$-$C_4$alkyl; or $R^4$ is halo$C_1$-$C_4$alkyl;
$R^2$ is piperidinyl which is N-substituted with $C_1$-$C_4$alkyl, halo$C_1$-$C_4$alkyl, $C_3$-$C_6$cycloalkyl, C(O)$C_1$-$C_4$alkyl which is optionally substituted with hydroxyl or amino, C(O)$C_3$-$C_6$cycloalkyl, C(O)$C_1$-$C_4$alkoxy, C(O)NH($C_1$-$C_4$alkyl), C(O)N($C_1$-$C_4$alkyl)$_2$, S(O)$_2$$C_1$-$C_4$alkyl, S(O)$_2$ $C_3$-$C_6$cycloalkyl or C(O)heteroaryl which heteroaryl has 5 or 6 ring atoms and 1 or 2 ring heteroatoms independently selected from the group consisting of N, O and S;

$R^3$ is hydrogen $C_1$-$C_4$alkyl; or $R^2$ and $R^3$, taken in combination form a 6 member fused saturated azacyclic ring optionally substituted with benzyl or 5, 6, 9 or 10 member heteroarylmethyl, which heteroaryl has 1 or 2 rings and 1 or 2 ring heteroatoms independently selected from N, O and S;

$R^5$ and $R^{5a}$ are independently selected from the group consisting of hydrogen and $C_1$-$C_4$alkyl; or $R^5$ and $R^{5a}$, taken in combination form a spirocyclic cyclopropyl ring; and $R^6$ and $R^{6a}$ are independently selected from the group consisting of hydrogen and $C_1$-$C_4$alkyl; or $R^6$ and $R^{6a}$, taken in combination form a spirocyclic cyclopropyl ring. Preferred compounds of embodiment 1 include compounds in which at least 1 and preferably at least 2 of $R^5$, $R^{5a}$, $R^6$ and $R^{6a}$ are hydrogen.

Certain other compounds of the first embodiment include compounds of the formula:

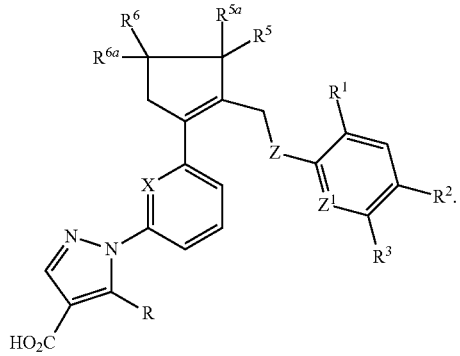

In a second embodiment, compounds of embodiment 1 or a pharmaceutically acceptable salt thereof, are provided in which Z is O.

In a third embodiment, compounds of embodiment 1 or embodiment 2 or a pharmaceutically acceptable salt thereof are provided in which $R^2$ is N-substituted piperidin-4-yl wherein the N-substituent is halo$C_1$-$C_4$alkyl, C(O)cyclopropyl, S(O)$_2$cyclopropyl, S(O)$_2$$C_1$-$C_4$alkyl, C(O)cyclobutyl, C(O)N($C_1$-$C_4$alkyl)$_2$, C(O)$C_1$-$C_4$alkyl, C(O)$C_1$-$C_4$alkoxy or C(O)$C_1$-$C_4$alkyl substituted with hydroxyl or amino.

In a fourth embodiment, compounds of any one of embodiments 1 to 3, or a pharmaceutically acceptable salt thereof, are provided in which $R^2$ is N-substituted piperidin-4-yl wherein the N-substituent is 2,2,2-trifluoroethyl, C(O)cyclopropyl, C(O)(1-hydroxyethyl), S(O)$_2$ethyl, S(O)$_2$cyclopropyl, C(O)ethyl, C(O)iso-propyl, C(O)N(methyl)$_2$ or C(O)N(ethyl)$_2$.

In a fifth embodiment, compounds of any one of embodiments 1 to 4, or a pharmaceutically acceptable salt thereof, are provided in which $R^1$ is methyl and $R^3$ and $R^4$ are hydrogen.

In a sixth embodiment, compounds of any one of embodiments 1 to 4, or a pharmaceutically acceptable salt thereof, are provided in which $R^1$ and $R^4$ are hydrogen; and $R^3$ is ethyl.

In a seventh embodiment, compounds of any one of embodiments 1 to 6, or a pharmaceutically acceptable salt thereof, are provided in which $R^5$, $R^{5a}$, $R^6$ and $R^{6a}$ are independently selected from hydrogen and methyl. In certain preferred compounds of the seventh embodiment, $R^5$ is methyl, $R^{5a}$ is hydrogen or methyl and $R^6$ and $R^{6a}$ are hydrogen. In other preferred compounds of the seventh embodiment $R^5$ and $R^{5a}$ are methyl and $R^6$ and $R^{6a}$ are hydrogen. In yet other preferred compounds of the seventh invention, $R^5$, $R^{5a}$ and $R^{6a}$ are hydrogen and $R^6$ is hydrogen.

In an eighth embodiment, compounds of any one of embodiments 1 to 6, or a pharmaceutically acceptable salt thereof, are provided in which $R^5$ and $R^{5a}$ are methyl, or $R^5$ and $R^{5a}$, taken in combination form a spirocyclic cyclopropyl ring; and $R^6$ and $R^{6a}$ are hydrogen;

In certain other aspects of the invention, compounds of any one of embodiments 1 to 6 are provided in which $R^5$ and $R^{5a}$ are hydrogen, and $R^6$ and $R^{6a}$ are methyl, or $R^6$ and $R^{6a}$, taken in combination form a spirocyclic cyclopropyl ring.

In a ninth embodiment, compounds of any one of embodiments 1 to 8, or a pharmaceutically acceptable salt thereof, are provided in which R is trifluoromethyl, methyl or ethyl.

In a tenth embodiment, compounds of any one of embodiments 1 to 9, or a pharmaceutically acceptable salt thereof, are provided in which R is methyl or ethyl.

In a eleventh embodiment, compounds of any one of embodiments 1 to 9, or a pharmaceutically acceptable salt thereof, are provided in which R is trifluoromethyl.

In a twelfth embodiment, compounds of any one of embodiments 1 to 11, or a pharmaceutically acceptable salt thereof, are provided in which X is N.

In a thirteenth embodiment, compounds of embodiment 1 or a pharmaceutically acceptable salt thereof are provided in which the compound represented by Formula (II):

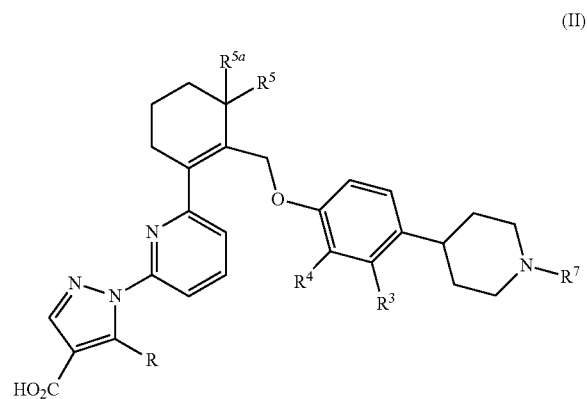

(II)

wherein

R is trifluoromethyl, methyl or ethyl;

$R^3$ is hydrogen or ethyl;

$R^4$ is hydrogen, methyl or ethyl;

$R^5$ and $R^{5a}$ are each independently selected from hydrogen and methyl; and $R^7$ is 2,2,2-trifluoroethyl, C(O)ethyl, C(O)isopropyl, C(O)(hydroxymethyl), C(O)(1-hydroxyethyl), CO$_2$methyl, C(O)cyclopropyl, C(O)cyclobutyl, C(O)N(methyl)$_2$, C(O)N(ethyl)$_2$, S(O)$_2$methyl, S(O)$_2$ethyl, or S(O)$_2$cyclopropyl.

In a fourteenth embodiment, compounds of embodiments 13, or a pharmaceutically acceptable salt thereof, are provided in which $R^7$ 2,2,2-trifluoroethyl, C(O)(1-hydroxyethyl) or C(O)cyclopropyl.

In a fifteenth embodiment, compounds of embodiments 13 or embodiment 14, or a pharmaceutically acceptable salt thereof, are provided in which $R^5$ is methyl and $R^{5a}$ is hydrogen.

In a sixteenth embodiment, compounds of embodiment 1 or a pharmaceutically acceptable salt thereof are provided in which the compound represented by Formula (III):

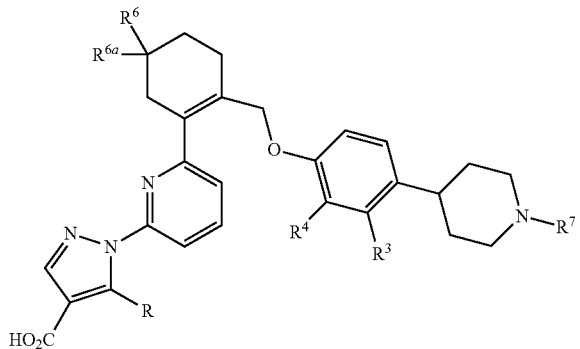

(III)

wherein
R is trifluoromethyl, methyl or ethyl;
$R^3$ is hydrogen or ethyl;
$R^4$ is hydrogen, methyl or ethyl;
$R^6$ and $R^{6a}$ are each independently selected from hydrogen and methyl; and
$R^7$ is 2,2,2-trifluoroethyl, C(O)ethyl, C(O)isopropyl, C(O)(hydroxymethyl), C(O)(1-hydroxyethyl), $CO_2$methyl, C(O)cyclopropyl, C(O)cyclobutyl, C(O)N(methyl)$_2$, C(O)N(ethyl)$_2$, S(O)$_2$methyl, S(O)$_2$ethyl, or S(O)$_2$cyclopropyl.

In a seventeenth embodiment, compounds of embodiment 1 or a pharmaceutically acceptable salt thereof are provided in which the compound represented by Formula (III):

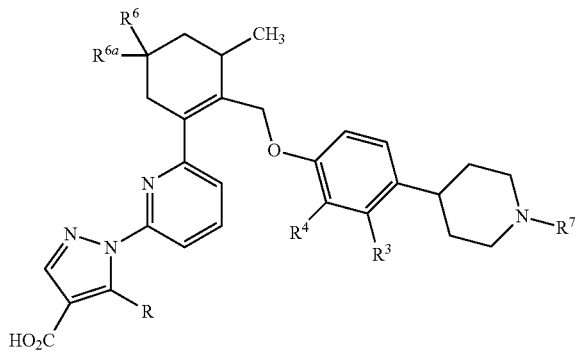

(IV)

wherein
R is trifluoromethyl, methyl or ethyl;
$R^3$ is hydrogen or ethyl;
$R^4$ is hydrogen, methyl or ethyl;
$R^6$ and $R^{6a}$ are each independently selected from hydrogen and methyl; and
$R^7$ is 2,2,2-trifluoroethyl, C(O)ethyl, C(O)isopropyl, C(O)(hydroxymethyl), C(O)(1-hydroxyethyl), $CO_2$methyl, C(O)cyclopropyl, C(O)cyclobutyl, C(O)N(methyl)$_2$, C(O)N(ethyl)$_2$, S(O)$_2$methyl, S(O)$_2$ethyl, or S(O)$_2$cyclopropyl.

In an eighteenth embodiment, compounds of embodiments 16 or 17, or a pharmaceutically acceptable salt thereof, are provided in which $R^7$ 2,2,2-trifluoroethyl, C(O)(1-hydroxyethyl) or C(O)cyclopropyl.

In a nineteenth embodiment, compounds of any one of embodiments 16, 17 or 18, or a pharmaceutically acceptable salt thereof, are provided in which $R^6$ is methyl and $R^{6a}$ is hydrogen.

In another embodiment of the invention, compounds of the first embodiment are provided in which n is 0 and each of $R^5$, $R^{5a}$, $R^6$ and $R^{6a}$ are hydrogen.

In a twentieth embodiment of the invention, compounds of embodiment 1 are provided which are selected from the group consisting of:
1-(6-(2-((4-(1-(cyclopropanecarbonyl)piperidin-4-yl)-2-methylphenoxy)methyl)cyclohex-1-en-1-yl)pyridin-2-yl)-5-(trifluoromethyl)-1H-pyrazole-4-carboxylic acid;
1-(6-(2-((2-methyl-4-(1-propionylpiperidin-4-yl)phenoxy)methyl)cyclohex-1-en-1-yl)pyridin-2-yl)-5-(trifluoromethyl)-1H-pyrazole-4-carboxylic acid;
1-(6-(2-((4-(1-(methoxycarbonyl)piperidin-4-yl)-2-methylphenoxy)methyl)cyclohex-1-en-1-yl)pyridin-2-yl)-5-(trifluoromethyl)-1H-pyrazole-4-carboxylic acid;
1-(6-(2-((2-methyl-4-(1-(methylsulfonyl)piperidin-4-yl)phenoxy)methyl)cyclohex-1-en-1-yl)pyridin-2-yl)-5-(trifluoromethyl)-1H-pyrazole-4-carboxylic acid;
1-(6-(2-((4-(1-(dimethylcarbamoyl)piperidin-4-yl)-2-methylphenoxy)methyl)cyclohex-1-en-1-yl)pyridin-2-yl)-5-(trifluoromethyl)-1H-pyrazole-4-carboxylic acid;
1-(6-(2-((4-(1-(2-hydroxyacetyl)piperidin-4-yl)-2-methylphenoxy)methyl)cyclohex-1-en-1-yl)pyridin-2-yl)-5-(trifluoromethyl)-1H-pyrazole-4-carboxylic acid;
1-(6-(2-((4-(1-(cyclopropanecarbonyl)piperidin-4-yl)phenoxy)methyl)cyclohex-1-en-1-yl)pyridin-2-yl)-5-(trifluoromethyl)-1H-pyrazole-4-carboxylic acid;
1-(6-(2-((4-(1-(diethylcarbamoyl)piperidin-4-yl)-2-methylphenoxy)methyl)cyclohex-1-en-1-yl)pyridin-2-yl)-5-(trifluoromethyl)-1H-pyrazole-4-carboxylic acid;
1-(6-(2-((4-(1-(ethylsulfonyl)piperidin-4-yl)-2-methylphenoxy)methyl)cyclohex-1-en-1-yl)pyridin-2-yl)-5-(trifluoromethyl)-1H-pyrazole-4-carboxylic acid;
1-(6-(2-((4-(1-(cyclopropylsulfonyl)piperidin-4-yl)-2-methylphenoxy)methyl)cyclohex-1-en-1-yl)pyridin-2-yl)-5-(trifluoromethyl)-1H-pyrazole-4-carboxylic acid;
1-(6-(2-((4-(1-isobutyrylpiperidin-4-yl)-2-methylphenoxy)methyl)cyclohex-1-en-1-yl)pyridin-2-yl)-5-(trifluoromethyl)-1H-pyrazole-4-carboxylic acid;
1-(6-(2-((4-(1-(cyclobutanecarbonyl)piperidin-4-yl)-2-methylphenoxy)methyl)cyclohex-1-en-1-yl)pyridin-2-yl)-5-(trifluoromethyl)-1H-pyrazole-4-carboxylic acid;
1-(6-(2-((4-(1-(ethylcarbamoyl)piperidin-4-yl)-2-methylphenoxy)methyl)cyclohex-1-en-1-yl)pyridin-2-yl)-5-(trifluoromethyl)-1H-pyrazole-4-carboxylic acid;
(S)-1-(6-(2-((4-(1-(2-hydroxypropanoyl)piperidin-4-yl)-2-methylphenoxy)methyl)cyclohex-1-en-1-yl)pyridin-2-yl)-5-(trifluoromethyl)-1H-pyrazole-4-carboxylic acid;
(R)-1-(6-(2-((4-(1-(2-hydroxypropanoyl)piperidin-4-yl)-2-methylphenoxy)methyl)cyclohex-1-en-1-yl)pyridin-2-yl)-5-(trifluoromethyl)-1H-pyrazole-4-carboxylic acid;
1-(6-(2-((2-methyl-4-(1-picolinoylpiperidin-4-yl)phenoxy)methyl)cyclohex-1-en-1-yl)pyridin-2-yl)-5-(trifluoromethyl)-1H-pyrazole-4-carboxylic acid;
1-(6-(2-(((2-((6-methylpyridin-2-yl)methyl)-1,2,3,4-tetrahydroisoquinolin-6-yl)oxy)methyl)cyclohex-1-en-1-yl)pyridin-2-yl)-5-(trifluoromethyl)-1H-pyrazole-4-carboxylic acid;
1-(6-(2-((2-methyl-4-(1-(2,2,2-trifluoroethyl)piperidin-4-yl)phenoxy)methyl)cyclohex-1-en-1-yl)pyridin-2-yl)-5-(trifluoromethyl)-1H-pyrazole-4-carboxylic acid;

1-(6-(2-(((2-(quinolin-2-ylmethyl)-1,2,3,4-tetrahydroiso-quinolin-6-yl)oxy)methyl)cyclohex-1-en-1-yl)pyridin-2-yl)-5-(trifluoromethyl)-1H-pyrazole-4-carboxylic acid;

1-(6-(2-((4-(1-(cyclopropanecarbonyl)piperidin-4-yl)-3-ethylphenoxy)methyl)cyclohex-1-en-1-yl)pyridin-2-yl)-5-(trifluoromethyl)-1H-pyrazole-4-carboxylic acid;

1-(6-(2-((4-(1-(cyclopropanecarbonyl)piperidin-4-yl)-2-ethylphenoxy)methyl)cyclohex-1-en-1-yl)pyridin-2-yl)-5-(trifluoromethyl)-1H-pyrazole-4-carboxylic acid;

1-(6-(2-(((2-(pyridin-2-ylmethyl)-1,2,3,4-tetrahydroisoquinolin-6-yl)oxy)methyl)cyclohex-1-en-1-yl)pyridin-2-yl)-5-(trifluoromethyl)-1H-pyrazole-4-carboxylic acid;

1-(6-(2-((4-(1-(cyclopropanecarbonyl)piperidin-4-yl)-2-methylphenoxy)methyl)cyclohex-1-en-1-yl)pyridin-2-yl)-5-ethyl-1H-pyrazole-4-carboxylic acid;

1-(6'-((4-(1-(cyclopropanecarbonyl)piperidin-4-yl)-2-methylphenoxy)methyl)-2',3',4',5-tetrahydro-[1,1'-biphenyl]-3-yl)-5-(trifluoromethyl)-1H-pyrazole-4-carboxylic acid;

1-(6-(2-((4-(1-(2-aminoacetyl)piperidin-4-yl)-2-methylphenoxy)methyl)cyclohex-1-en-1-yl)pyridin-2-yl)-5-(trifluoromethyl)-1H-pyrazole-4-carboxylic acid;

(+)-1-(6-(2-((4-(1-(cyclopropanecarbonyl)piperidin-4-yl)-2-methylphenoxy)methyl)-5-methylcyclohex-1-en-1-yl)pyridin-2-yl)-5-(trifluoromethyl)-1H-pyrazole-4-carboxylic acid;

(−)-1-(6-(2-((4-(1-(cyclopropanecarbonyl)piperidin-4-yl)-2-methylphenoxy)methyl)-5-methylcyclohex-1-en-1-yl)pyridin-2-yl)-5-(trifluoromethyl)-1H-pyrazole-4-carboxylic acid;

(+)-1-(6-(2-((4-(1-(cyclopropanecarbonyl)piperidin-4-yl)-3-ethylphenoxy)methyl)-3-methylcyclohex-1-en-1-yl)pyridin-2-yl)-5-(trifluoromethyl)-1H-pyrazole-4-carboxylic acid;

(−)-1-(6-(2-((4-(1-(cyclopropanecarbonyl)piperidin-4-yl)-3-ethylphenoxy)methyl)-3-methylcyclohex-1-en-1-yl)pyridin-2-yl)-5-(trifluoromethyl)-1H-pyrazole-4-carboxylic acid;

1-(6-(2-((4-(1-(cyclopropanecarbonyl)piperidin-4-yl)-3-ethylphenoxy)methyl)-3, 3-dimethylcyclohex-1-en-1-yl)pyridin-2-yl)-5-(trifluoromethyl)-1H-pyrazole-4-carboxylic acid;

(+)-1-(6-(2-((4-(1-(cyclopropanecarbonyl)piperidin-4-yl)-2-methylphenoxy)methyl)-3-methylcyclohex-1-en-1-yl)pyridin-2-yl)-5-(trifluoromethyl)-1H-pyrazole-4-carboxylic acid;

(−)-1-(6-(2-((4-(1-(cyclopropanecarbonyl)piperidin-4-yl)-2-methylphenoxy)methyl)-3-methylcyclohex-1-en-1-yl)pyridin-2-yl)-5-(trifluoromethyl)-1H-pyrazole-4-carboxylic acid;

(−)-1-(6-(2-((4-(1-(cyclopropanecarbonyl)piperidin-4-yl)-3-ethylphenoxy)methyl)-3-methylcyclohex-1-en-1-yl)pyridin-2-yl)-5-methyl-1H-pyrazole-4-carboxylic acid;

(+)-1-(6-(2-((4-(1-(cyclopropanecarbonyl)piperidin-4-yl)-3-ethylphenoxy)methyl)-3-methylcyclohex-1-en-1-yl)pyridin-2-yl)-5-methyl-1H-pyrazole-4-carboxylic acid;

(+)-1-(6-(2-((4-(1-(Cyclopropanecarbonyl)piperidin-4-yl)-3-ethylphenoxy)methyl)-3-methylcyclohex-1-en-1-yl)pyridin-2-yl)-5-ethyl-1H-pyrazole-4-carboxylic acid;

(−)-1-(6-(2-((4-(1-(Cyclopropanecarbonyl)piperidin-4-yl)-3-ethylphenoxy)methyl)-3-methylcyclohex-1-en-1-yl)pyridin-2-yl)-5-ethyl-1H-pyrazole-4-carboxylic acid;

5-Ethyl-1-(6-(2-((3-ethyl-4-(1-((S)-2-hydroxypropanoyl)piperidin-4-yl)phenoxy)methyl)-3-methylcyclohex-1-en-1-yl)pyridin-2-yl)-1H-pyrazole-4-carboxylic acid (diastereomer-1);

5-Ethyl-1-(6-(2-((3-ethyl-4-(1-((S)-2-hydroxypropanoyl)piperidin-4-yl)phenoxy)methyl)-3-methylcyclohex-1-en-1-yl)pyridin-2-yl)-1H-pyrazole-4-carboxylic acid (diastereomer-2);

1-(6-(2-((3-Ethyl-4-(1-((S)-2-hydroxypropanoyl)piperidin-4-yl)phenoxy)methyl)-3-methylcyclohex-1-en-1-yl)pyridin-2-yl)-5-methyl-1H-pyrazole-4-carboxylic acid (diastereomer-1);

1-(6-(2-((3-Ethyl-4-(1-((S)-2-hydroxypropanoyl)piperidin-4-yl)phenoxy)methyl)-3-methylcyclohex-1-en-1-yl)pyridin-2-yl)-5-methyl-1H-pyrazole-4-carboxylic acid (diastereomer-2);

(+)-1-(6-(2-((4-(1-(cyclopropanecarbonyl)piperidin-4-yl)-3-ethylphenoxy)methyl)-3-methylcyclohex-1-en-1-yl)pyridin-2-yl)-5-(difluoromethyl)-1H-pyrazole-4-carboxylic acid;

(−)-1-(6-(2-((4-(1-(cyclopropanecarbonyl)piperidin-4-yl)-3-ethylphenoxy)methyl)-3-methylcyclohex-1-en-1-yl)pyridin-2-yl)-5-(difluoromethyl)-1H-pyrazole-4-carboxylic acid;

1-(6-(2-((4-(1-(Cyclopropanecarbonyl)piperidin-4-yl)-2-methylphenoxy)methyl)cyclopent-1-en-1-yl)pyridin-2-yl)-5-(trifluoromethyl)-1H-pyrazole-4-carboxylic acid;

(+)-1-(6-(2-((4-(1-(Cyclopropanecarbonyl)piperidin-4-yl)-3-ethylphenoxy)methyl)-3-methylcyclopent-1-en-1-yl)pyridin-2-yl)-5-(trifluoromethyl)-1H-pyrazole-4-carboxylic acid;

(−)-1-(6-(2-((4-(1-(Cyclopropanecarbonyl)piperidin-4-yl)-3-ethylphenoxy)methyl)-3-methylcyclopent-1-en-1-yl)pyridin-2-yl)-5-(trifluoromethyl)-1H-pyrazole-4-carboxylic acid;

1-(6-(2-((4-(1-(Dimethylcarbamoyl)piperidin-4-yl)-2-methylphenoxy)methyl)cyclopent-1-en-1-yl)pyridin-2-yl)-5-(trifluoromethyl)-1H-pyrazole-4-carboxylic acid;

1-(6-(2-((4-(1-(2-hydroxyacetyl)piperidin-4-yl)-2-methylphenoxy)methyl)cyclopent-1-en-1-yl)pyridin-2-yl)-5-(trifluoromethyl)-1H-pyrazole-4-carboxylic acid;

1-(6-(2-((2-Methyl-4-(1-propionylpiperidin-4-yl)phenoxy)methyl)cyclopent-1-en-1-yl)pyridin-2-yl)-5-(trifluoromethyl)-1H-pyrazole-4-carboxylic acid;

1-(6-(2-((4-(1-(Methoxycarbonyl)piperidin-4-yl)-2-methylphenoxy)methyl)cyclopent-1-en-1-yl)pyridin-2-yl)-5-(trifluoromethyl)-1H-pyrazole-4-carboxylic acid;

1-(6-(2-((2-Methyl-4-(1-(methylsulfonyl)piperidin-4-yl)phenoxy)methyl)cyclopent-1-en-1-yl)pyridin-2-yl)-5-(trifluoromethyl)-1H-pyrazole-4-carboxylic acid;

1-(6-(2-((2-Methyl-4-(1-(2,2,2-trifluoroethyl)piperidin-4-yl)phenoxy)methyl)cyclopent-1-en-1-yl)pyridin-2-yl)-5-(trifluoromethyl)-1H-pyrazole-4-carboxylic acid;

1-(6-(2-(((4-(1-(cyclopropanecarbonyl)piperidin-4-yl)-3-ethylphenyl)amino)methyl)cyclohex-1-en-1-yl)pyridin-2-yl)-5-(trifluoromethyl)-1H-pyrazole-4-carboxylic acid;

1-(6-(2-(((4-(1-(Cyclopropanecarbonyl)piperidin-4-yl)-2-methylphenyl)amino)methyl)cyclohex-1-en-1-yl)pyridin-2-yl)-5-(trifluoromethyl)-1H-pyrazole-4-carboxylic acid;

1-(6-(2-(((4-(1-(Cyclopropanecarbonyl)piperidin-4-yl)phenyl)amino)methyl)cyclohex-1-en-1-yl)pyridin-2-yl)-5-(trifluoromethyl)-1H-pyrazole-4-carboxylic acid;

(±)-1-(6'-((4-(1-(Cyclopropanecarbonyl)piperidin-4-yl)-2-methylphenoxy)methyl)-T-methyl-2',3',4',5'-tetrahydro-[1,1'-biphenyl]-3-yl)-5-(trifluoromethyl)-1H-pyrazole-4-carboxylic acid;

1-(6-(2-((4-(1-(tert-butoxycarbonyl)piperidin-4-yl)-2-methylphenoxy)methyl)cyclohex-1-en-1-yl)pyridin-2-yl)-5-(trifluoromethyl)-1H-pyrazole-4-carboxylic acid;

1-(6-(2-((4-(1-(Cyclopropylmethyl)piperidin-4-yl)-2-methylphenoxy)methyl)cyclohex-1-en-1-yl)pyridin-2-yl)-5-(trifluoromethyl)-1H-pyrazole-4-carboxylic acid;

(±)-1-(6-(3-Methyl-2-(((2-(pyridin-2-ylmethyl)-1,2,3,4-tetrahydroisoquinolin-6-yl)oxy)methyl)cyclohex-1-en-1-yl)pyridin-2-yl)-5-(trifluoromethyl)-1H-pyrazole-4-carboxylic acid;

(±)-1-(6-(2-((4-((3,4-trans)-1-(cyclopropanecarbonyl)-3-hydroxypiperidin-4-yl)phenoxy)methyl)cyclohex-1-en-1-yl)pyridin-2-yl)-5-(trifluoromethyl)-1H-pyrazole-4-carboxylic acid; and pharmaceutically acceptable salts thereof.

In another aspect of the invention, synthetic intermediates which are suitable for use in the preparation of compounds of embodiments one to twenty of the invention are provided. In particular, intermediates are provided according to the formula:

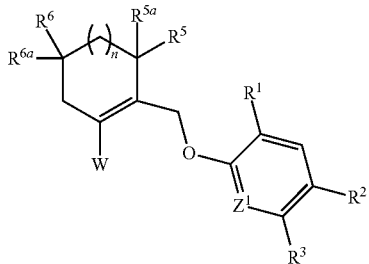

Where n, $Z^1$, $R^1$, $R^2$, $R^3$, $R^5$, $R^{5a}$, $R^6$ and $R^{6a}$ are substituents as defined in embodiment 1. W is a moiety suitable for transition metal mediated cross coupling reactions. In preferred intermediates W is a sulfonic acid ester (such as triflate ($OSO_2CF_3$), mesylate ($OSO_2CH_3$), or tosylate ($OSO_2CH_2C_6H_4Me$)) or W is a boronic acid (e.g. —$B(OH)_2$) or boronic ester (e.g., $B(Oalkyl)_2$ or 1,3,2-dioxaborolanyl optionally substituted with alkyl).

In certain aspects, preferred synthetic intermediates include compounds of the formula:

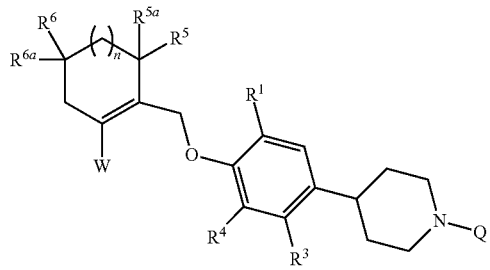

Where n, $R^1$, $R^3$, $R^4$, $R^5$, $R^{5a}$, $R^6$ and $R^{6a}$ are substituents as defined in embodiment 1. Q is $C(O)R^7$ or —$C(O)OR^7$ where $R^7$ is $C_1$-$C_4$alkyl or cyclopropyl. W is a moiety suitable for transition metal mediated cross coupling reactions. In preferred intermediates W is a sulfonic acid ester (such as triflate ($OSO_2CF_3$), mesylate ($OSO_2CH_3$), or tosylate ($OSO_2CH_2C_6H_4Me$)) or W is a boronic acid (e.g. —$B(OH)_2$) or boronic ester (e.g., $B(Oalkyl)_2$ or 1,3,2-dioxaborolanyl optionally substituted with alkyl).

Certain particularly preferred intermediates suitable for use in the preparation of some of the compounds of the invention include, 2-((4-(1-(Cyclopropanecarbonyl)piperidin-4-yl)-2-methylphenoxy)methyl)cyclohex-1-en-1-yl trifluoromethanesulfonatetert-Butyl 4-(3-Methyl-4-((2-(((trifluoromethyl)sulfonyl)oxy)cyclohex-1-en-1-yl)methoxy)phenyl)piperidine-1-carboxylate (±)-tert-Butyl 4-(2-ethyl-4-((6-methyl-2-(((trifluoromethyl)-sulfonyl)oxy)cyclohex-1-en-1-yl)methoxy)phenyl)piperidine-1-carboxylate (±)-tert-Butyl 4-(2-ethyl-4-((6-methyl-2-(4,4,5,5-tetramethyl-1,3,2-dioxaborolan-2-yl)cyclohex-1-en-1-yl)methoxy)phenyl)piperidine-1-carboxylate In a twentieth first embodiment, the present invention relates to a method of treating or preventing glaucoma or reducing intraocular pressure comprising administering to a subject in need thereof a sGC activator selected from the compounds of any one of embodiments one to sixteen. The invention has surprisingly shown that administration of sGC activators to a patient in need of therapy has desirable sustained efficacy in reducing IOP and in the treatment of glaucoma. Unless specified otherwise, the term "compounds of the present invention" refers to compounds of fomula (I) and subformulae thereof, and salts thereof, as well as all stereoisomers (including diastereoisomers and enantiomers), rotamers, tautomers and isotopically labeled compounds (including deuterium substitutions), as well as inherently formed moieties.

Depending on the choice of the starting materials and procedures, the compounds can be present in the form of one of the possible isomers or as mixtures thereof, for example as pure optical isomers, or as isomer mixtures, such as racemates and diastereomer mixtures, depending on the number of asymmetric carbon atoms. The present invention is meant to include all such possible isomers, including racemic mixtures, diastereomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of formula I in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

In another aspect, the present invention provides 1-(6-(2-((4-(1-(cyclopropanecarbonyl)piperidin-4-yl)-2-methylphenoxy)methyl)-5-methylcyclohex-1-en-1-yl)pyridin-2-yl)-5-(trifluoromethyl)-1H-pyrazole-4-carboxylic acid in sodium, potassium, ammonium, calcium, magnesium, iron, silver, zinc, and copper salt form; particularly suitable inorganic salts include ammonium, potassium, sodium, calcium and magnesium salts. The invention further provides 1-(6-(2-((4-(1-(cyclopropanecarbonyl)piperidin-4-yl)-2-methylphenoxy)methyl)-5-methylcyclohex-1-en-1-yl)pyridin-2-yl)-5-(trifluoromethyl)-1H-pyrazole-4-carboxylic acid in isopropylamine, benzathine, cholinate, diethanolamine, diethylamine, lysine, meglumine, piperazine and tromethamine salt forms. The compound of this embodiment is provided in salt form in racemic or enantiomerically enriched form.

In another aspect, the present invention provides 1-(6-(2-((4-(1-(cyclopropanecarbonyl)piperidin-4-yl)-3-ethylphenoxy)methyl)-3-methylcyclohex-1-en-1-yl)pyridin-2-yl)-5-methyl-1H-pyrazole-4-carboxylic acid in sodium, potassium, ammonium, calcium, magnesium, iron, silver, zinc, and copper salt form; particularly suitable inorganic salts include ammonium, potassium, sodium, calcium and magnesium salts. The invention further provides 1-(6-(2-((4-(1-(cyclopropanecarbonyl)piperidin-4-yl)-3-ethylphenoxy)methyl)-3-methylcyclohex-1-en-1-yl)pyridin-2-yl)-5-methyl-1H-pyrazole-4-carboxylic acid in isopropylamine, benzathine, cholinate, diethanolamine, diethylamine, lysine, meglumine, piperazine and tromethamine salt forms. The compound of this embodiment is provided in salt form in racemic or enantiomerically enriched form.

In another aspect, the present invention provides 1-(6-(2-((4-(1-(Cyclopropanecarbonyl)piperidin-4-yl)-3-ethylphenoxy)methyl)-3-methylcyclohex-1-en-1-yl)pyridin-2-yl)-5-ethyl-1H-pyrazole-4-carboxylic acid in sodium, potassium, ammonium, calcium, magnesium, iron, silver, zinc, and copper salt form; particularly suitable inorganic salts include ammonium, potassium, sodium, calcium and magnesium salts. The invention further provides 1-(6-(2-((4-(1-(Cyclopropanecarbonyl)piperidin-4-yl)-3-ethylphenoxy)methyl)-3-methylcyclohex-1-en-1-yl)pyridin-2-yl)-5-ethyl-1H-pyrazole-4-carboxylic acid in isopropylamine, benzathine, cholinate, diethanolamine, diethylamine, lysine, meglumine, piperazine and tromethamine salt forms. The compound of this embodiment is provided in salt form in racemic or enantiomerically enriched form.

In another aspect, the present invention provides 1-(6-(2-((4-(1-(cyclopropanecarbonyl)piperidin-4-yl)-2-methylphenoxy)methyl)-3-methylcyclohex-1-en-1-yl) pyridin-2-yl)-5-(trifluoromethyl)-1H-pyrazole-4-carboxylic acid in sodium, potassium, ammonium, calcium, magnesium, iron, silver, zinc, and copper salt form; particularly suitable inorganic salts include ammonium, potassium, sodium, calcium and magnesium salts. The invention further provides 1-(6-(2-((4-(1-(cyclopropanecarbonyl)piperidin-4-yl)-2-methylphenoxy)methyl)-3-methylcyclohex-1-en-1-yl)pyridin-2-yl)-5-(trifluoromethyl)-1H-pyrazole-4-carboxylic acid in isopropylamine, benzathine, cholinate, diethanolamine, diethylamine, lysine, meglumine, piperazine and tromethamine salt forms. The compound of this embodiment is provided in salt form in racemic or enantiomerically enriched form.

In another aspect, the present invention provides 1-(6-(2-((4-(1-(cyclopropanecarbonyl)piperidin-4-yl)-3-ethylphenoxy)methyl)-3-methylcyclohex-1-en-1-yl)pyridin-2-yl)-5-(trifluoromethyl)-1H-pyrazole-4-carboxylic acid in sodium, potassium, ammonium, calcium, magnesium, iron, silver, zinc, and copper salt form; particularly suitable inorganic salts include ammonium, potassium, sodium, calcium and magnesium salts. The invention further provides 1-(6-(2-((4-(1-(cyclopropanecarbonyl)piperidin-4-yl)-3-ethylphenoxy)methyl)-3-methylcyclohex-1-en-1-yl)pyridin-2-yl)-5-(trifluoromethyl)-1H-pyrazole-4-carboxylic acid in isopropylamine, benzathine, cholinate, diethanolamine, diethylamine, lysine, meglumine, piperazine and tromethamine salt forms. The compound of this embodiment is provided in salt form in racemic or enantiomerically enriched form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}$H, $^{3}$H, $^{11}$C, $^{13}$C, $^{14}$C, $^{15}$N, $^{18}$F $^{31}$P, $^{35}$S, $^{36}$Cl, $^{123}$I, $^{124}$I, $^{125}$I respectively. The invention includes various isotopically labeled compounds as defined herein, for example those into which radioactive isotopes, such as $^{3}$H and $^{14}$C, or those into which non-radioactive isotopes, such as $^{2}$H and $^{13}$C are present. Such isotopically labelled compounds are useful in metabolic studies (with $^{14}$C), reaction kinetic studies (with, for example $^{2}$H or $^{3}$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. D$_2$O, d$_6$-acetone, d$_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, activation of soluble guanylate cyclase activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by activation of sGC, or (ii) associated with decreased sGC activity, or (iii) characterized by activity (normal or abnormal) of sGC. In another non-limiting embodiment, the term "a therapeutically effective amount" refers to the amount of the compound of the present invention that, when administered to a cell, or a tissue, or a non-cellular biological material, or a medium, is effective to at least partially increasing the activity of sGC.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "activate", "activation" or "activating" refers to the significant increase in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

Typically, the compounds of formula (I) can be prepared according to the Schemes provided infra General Synthetic Aspects The following Examples serve to illustrate the invention without limiting the scope thereof.

Typically, the compounds of Formula (I) can be prepared according to the Schemes provided below.

Compounds such as 1-3; wherein $R^a$ is $C_1$-$C_4$ alkyl (preferably methyl or ethyl), $R^b$ is $R^a$ or trifluoromethyl, $W^a$ is CH or N, and $X^a$ is Cl or Br; can be prepared according to Scheme 1.

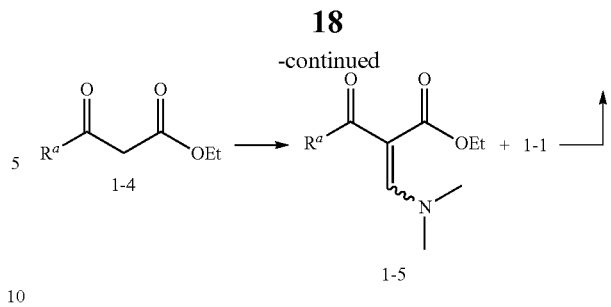

Aryl hydrazines 1-1 and beta-ketoester derivatives 1-2 can be reacted in an alcoholic solvent such as EtOH at temperatures between room temperature and reflux to provide the pyrazole derivatives 1-3. Alternatively, the beta-ketoester derivatives 1-5 can be prepared by a reaction of the corresponding beta-ketoesters 1-4 with N,N-dimethylformamide dimethyl acetal at room temperature. Reaction of 1-5 and 1-1 to afford 1-3 can be achieved by applying the similar condition described above for the reaction with 1-2.

Compounds such as 2-5; wherein $R^{c-1}$ is H, F, $R^a$, $C_1$-$C_4$ alkoxy, or hydroxymethyl; $R^{c-2}$ is $R^b$, hydrogen, $C_1$-$C_4$ alkoxy, or fluorine; and $R^d$ is hydrogen or methyl; $R^e$ is Boc, C(O)-Et, or —C(O)-cPr; and $R^w$ is C(O)-Et, or —C(O)-cPr can be synthesized according to Scheme 2.

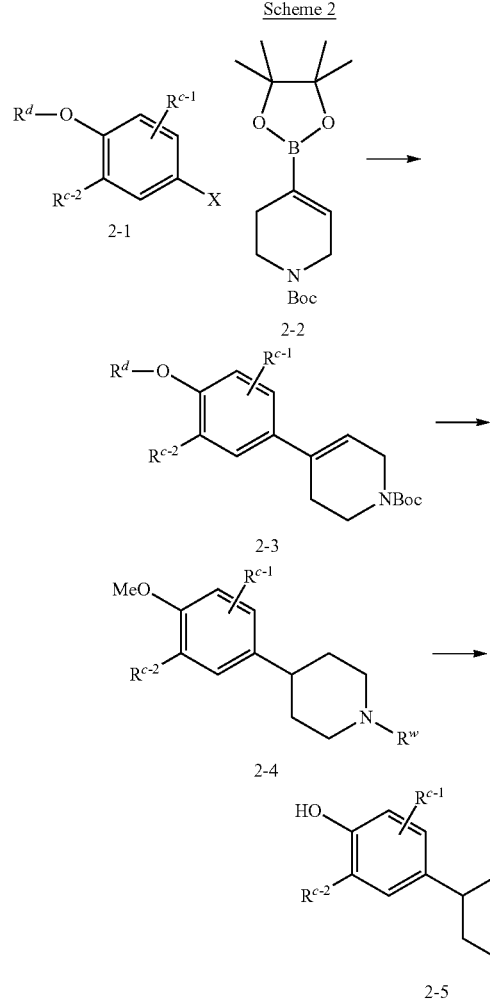

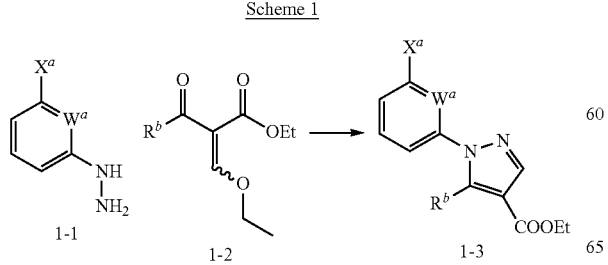

2-1 can be transformed to 2-3 utilizing a Suzuki-type coupling with boronate 2-2. 2-3, when $R^d$=Me, can be transformed into 2-4 via hydrogenation over catalysts such as Pd/C or platinum oxide, followed by treating with an acid such as TFA in an appropriate solvent such as $CH_2Cl_2$ and subsequent reaction with an acid anhydride such as propionic anhydride or an acid chloride such as cyclopropylcarbonyl chloride along with a trialkylamine base (e.g., trimethylamine). 2-4 can be transformed into 2-5 via treatment with boron tribromide in the appropriate solvent such as dichloromethane at low temperatures. Alternatively 2-3 when $R^d$=H can be directly converted to 2a-5 ($R^e$=Boc) by hydrogenation over catalysts such as Pd/C or platinum oxide, or 2-3 when $R^d$=H can be directly converted to 2-5 ($R^e$=$R^w$) by treating with an acid such as TFA in an appropriate solvent such as $CH_2Cl_2$ and subsequent reaction with an acid anhydride such as propionic anhydride or an acid chloride such as cyclopropylcarbonyl chloride along with a trialkylamine base (e.g., trimethylamine) followed by treatment with MeOH in the presence of $K_2CO_3$.

Compounds such as 2b-3 can be prepared from 2b-2, wherein $W^b$ is $NH_2$ or $NO_2$, according to Scheme 2b.

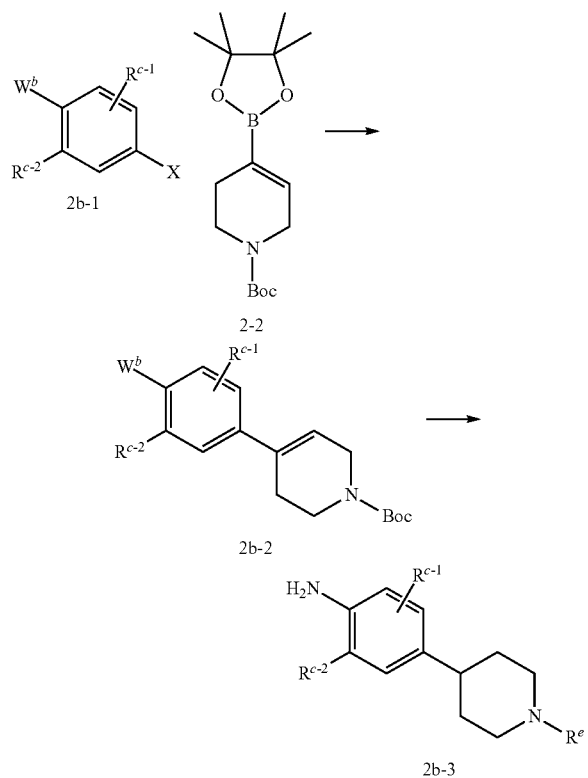

2b-1 can be transformed to 2b-2 utilizing a Suzuki-type coupling with boronate 2-2. 2b-2, when $W^b$=$NO_2$, can be transformed to 2b-3 by treating with an acid such as TFA in an appropriate solvent such as $CH_2Cl_2$ and subsequent reaction with an acid anhydride such as propionic anhydride or an acid chloride such as cyclopropylcarbonyl chloride along with a trialkylamine base (e.g., trimethylamine), followed by hydrogenation over catalysts such as Pd/C or platinum oxide. Alternatively, 2b-2, when $W^b$=$NO_2$ or $NH_2$ can be directly transformed to 2b-3, wherein $R^e$=Boc, by hydrogenation over catalysts such as Pd/C or platinum oxide.

Compounds such as 3a-4 can be prepared according to Scheme 3a.

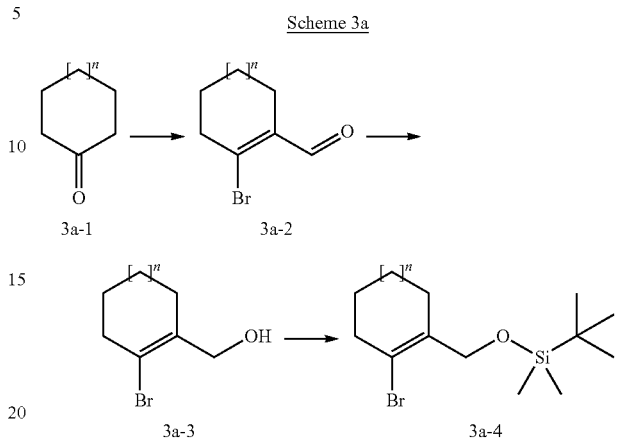

Ketone 3a-1 (n=0 or 1) can be transformed into bromoaldehyde 3a-2 by treatment with $PBr_3$ and DMF in DCM or chloroform at 0° C. or room temperature. Sodium borohydride reduction of aldehyde 3a-2 affords alcohol 3a-3 which can be converted to 3a-4 by treatment with TBSCl and imidazole at room temperature.

Compounds such as 3b-4 wherein $R^f$ is each independently selected from H or $C_1$-$C_4$ alkyl can be prepared according to Scheme 3b.

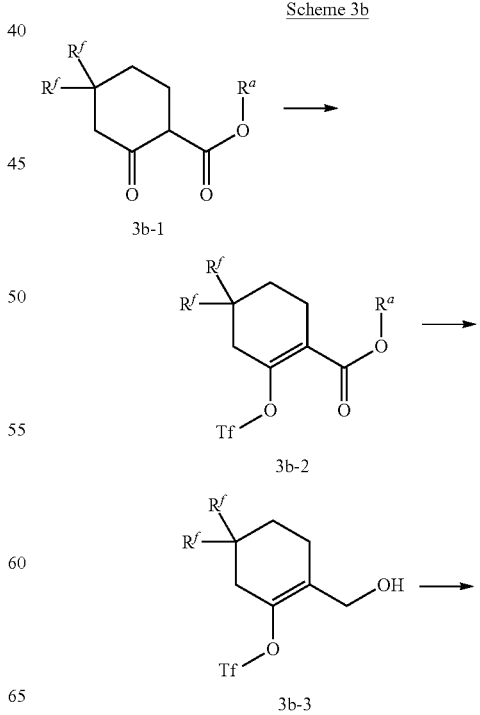

-continued

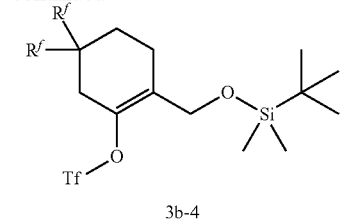

3b-4

Treatment of 3b-1 with NaH followed by reagents such as triflic anhydride in appropriate solvents such as THF or DCM at temperature between −78° C. to 0° C. to afford 3b-2. Subsequent reduction of 3b-2 by employing reducing reagents such as DIBAL at temperature between −78° C. to 0° C. in solvents such as DCM can afford alcohol 3b-3, which can then converted to the corresponding TBS ether 3b-4 as described in Scheme 3a (i.e. 3a-3→3a-4).

Compounds such as 3c-4 wherein $R^g$ is each independently selected from H or $C_1$-$C_4$ alkyl (preferably methyl) can be prepared according to Scheme 3c and as referenced in *Organic Letters* 2003, 5, 2869-2871.

Scheme 3c

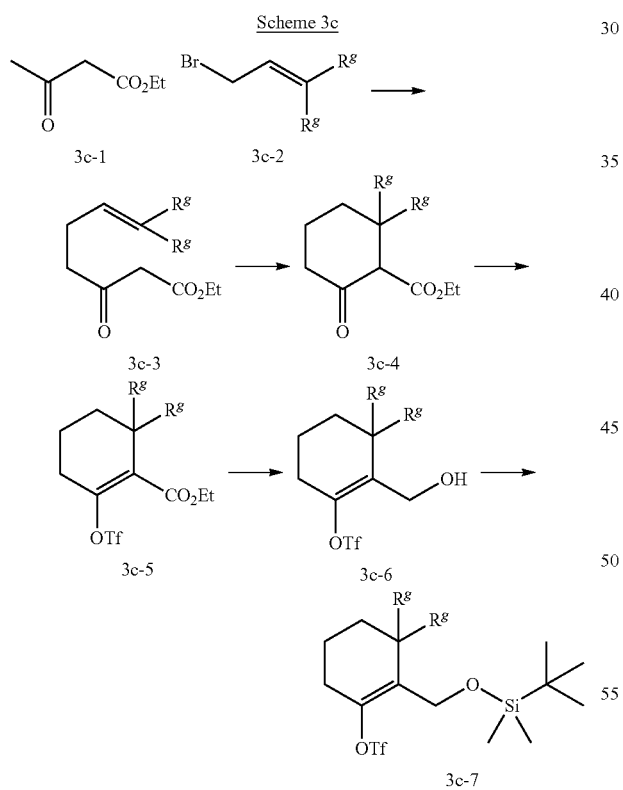

Treatment of ketoester 3c-1 with NaH and then n-BuLi, followed by alkylation with 3c-2 can afford compound type 3c-3, which can then be cyclized by employing dichlorobis(acetonitrile)palladium(II) in the presence of ytterbium(III) trifluoromethanesulfonate in a solvent such as dioxane at elevated temperature preferably 50° C. to afford cyclohexenone 3c-4. Transformation of 3c-4 to 3c-7 via 3c-5 and 3c-6 can be accomplished in accordance with the route described in Scheme 3b (i.e. 3b-1→3b-2→3b-3→3b-4).

Compounds such as 3d-2 in Scheme 3d can be prepared starting from appropriately substituted cyclopentanone analogue 3d-1 by the similar route as outlined in Scheme 3b.

Scheme 3d

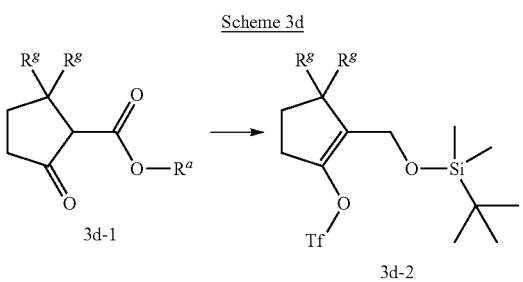

Compounds such as 4-1 wherein $X^b$=OTf or Br can be synthesized according to Scheme 4.

Scheme 4

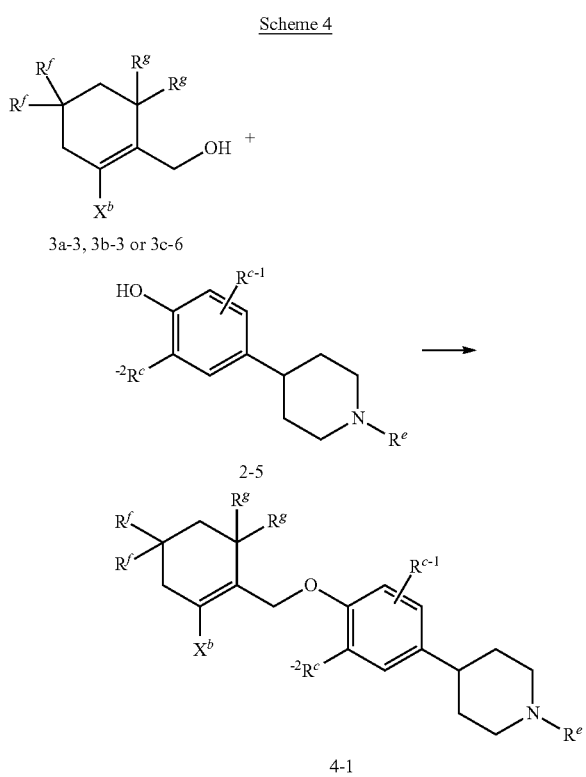

Hydroxymethylcyclohexene derivatives such as 3a-3, 3b-3, or 3c-6 can be reacted with a wide variety of phenol derivatives such as 2-5 by employing triaryl- or trialkylphosphines, such as triphenylphosphine, and an azodicarboxylate, such as DIAD, in a suitable solvent, such as DMF, toluene, or THF at temperatures between 0° C. to room temperature, or by employing tri-n-butyl cyanomethylenephosphorane in suitable solvents such as toluene at temperatures between 70° C. to 110° C. to afford 4-1.

Compounds such as 5-4 can be synthesized according to Scheme 5.

Scheme 5

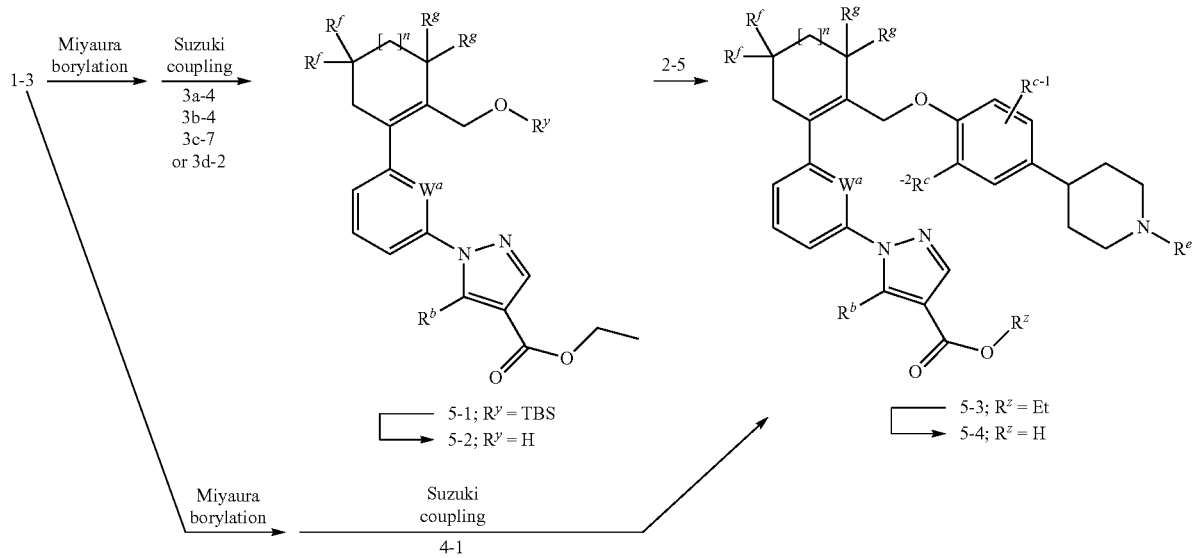

A Miyaura-type borylation of compounds of type 1-3 with bis(pinacolato)diboron employing conditions such as chloro(2-dicyclohexylphosphino-2',6'-dimethoxy-1,1'-biphenyl)[2-(2-aminoethylphenyl)]palladium(II)-methyl-t-butyl ether adduct and potassium acetate in dioxane at temperatures between 80° C. and 110° C. can provide corresponding boronic ester, which can then be reacted with 3a-4, 3b-4, 3c-7, or 3-2d by a Suzuki-type reaction utilizing conditions such as $Pd(dppf)Cl_2$ or chloro(2-dicyclohexylphosphino-2',6'-dimethoxy-1,1'-biphenyl)[2-(2-aminoethylphenyl)]palladium(II)-methyl-t-butyl ether adduct in the presence of a suitable aqueous base such as aqueous sodium carbonate in dioxane at temperatures between 80° C. to 110° C. to afford 5-1. Deprotection of 5-1 can be accomplished by treatment with TBAF in solvents such as THF at temperature between 0° C. to room temperature to afford 5-2, subsequent etherification of the generated alcohol 5-2 with phenols such as 2-5 can be achieved in accordance with the route described in Scheme 4 to afford 5-3.

Alternatively, compound type 5-3 can be synthesized by reacting 1-3 with triflate 4-1 with a similar manner as described above (i.e. 1-3→5-1).

Lastly, saponification of 5-3 can be accomplished employing conditions such as aqueous LiOH in a solvent mixture of MeOH and THF at temperatures between room temperature to 70° C. to afford 5-4.

Compounds such as 6-3 or 6-6 could be synthesized according to Scheme 6.

Scheme 6

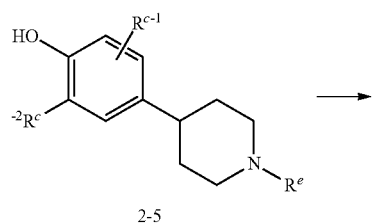

-continued

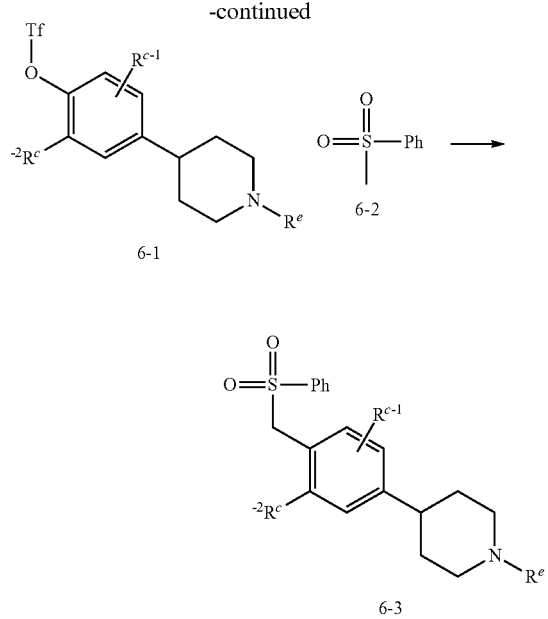

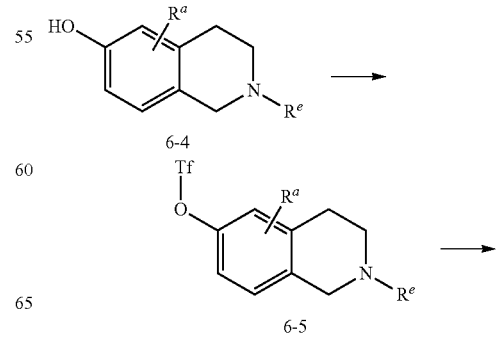

25
-continued

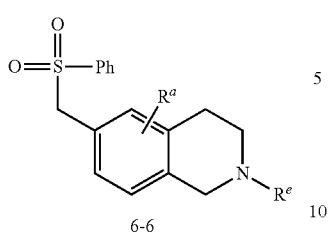

6-6

Preparation of intermediates 6-3 and 6-6 could be achieved by triflation of the corresponding phenol 2-5 and 6-4 with reagents such as triflic anhydride and a suitable base such as NaH. Sulfone 6-2 could then undergo palladium catalyzed α-arylation with the preformed triflates to give the corresponding arylsulfone intermediates 6-3 and 6-6 respectively.

Compounds such as 7-4 could be synthesized according to Scheme 7.

Scheme 7

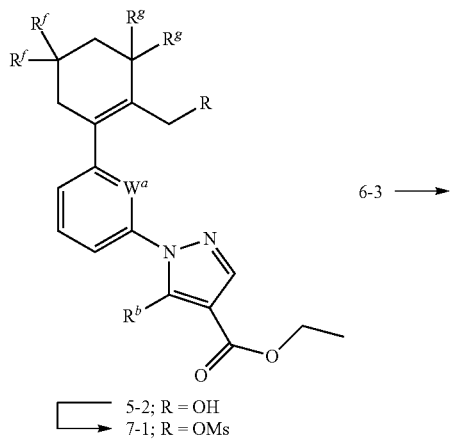

5-2; R = OH
7-1; R = OMs

26
-continued

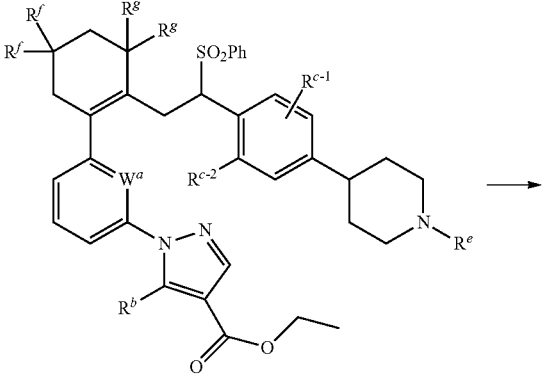

7-2

Conversion of alcohol 5-2 to mesylate 7-1 could be accomplished under standard conditions such as treatment with $Et_3N$ and MsCl. Alkylation of the above prepared sulfones 6-3 with mesylate 7-1 could be accomplished upon treatment with a suitable base such as LDA or nBuLi to give 7-2. Reductive removal of the phenyl sulfone moiety of 7-2 could be accomplished with reducing reagents such as zinc, sodium or magnesium under suitable conditions to give 7-3. Lastly, saponification of 7-3 could be accomplished with a similar manner as described in Scheme 5 to afford 7-4.

Compounds such as 8-2b, 8-3b, 8-4b and 8-5b wherein; L is O or $CH_2$; $R^{e-2}$ is $R^a$, $C_3$-$C_6$cycloalkyl, $C_1$-$C_4$alkoxy, $NH(C_1$-$C_4$alkyl), $N(C_1$-$C_4$alkyl)$_2$ or heteroaryl which heteroaryl has 5 or 6 ring atoms and 1 or 2 ring heteroatoms independently selected from the group consisting of N, O and S; $R^{e-3}$ is $C_1$-$C_4$alkyl which is optionally substituted with hydroxyl, or $C(O)C_3$-$C_6$cycloalkyl; $R^{e-4}$ is $C_1$-$C_4$alkyl or $C_3$-$C_6$cycloalkyl; and $R^{e-5}$ is $C_1$-$C_4$alkyl, halo$C_1$-$C_4$alkyl, or $C_3$-$C_6$cycloalkyl; can be synthesized according to Scheme 8.

Scheme 8
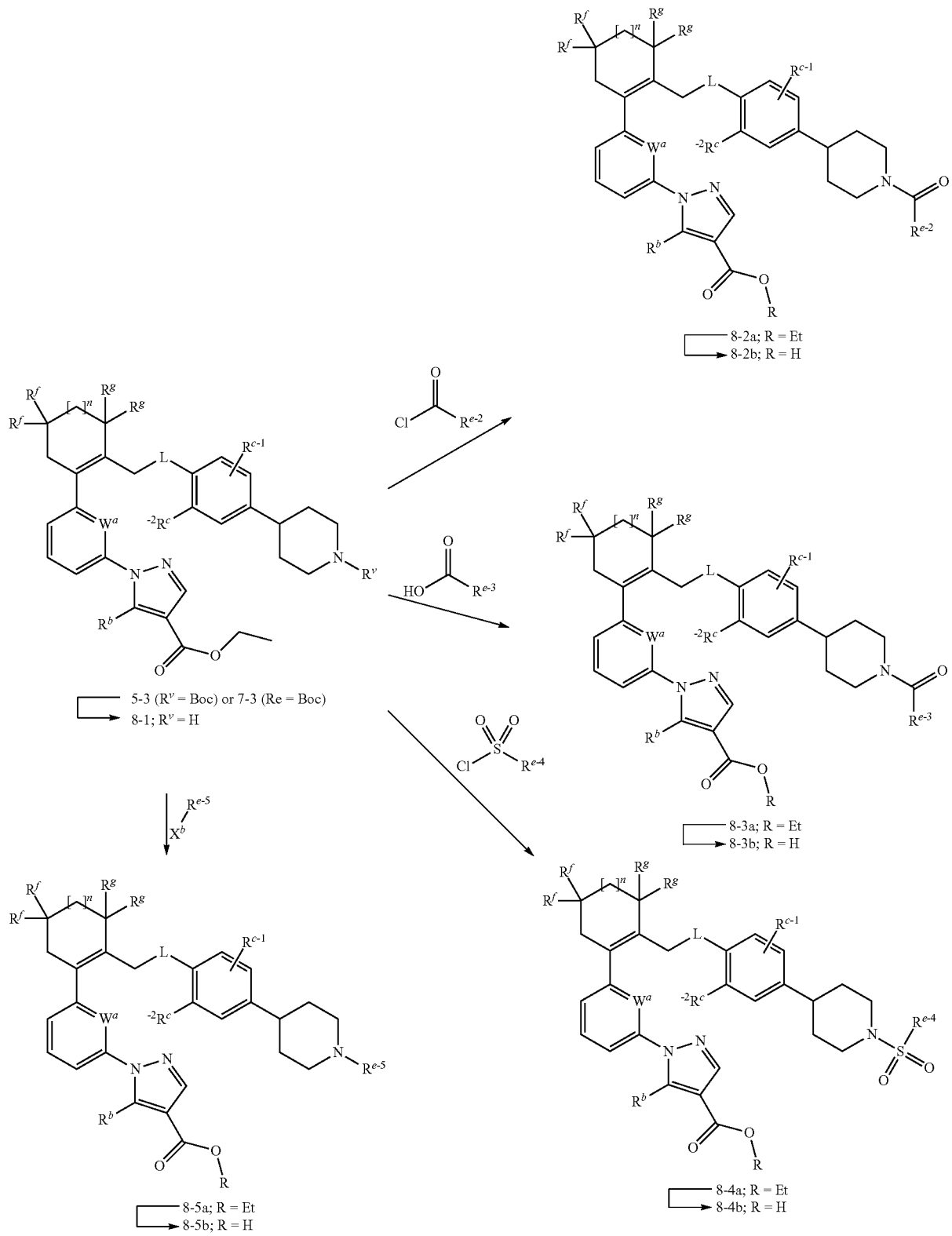
Deprotection of the Boc group of 5-3 (when $R^v$=Boc, L=O) or 7-3 (when $R^e$=Boc, L=CH$_2$) can be achieved by treatment with suitable acids such as TFA in solvents such as CH$_2$Cl$_2$ at temperatures between 0° C. to room temperature to provide 8-1, which can then be transformed to 8-2a by reactions with variety of chloroformates such as methyl chloroformate ($R^{e-2}$=—OMe), or carbamic chlorides such as dimethylcarbamic chloride ($R^{e-2}$=—NMe$_2$), or isocyanates such as ethyl isocyanate ($R^{e-2}$=—NHEt); or to 8-3a by peptide couplings with wide variety of carboxylic acids such as 2-cyclopropylacetic acid ($R^{e-3}$=—CH$_2$-cPr) or 2-hydroxypropanoic acid ($R^{e-3}$=—CH(OH)—CH$_3$) by employing peptide coupling methods well known to those skilled in the art (e.g., HATU, etc.); or to 8-4a by treatment of 8-1 with sulfonyl chlorides such as methanesulfonyl chloride ($R^{e-4}$=Me) in DCM in the presence of suitable bases such as DIPEA at temperatures between 0° C. to room temperature; or to 8-5a by alkylation of 8-1 with electrophiles such as 2,2,2-trifluoroethyl trifluoromethanesulfonate ($R^{e-5}$=CH$_2$CF$_3$) or cyclopropylmethyl bromide ($R^{e-5}$=—CH$_2$-cPr) utilizing conditions such as K$_2$CO$_3$ as a base in DMF as solvent at 60° C. Lastly, saponification of 8-2a, 8-3a, 8-4a and 8-5a can be accomplished by the method as described in Scheme 5 (i.e. 5-3→5-4).

Compound such as 9-2b can be synthesized according to Scheme 9.

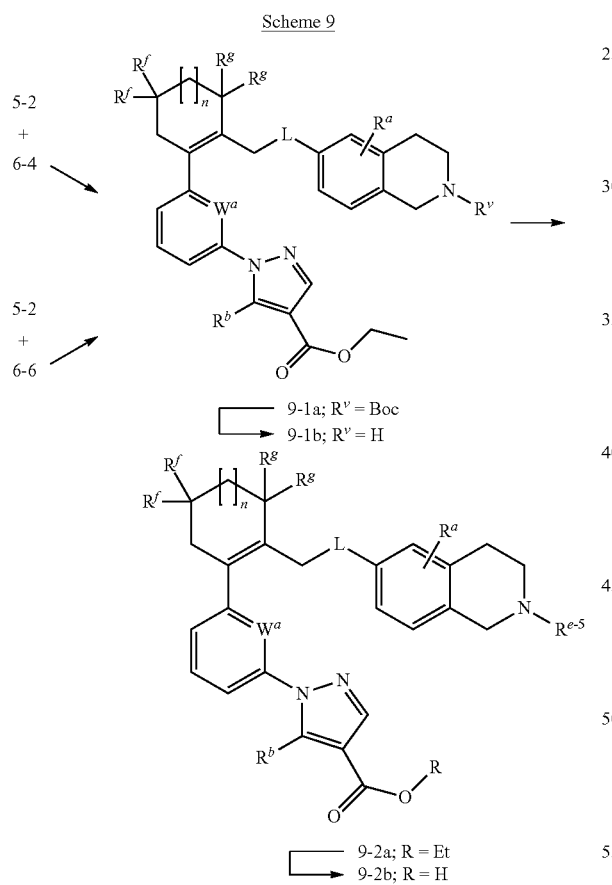

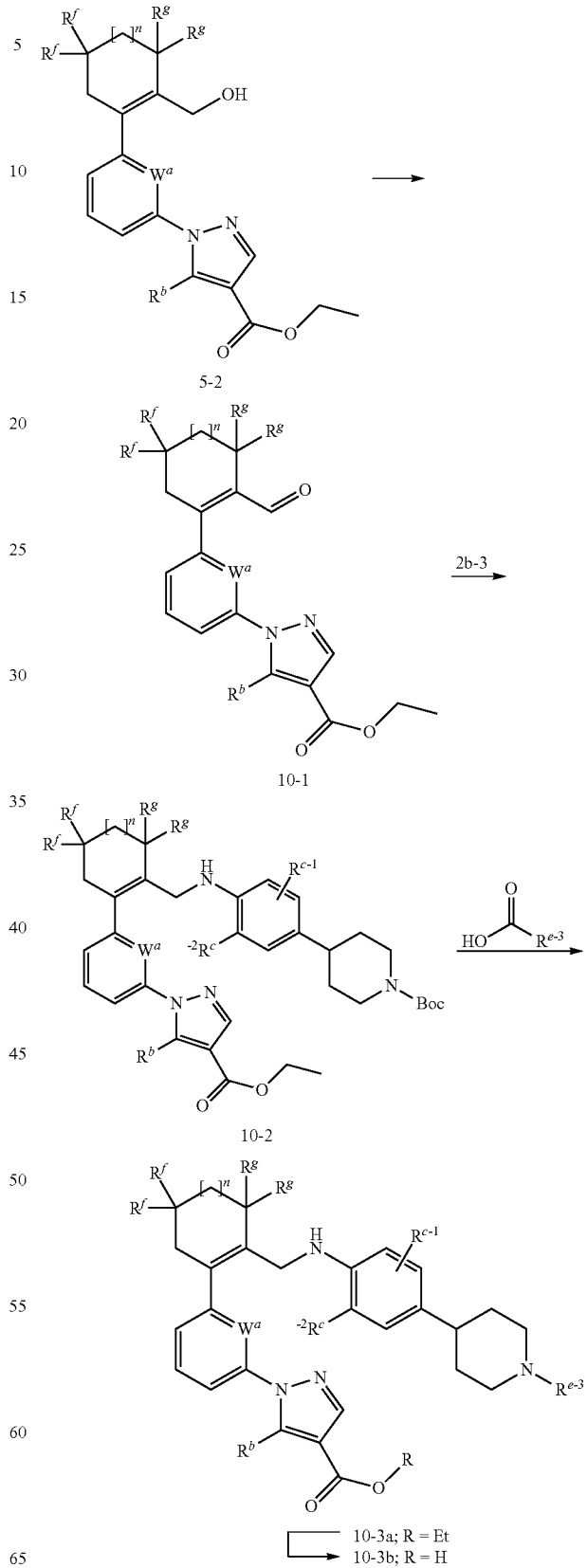

Compound 9-1a can be synthesized by a reaction of 5-2 with 6-4 (9-1a wherein L=O) by a similar method as described in Scheme 5 (i.e. 5-2→5-3); or starting from 5-2 and 6-6 (9-1a wherein L=CH$_2$) as outlined in Scheme 7. Transformation of 9-1a to 9-2b can be accomplished in accordance with the route described in Scheme 8 (i.e. 8-1→8-5a).

Compounds such as 10-3b can be synthesized according to Scheme 10.

Compound 5-2 (n=0 or 1) can be oxidized by oxidizing reagent such as manganase oxide to afford 10-1, subsequent reductive amination with the aniline 2b-3 can afford 10-2. Further transformation from 10-2 to 10-3a can be achieved by treatment with suitable acids such as TFA in solvents such as $CH_2Cl_2$ at temperatures between 0° C. to room temperature to remove the Boc moiety, followed by subsequent reaction with a carboxylic acid, such as cyclopropanecarboxylic acid, under peptide coupling conditions, e.g., in the presence of HATU and trimethylamine. Saponification of 10-3a can then be accomplished employing conditions such as aqueous LiOH in a solvent mixture of MeOH and THF at temperatures between room temperature to 70° C. to afford 10-3b.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with one or more of:
 a) diluents, e.g., lactose, dextrose, sucrose, mannitol, sorbitol, cellulose and/or glycine;
 b) lubricants, e.g., silica, talcum, stearic acid, its magnesium or calcium salt and/or polyethyleneglycol; for tablets also
 c) binders, e.g., magnesium aluminum silicate, starch paste, gelatin, tragacanth, methylcellulose, sodium carboxymethylcellulose and/or polyvinylpyrrolidone; if desired
 d) disintegrants, e.g., starches, agar, alginic acid or its sodium salt, or effervescent mixtures; and
 e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

Compositions of the present invention may be utilized in various dosage regimens known to those of skill in the art. Such dosing frequency is maintained for a varying duration of time depending on the therapeutic regimen. The duration of a particular therapeutic regimen may vary from one-time dosing to a maintenance regimen that extends for a month, year or more. One of ordinary skill in the art would be familiar with determining a therapeutic regimen for a specific indication. Preferred dosage regimens of the present invention include, but are not limited to, once a day dosing and twice a day dosing.

In the methods for the treatment of ocular disease and particularly for the treatment of glaucoma, set forth herein, administration to a subject of a composition of the present invention may be by various methods known to those of skill in the art, including, but not limited to, topical, subconjunctival, periocular, retrobulbar, subtenon, intraocular, subretinal, posterior juxtascleral, or suprachoroidal administration. In preferred embodiments, administration of a composition of the present invention is by topical administration to the ocular surface.

It is contemplated that the concentration of the sGC activator in the compositions of the present invention can vary, but is preferably 0.001 to 1.0 w/v % and more preferably 0.01-1.0 w/v % or 0.01-0.5 w/v %. The most preferred concentration range is from 0.01-0.3 w/v % and the most preferred concentration is between about 0.01 w/v % and 0.1 w/v %. The sGC activators of the present invention comprise the pharmaceutically useful hydrates and salts of such compounds and stereoisomers (where applicable), and may be formulated with a pharmaceutically acceptable vehicle.

The methods of treating glaucoma may include administering the sGC activator compound by a technique selected from the group consisting of: topical ocular administration, periocular injection, sub-conjunctival injection, sub-tenon injection, intracameral injection, intravitreal injection, intracanalicular injection, implanting delivery device in the cul-de-sac, implanting delivery device adjacent to the sclera, implanting delivery device within the eye, oral administration, intravenous administration, subcutaneous administration, intramuscular administration, parenteral administration, dermal administration, and nasal administration.

In certain aspects of the invention, compounds of the invention may be formulated in either fixed and unfixed combinations of two therapeutic agents effective in the treatment of glaucoma wherein one therapeutic agent is sGC activator disclosed supra and the second therapeutic agent is an efficacious glaucoma drug. In other embodiments, a pharmaceutical composition of the invention comprising a sGC activator can be administered to a patient alone or in combination with other IOP-lowering agents to increase the potency, efficacy and/or duration of the IOP reduction. In certain preferred combinations, the second IOP-lowering agent is selected from carbonic anhydrase inhibitors, beta-adrenergic receptor antagonists, prostaglandins, alpha-2 agonists, serotonin-2 agonists, alpha-1 antagonists, dopamine agonists, Rho kinase inhibitors, myosin-II Ca2+ATPase, inhibitors, matrix metalloproteinase activators, activator protein-1 (AP-1) activators, natriuretic peptide receptor-B agonists, phosphodiesterase inhibitors, K+-channel blockers and maxi-K-channel activators. The combination therapy of the invention provides the benefit of lowering IOP by two mechanisms, including inducing uveoscleral outflow of aqueous humor and inhibiting aqueous humor inflow, which can allow for reduced dosages of the compounds thereby lowering the risk of side effects.

Pharmaceutical compositions of the invention can also be advantageously combined with suitable neuroprotective agents such as memantine, eliprodil, Ca2+-channel blockers, and betaxolol.

In a further aspect of the invention, the sGC activator may be administered alone or in combination with a second therapeutic agent which is suitable for the treatment of glaucoma. Certain preferred second therapeutic agents include beta-adrenergic receptor antagonists, prostaglandin analogs, carbonic anhydrase inhibitors, α2 agonists, miotics, PDE-V inhibitors, Rho kinase inhibitors and neuroprotectants. In one preferred combination, a prostaglandin F2α analogue selected from the group consisting of Latanaprost and Travoprost is administered in combination with sGC activator of Formula (I) or subformulae thereof. In another preferred combination, a PDE-V inhibitor selected from the group consisting of Sildenafil, Tadalafil, Vardenafil, Udenafil, Avanafil, Lodenafil and Mirodenafil is administered in combination with a sGC activator of Formula (I) or subformulae thereof. In yet another preferred combination, a sGC activator of Formula (I) or subformulae thereof is administered in combination with a sGC stimulator (such as Riociguat) or a NO precursor (such as sodium nitroprusside or nitroglycerine). In another preferred combination, a sGC activator of Formula (I) or subformulae thereof is administered in combination with a Rho-kinase inhibitor (such as AR-13324 alone or combination of AR-13324 and Latanaprost).

In a further embodiment of the invention, a sGC activator of Formula (I) is administered in combination with a carbonic anhydrase inhibitor (such as Brinzolamide) for the treatment of glaucoma or to reduce IOP. In another embodiment, a sGC activator of Formula (I) is administered in combination with a α2 adrenergic agonist (such as Brimonidine) for the treatment of glaucoma or to reduce IOP. In a particularly preferred combination therapy, a sGC activator of Formula (I) is administered in combination with a fixed combination of Brimonidine and Brinzolamide (such as SIMBRINZA™ from by Alcon, Fort Worth, Tex.) for the treatment of glaucoma or to reduce IOP.

In certain embodiments, a sGC activator and the second pharmaceutical agent are administered concurrently in separate pharmaceutical compositions. In other embodiments, a sGC activator and the second pharmaceutical agent are administered formulated together in a pharmaceutical composition. In yet other embodiments, the sGC activator and the second pharmaceutical agent are administered sequentially in separate pharmaceutical compositions.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

In addition to a sGC activator, the compositions of the present invention optionally comprise one or more excipients. Excipients commonly used in pharmaceutical compositions include, but are not limited to, tonicity agents, preservatives, chelating agents, buffering agents, surfactants and antioxidants. Other excipients comprise solubilizing agents, stabilizing agents, comfort-enhancing agents, polymers, emollients, pH-adjusting agents and/or lubricants. Any of a variety of excipients may be used in compositions of the present invention including water, mixtures of water and water-miscible solvents, such as C1-C7-alkanols, vegetable oils or mineral oils comprising from 0.5 to 5% non-toxic water-soluble polymers, natural products, such as alginates, pectins, tragacanth, karaya gum, xanthan gum, carrageenin, agar and acacia, starch derivatives, such as starch acetate and hydroxypropyl cellulose or starch, and also other synthetic products such as polyvinyl alcohol, polyvinylpyrrolidone, polyvinyl methyl ether, polyethylene oxide, preferably cross-linked polyacrylic acid and mixtures of those products. The concentration of the excipient is, typically, from 1 to 100,000 times the concentration of the sGC activator. In preferred embodiments, excipients are selected on the basis of their inertness towards the sGC activator.

Relative to ophthalmic formulations, suitable tonicity-adjusting agents include, but are not limited to, mannitol, sodium chloride, glycerin, sorbitol and the like. Suitable buffering agents include, but are not limited to, phosphates, borates, acetates and the like. Suitable surfactants include, but are not limited to, ionic and nonionic surfactants (though nonionic surfactants are preferred), RLM 100, POE 20 cetylstearyl ethers such as Procol® CS20 and poloxamers such as Pluronic® F68. Suitable antioxidants include, but are not limited to, sulfites, ascorbates, butylated hydroxyanisole (BHA) and butylated hydroxytoluene (BHT).

The compositions set forth herein may comprise one or more preservatives. Examples of such preservatives include p-hydroxybenzoic acid ester, sodium chlorite, benzalkonium chloride, parabens such as methylparaben or propylparaben, alcohols such as chlorobutanol, benzyl alcohol or phenyl ethanol, guanidine derivatives such as polyhexamethylene biguanide, polymeric quaternary ammonium compounds such as Onamer M and Polyquaterium-1 (POLYQUAD® from Alcon), sodium perborate, or sorbic acid. In certain embodiments, the composition may be self-preserved that no preservation agent is required.

In preferred compositions a sGC activator of the present invention will be formulated for topical application to the eye in aqueous solution in the form of drops. The term "aqueous" typically denotes an aqueous composition wherein the composition is >50%, more preferably >75% and in particular >90% by weight water. These drops may be delivered from a single dose ampoule which may preferably be sterile and thus render bacteriostatic components of the composition unnecessary. Alternatively, the drops may be delivered from a multi-dose bottle which may preferably comprise a device which extracts any preservative from the composition as it is delivered, such devices being known in the art.

In other aspects, components of the invention may be delivered to the eye as a concentrated gel or a similar vehicle, or as dissolvable inserts that are placed beneath the eyelids. In yet other aspects, components of the invention may be delivered to the eye as ointments, water-in-oil and oil-in-water emulsions, solutions, or suspensions.

The compositions of the present invention, and particularly the topical compositions, are preferably isotonic or slightly hypotonic in order to combat any hypertonicity of tears caused by evaporation and/or disease. This may require a tonicity agent to bring the osmolality of the composition to a level at or near 210-320 milliosmoles per kilogram (mOsm/kg). The compositions of the present invention generally have an osmolality in the range of 220-320 mOsm/kg, and preferably have an osmolality in the range of 235-300 mOsm/kg. The ophthalmic compositions will generally be formulated as sterile aqueous solutions.

In certain embodiments, a sGC activator of the present invention is formulated in a composition that comprises one or more tear substitutes. A variety of tear substitutes are known in the art and include, but are not limited to: monomeric polyols, such as, glycerol, propylene glycol, and ethylene glycol; polymeric polyols such as polyethylene glycol; cellulose esters such hydroxypropylmethyl cellulose, carboxy methylcellulose sodium and hydroxy propylcellulose; dextrans such as dextran 70; vinyl polymers, such as polyvinyl alcohol; guars, such as HP-guar and other guar derivatives, and carbomers, such as carbomer 934P, carbomer 941, carbomer 940 and carbomer 974P. Certain compositions of the present invention may be used with contact lenses or other ophthalmic products.

In certain embodiments, the compositions set forth herein have a viscosity of 0.5-100 cps, preferably 0.5-50 cps, and most preferably 1-20 cps. These viscosities insure that the product is comfortable, does not cause blurring, and is easily processed during manufacturing, transfer and filling operations.

Preferred compositions are prepared using a buffering system that maintains the composition at a pH of about 3 to a pH of about 8.0, preferably 5.5-7.5, and most preferably 6.0-7.4. Topical compositions (particularly topical ophthalmic compositions) are preferred which have a physiological pH matching the tissue to which the composition will be applied or dispensed.

The following examples are presented to further illustrate selected embodiments of the present invention.

Topical Ocular Formulation Example

| Ingredient | Concentration (w/v %) |
| --- | --- |
| sGC activator | 0.1% |
| Dibasic Sodium Phosphate | 0.2% |
| Sodium Chloride | 0.75% |
| Disodium EDTA | 0.01% |
| Polysorbate 80 | 0.05% |
| Benzalkonium Chloride Solution | 0.01% |
| Hydroxypropyl Methylcellulose | 0.5% |

The compounds of formula I in free form or in pharmaceutically acceptable salt form, exhibit valuable pharmacological properties, e.g. sGC modulating properties, e.g. as indicated in vitro and in vivo tests as provided in the next sections, and are therefore indicated for therapy or for use as research chemicals, e.g. as tool compounds. More particularly, the compounds of formula I, in free form or in pharmaceutically acceptable salt form, activate sGC which is suitable for use in treatment of disease.

In one preferred use, the compounds of Formula I are suitable for use in lowering intra-ocular pressure (IOP) and in the treatment of glaucoma. The compounds of the invention may be used alone or in combination with a second therapeutic agent for the treatment of glaucoma. The embodiment further provides methods of treating glaucoma or reducing intraocular pressure in a subject, the method comprising administering a compound of Formula I alone or in combination with a second therapeutic agent. In certain aspects, the method contemplates to topical ocular administration of the compound of Formula I to the subject in need of such therapy. In preferred aspects, the method comprises administration of the compound of Formula I as a mono-therapy. In certain other aspects, the method comprises the co-administration (either concomitantly or sequentially) of a compound of Formula I and a PDE-V inhibitor.

In a particularly preferred use, 1-(6-(2-((4-(1-(cyclopropanecarbonyl)piperidin-4-yl)-2-methylphenoxy)methyl)-5-methylcyclohex-1-en-1-yl)pyridin-2-yl)-5-(trifluoromethyl)-1H-pyrazole-4-carboxylic acid, 1-(6-(2-((4-(1-(cyclopropanecarbonyl)piperidin-4-yl)-3-ethylphenoxy)methyl)-3-methylcyclohex-1-en-1-yl)pyridin-2-yl)-5-methyl-1H-pyrazole-4-carboxylic acid, 1-(6-(2-((4-(1-(Cyclopropanecarbonyl)piperidin-4-yl)-3-ethylphenoxy)methyl)-3-methylcyclohex-1-en-1-yl)pyridin-2-yl)-5-ethyl-1H-pyrazole-4-carboxylic acid, 1-(6-(2-((4-(1-(cyclopropanecarbonyl)piperidin-4-yl)-2-methylphenoxy)methyl)-3-methylcyclohex-1-en-1-yl)pyridin-2-yl)-5-(trifluoromethyl)-1H-pyrazole-4-carboxylic acid, or 1-(6-(2-((4-(1-(cyclopropanecarbonyl)piperidin-4-yl)-3-ethylphenoxy)methyl)-3-methylcyclohex-1-en-1-yl)pyridin-2-yl)-5-(trifluoromethyl)-1H-pyrazole-4-carboxylic acid or a pharmaceutically acceptable salt thereof are suitable for use in lowering intra-ocular pressure (IOP) and in the treatment of glaucoma. 1-(6-(2-((4-(1-(Cyclopropanecarbonyl)piperidin-4-yl)-2-methylphenoxy)methyl)-5-methylcyclohex-1-en-1-yl)pyridin-2-yl)-5-(trifluoromethyl)-1H-pyrazole-4-carboxylic acid, 1-(6-(2-((4-(1-(cyclopropanecarbonyl)piperidin-4-yl)-3-ethylphenoxy)methyl)-3-methylcyclohex-1-en-1-yl)pyridin-2-yl)-5-methyl-1H-pyrazole-4-carboxylic acid, 1-(6-(2-((4-(1-(Cyclopropanecarbonyl)piperidin-4-yl)-3-ethylphenoxy)methyl)-3-methylcyclohex-1-en-1-yl)pyridin-2-yl)-5-ethyl-1H-pyrazole-4-carboxylic acid, 1-(6-(2-((4-(1-(cyclopropanecarbonyl)piperidin-4-yl)-2-methylphenoxy)methyl)-3-methylcyclohex-1-en-1-yl)pyridin-2-yl)-5-(trifluoromethyl)-1H-pyrazole-4-carboxylic acid, or 1-(6-(2-((4-(1-(cyclopropanecarbonyl)piperidin-4-yl)-3-ethylphenoxy)methyl)-3-methylcyclohex-1-en-1-yl)pyridin-2-yl)-5-(trifluoromethyl)-1H-pyrazole-4-carboxylic acid or a pharmaceutically acceptable salt thereof may be used alone or in combination with a second therapeutic agent for the treatment of glaucoma. The embodiment further provides methods of treating glaucoma or reducing intraocular pressure in a subject, the method comprising administering one of the specific compounds listed supra alone or in combination with a second therapeutic agent. In certain aspects, the method contemplates topical ocular administration of one of the specific compounds listed supra to the subject in need of such therapy. In preferred aspects, the method comprises administration of one of these specific compounds as a mono-therapy. In certain other aspects, the method comprises the co-administration (either concomitantly or sequentially) of a compound of Formula I and a PDE-V inhibitor. 1-(6-(2-((4-(1-(Cyclopropanecarbonyl)piperidin-4-yl)-2-methylphenoxy)methyl)-5-methylcyclohex-1-en-1-yl)pyridin-2-yl)-5-(trifluoromethyl)-1H-pyrazole-4-carboxylic acid, 1-(6-(2-((4-(1-(cyclopropanecarbonyl)piperidin-4-yl)-3-ethylphenoxy)methyl)-3-methylcyclohex-1-en-1-yl)pyridin-2-yl)-5-methyl-1H-pyrazole-4-carboxylic acid, 1-(6-(2-((4-(1-(Cyclopropanecarbonyl)piperidin-4-yl)-3-ethylphenoxy)methyl)-3-methylcyclohex-1-en-1-yl)pyridin-2-yl)-5-ethyl-1H-pyrazole-4-carboxylic acid, 1-(6-(2-((4-(1-(cyclopropanecarbonyl)piperidin-4-yl)-2-methylphenoxy)methyl)-3-methylcyclohex-1-en-1-yl)pyridin-2-yl)-5-(trifluoromethyl)-1H-pyrazole-4-carboxylic acid, or 1-(6-(2-((4-(1-(cyclopropanecarbonyl)piperidin-4-yl)-3-ethylphenoxy)methyl)-3-methylcyclohex-1-en-1-yl)pyridin-2-yl)-5-(trifluoromethyl)-1H-pyrazole-4-carboxylic acid may be used in the treatment of glaucoma or reducing intraocular pressure in racemic or enantiomerically enriched form.

Compounds of the invention may also be useful in the treatment of an indication selected from: kidney disease, urologic disorders hypertension, atherosclerosis, peripheral artery disease, restenosis, stroke, heart failure, coronary vasospasm, cerebral vasospasm, ischemia/reperfusion injury, thromboembolic pulmonary hypertension, pulmonary arterial hypertension, stable and unstable angina, thromboembolic disorders. In addition, the compounds of the invention have the potential to treat renal disease, diabetes, fibrotic disorders (including those of the liver, kidney and lungs), urologic disorders (including overactive bladder), benign prostatic hyperplasia, erectile dysfunction, neuropathic pain and neurological disorders (Including Alzheimer's disease and Parkinson's disease). Treatment with an sGC activator of the invention may further provide benefit in the treatment of inflammatory disorder such as psoriasis, multiple sclerosis, arthritis, asthma, cystic fibrosis and chronic obstructive pulmonary disease.

Thus, as a further embodiment, the present invention provides the use of a compound of formula (I) in therapy. In a further embodiment, the therapy is selected from a disease which may be treated by activation of sGC. In a preferred application, the disease is selected from the afore-mentioned list, suitably glaucoma.

In another embodiment, the invention provides a method of treating a disease which is treated by activation of sGC comprising administration of a therapeutically acceptable amount of a compound of formula (I) or a salt thereof. In a further embodiment, the disease is selected from the afore-mentioned list, suitably glaucoma.

Thus, as a further embodiment, the present invention provides the use of a compound of formula (I) or subformulae thereof for the manufacture of a medicament. In a further embodiment, the medicament is for treatment of a disease which may be treated by activation of sGC. In another embodiment, the disease is selected from the afore-mentioned list, suitably glaucoma.

For systemic administration, the administered pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods.

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

ABBREVIATIONS

Ac Acetyl
AcOH acetic acid
AIBN azobisisobutyronitrile
App, app. apparent
aq. aqueous
atm atmosphere
Bis(pinacolato)diboron 4,4,4',4',5,5,5',5'-Octamethyl-2,2'-bi-1,3,2-dioxaborolane
Boc tertiary butyl carboxy
Boc-anhydride di-tert-butyl dicarbonate
$(Boc)_2O$ di-tert-butyl dicarbonate
br. broad
BSA bovine serum albumin
BuOH butanol
calcd. calculated
CHAPS 3-[(3-cholamidopropyl)dimethylammonio]-1-propanesulfonate
$CH_3CN$ acetonitrile
$Cs_2CO_3$ cesium carbonate
d doublet
DBU 1,8-diazabicyclo[5.4.0]undec-7-ene
dd doublet of doublets
DCE 1,2-dichloroethane
DCM dichloromethane
DEA diethylamine
DEAD diethyl azodicarboxylate
DIAD diisopropyl azodicarboxylate
DIEA N,N-diisopropylethylamine
DIBAL-H diisobutylaluminium hydride
DIPEA N,N-diisopropylethylamine
DMAP 4,4-dimethylaminopyridine
DME 1,4-dimethoxyethane
DMF N,N-dimethylformamide
Dess-Martin Periodinane Dess-Martin reagent; 1,1,1-triacetoxy-1,1-dihydro-1,2-benziodoxol-3(11-1)-one (CAS#87413-09-0)
DMSO dimethylsulfoxide
ESI electrospray ionization
EtOAc, AcOEt ethyl acetate
Et ethyl
EtOH ethanol
Ex Example
FCC flash column chromatography
g grams
h hour(s)
HATU 2-(1H-7-azabenzotriazol-1-yl)-1,1,3,3-tetramethyl uronium hexafluorophosphate methanaminium
HBTU O-benzotriazole-N,N,N',N'-tetramethyl-uronium-hexafluoro-phosphate
HC HPLC condition
HBSS Hank's Balanced Salt Solution
HEPES 4-(2-hydroxyethyl)-1-piperazineethanesulfonic acid
HFIP 1,1,1,3,3,3-hexafluoro-2-propanol
HPLC high performance liquid chromatography
IBMX 1-methyl-3-(2-methylpropyl)-7H-purine-2,6-dione
IPA 2-propanol
IR infrared spectroscopy
L liter(s)
LDA lithium diisopropyl amide
LHMDS lithium bis(trimethylsilyl)amide
M molar
MHz mega Hertz
m multiplet
Me methyl
MeCN acetonitrile
MeI iodomethane
MeOH methanol
mg milligram(s)
mm millimeter(s)
min minutes
ml milliliter(s)
mL milliliter(s)
mmol millimoles
MP melting point
MS mass spectrometry
MsCl methanesulfonyl chloride
$Ms_2O$ methanesulfonyl anhydride
MsOH methanesulfonic acid
MTBE methyl tert-butylether
m/z mass to charge ratio
N normal
$NaBH_4$ sodium borohydride
$Na(AcO)_3BH$ sodium triacetoxyborohydride
NBS N-bromosuccinimide
NCS N-chlorosuccinimide
$NH_4Cl$ ammonium chloride
NMR nuclear magnetic resonance
ODQ 1H-[1,2,4] Oxadiazolo[4,3-a]quinoxalin-1-one (CAS#41443-28-1)
PBS phosphate buffered saline
Pd/C palladium on carbon
$Pd(dppf)_2Cl_2$ $CH_2Cl_2$ adduct 1,1'-bis(diphenylphosphino)ferrocene-palladium(II)dichloride complex
$Pd(PPh_3)_4$ tetrakis(triphenylphosphine)palladium(0)
Ph phenyl
ppm parts per million
PyBOP benzotriazol-1-yloxytripyrrolidinophosphonium hexafluorophosphate
rac racemic
RP reverse phase
Rochelle's salt Potassium sodium tartrate (CAS#304-59-6)
rt room temperature
s singlet
sat. saturated
sat'd. saturated
SFC Supercritical Fluid Chromatography
t triplet
$t_r$ retention time
T3P propylphosphonic anhydride
TBAF tetra-n-butylammonium fluoride TBAT tetrabutylammonium difluorotriphenylsilicate
TBS tert-butyldimethylsilyl
TBSCl tert-butyldimethylsilyl chloride
TEA, Et$_3$N triethylamine
tert-tertiary
TFA trifluoroacetic acid
THF tetrahydrofuran
TLC Thin Layer Chromatography
TMP 2,2',6,6'-tetramethylpiperidine, 2,2',6,6'-tetramethylpiperidyl
TMSCF$_3$ trifluoromethyltrimethylsilane
TMS trimethylsilyl
Ts p-toluenesulfonyl
TsOH p-toluenesulfonic acid
UPLC ultra performance liquid chromatography
v/v volume per volume
w/v weight per volume
w/w weight per weight The following examples are intended to illustrate the invention and are not to be construed as being limitations thereon. Unless otherwise stated, one or more tautomeric forms of compounds of the examples described hereinafter may be prepared in situ and/or isolated. All tautomeric forms of compounds of the examples described hereafter should be considered to be disclosed. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

All reactions are carried out under nitrogen or argon unless otherwise stated. Optical rotations were measured in MeOH, using D line of a sodium lamp.

Proton NMR ($^1$H NMR) is conducted in deuterated solvent. In certain compounds disclosed herein, one or more $^1$H shifts overlap with residual proteo solvent signals; these signals have not been reported in the experimental provided hereinafter.

Multiple parent ion masses are reported for mass spectroscopy data when the compound of the invention contains one or more bromine atoms. Bromine exists as an approximately 1:1 molar ratio of $^{79}$Br:$^{81}$Br. Thus, a compound with a single bromine atom will exhibit two parent mass ions having a difference of 2 amu. The smaller mass is reported in the Experimental infra.

Following preparation methods were used for RP-HPLC.
HC-A:
Stationary phase: Waters SunFire™ Prep C18 OBD™ 5 μm, 30×100 mm
Mobile phase: gradient, water with 0.1% TFA/acetonitrile
HC-B
Stationary phase: Gemini® NX 5μ C18 110A 100×30 mm
Mobile phase: gradient, water with 0.1% (28% ammonium hydroxide)/acetonitrile
HC-C
Stationary phase: X-Bridge® BEH C18 OBD Prep 5 μm, 30 mm 50 mm
Mobile phase: gradient, water with 0.1% (28% ammonium hydroxide)/acetonitrile Absolute stereochemistry, retention times on chiral HPLC, and/or optical rotations are provided for the embodiments of the invention where applicable. The invention contemplates all stereochemical forms of the compounds provided herein. Where absolute stereochemistry is provided the assessment was made via X-ray diffraction, and/or chemical correlation, and/or at least one chiral center was from a purchased commercial enantiopure (>15:1 er) starting material In the case of racemic samples, including intermediates, enantiomers are separated by chromatography using a chiral stationary phase and are identified/differentiated either by HPLC retention time employing a chiral stationary phase and the monikers "enantiomer-1" or "enantiomer-2", and/or by a specific "+" or "−" sign referring to the rotation of polarized light when this data is available.

In some instances, molecules may be prepared using synthetic conditions that result in a mixture of diastereomers or enantiomers. The individual stereoisomer may be separated using standard separation techniques such as chiral SFC. When the absolute stereochemistry of the purified enantiomer is unknown, the individual enantiomers are identified by optical rotation or as "enantiomer-1" and "enantiomer-2" and/or by chiral SFC retention times. When the absolute stereochemistry of diastereomers is unknown or partially known (i.e., one or more chiral centers have known absolute stereochemistry but at least one additional chiral center has unknown absolute stereochemistry), then the resulting mixture of diastereomers are separated via chiral SFC to afford the two separate diastereomers both in enantiomerically pure (e. g >90% ee) form. The individual diastereomers are identified as "diastereomer-1" and "diastereomer-2" and/or by chiral SFC retention times.

In some instances examples possess an acidic functional group as such during final purification procedures samples may contain an undetermined mixture of the free acid along with potassium and/or lithium salts of the titled compound. Small changes in the amount of salt present may change the observed chemical shift or intensity for some peaks in the $^1$H NMR spectra.

Intermediate 1-1. Ethyl 1-(6-bromopyridin-2-yl)-5-(trifliuoromethyl)-1H-pyrazole-4-carboxylate

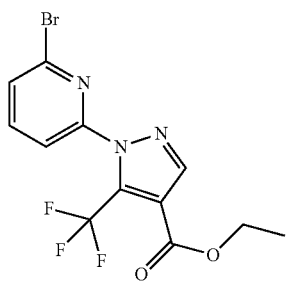 [SMILES: CCOC(=O)c1cnn(-c2cccc(Br)n2)c1C(F)(F)F]

A solution of 2-bromo-6-hydrazinylpyridine (CAS#26944-71-8; 12.63 g, 67 mmol) in THF (350 mL) was cooled in an acetone/CO$_2$ bath, and then ethyl 2-(ethoxymethylene)-4,4,4-trifluoro-3-oxobutyrate (CAS#571-55-1, 13.72 mL, 71 mmol) was added dropwise. Once the addition was complete, the reaction mixture was gradually allowed to warm to rt over 2 h. The reaction mixture was then concentrated, and the residue dissolved in EtOAc. The organic layer was then washed successively with sat. aq. NaHCO$_3$ and brine. The organic layer was then dried over MgSO$_4$, filtered, and concentrated. The resulting residue was purified by silica gel flash column chromatography (10% EtOAc in hexane) to afford the title compound. $^1$H NMR (400 MHz, CD$_3$OD) δ 8.19 (s, 1H), 7.96 (t, J=7.82 Hz, 1H), 7.74-7.80 (m, 2H), 4.37 (q, J=7.13 Hz, 2H), 1.38 (t, J=7.15 Hz, 3H).

Intermediate 1-2

The following compounds were prepared with similar methods as described above using the appropriate hydrazines and 3-oxobutyrates as starting materials as delineated in the table below.

Intermediate 1-3. Ethyl 1-(6-bromopyridin-2-yl)-5-ethyl-1H-pyrazole-4-carboxylate

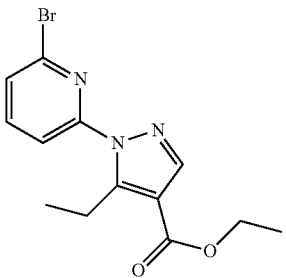 [SMILES: CCOC(=O)c1cnn(-c2cccc(Br)n2)c1CC]

| Intermediate | Structure/Chemical Name | Starting materials | Analytical data |
|---|---|---|---|
| 1-2-1 | Ethyl 1-(6-chloropyridin-2-yl)-5-(trifluoromethyl)-1H-pyrazole-4-carboxylate | 2-chloro-6-hydrazinylpyridine (CAS# 5193-03-3) and ethyl 2-(ethoxymethylene)-4,4,4-trifluoro-3-oxobutyrate (CAS# 571-55-1) | $^1$H NMR (400 MHz, DMSO-d$_6$) δ 8.38 (s, 1H), 8.22 (dd, J = 7.8, 7.9 Hz, 1H), 7.86 (dd, J = 0.63, 8.0 Hz, 1H), 7.81 (dd, J = 0.63, 8.0 Hz, 1H), 4.33 (q, J = 7.15 Hz, 2H), 1.31 (t, J = 7.15 Hz, 3H) |
| 1-2-2 | Ethyl 1-(3-bromophenyl)-5-(trifluoromethyl)-1H-pyrazole-4-carboxylate | (3-bromophenyl)hydrazine hydrochloride (CAS# 27246-81-7) and ethyl 2-(ethoxymethylene)-4,4,4-trifluoro-3-oxobutyrate (the reaction was carried in the presence of Et$_3$N) | MS (ESI+) m/z 362.9 (M + H) |
| 1-2-3 | Ethyl 1-(6-bromopyridin-2-yl)-5-(difluoromethyl)-1H-pyrazole-4-carboxylate | 2-Bromo-6-hydrazinylpyridine and ethyl 2-(ethoxymethylene)-4,4-difluoro-3-oxobutyrate (CAS# 176969-33-8) | MS (ESI+) m/z 346.2, (M + H) |

A solution of 2-bromo-6-hydrazinylpyridine (2 g, 10.64 mmol) and ethyl 2-((dimethylamino)methylene)-3-oxopentanoate (CAS#89193-23-7, 2.33 g, 11.7 mmol) in EtOH (32 mL) was stirred at 70° C. for 1.5 h, and then cooled to rt. The reaction mixture was then poured into H₂O. The resulting precipitate was collected by filtration and washed with H₂O to furnish the title compound. MS (ESI+) m/z 324.1 (M+H).

Intermediate 1-4. Ethyl 1-(3-(4,4,5,5-tetramethyl-1,3,2-dioxaborolan-2-yl)phenyl)-5-(trifluoromethyl)-1H-pyrazole-4-carboxylate

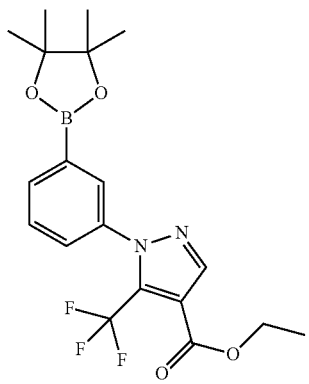 [SMILES: CCOC(=O)c1cnn(-c2cccc(B3OC(C)(C)C(C)(C)O3)c2)c1C(F)(F)F]

To a mixture of Intermediate 1-2-2 (1.04 g, 4.09 mmol), KOAc (0.730 g, 7.44 mmol), and bis(pinacolato)diboron (0.792 g, 3.12 mmol) in dioxane (18.6 ml) was added chloro(2-dicyclohexylphosphino-2',6'-dimethoxy-1,1'-biphenyl)[2-(2-aminoethylphenyl)]palladium(II)-methyl-t-butyl ether adduct (CAS#1028206-58-7, 0.125 g, 0.186 mmol). The mixture was stirred at 100° C. for 90 min, and then cooled to room temperature. Celite® was added to the reaction mixture and the solvent was removed under reduced pressure. The resulting residue was purified by silica gel flash column chromatography (0-25% EtOAc/heptane) to afford the title compound. ¹H NMR (400 MHz, CDCl₃) δ 8.10 (d, J=0.8 Hz, 1H), 7.93 (ddd, J=6.8, 2.0, 1.1 Hz, 1H), 7.86 (d, J=2.1 Hz, 1H), 7.55-7.45 (m, 2H), 4.38 (q, J=7.1 Hz, 2H), 1.39 (t, J=7.1 Hz, 3H), 1.34 (s, 12H).

Intermediate 1-5. Ethyl 1-(6-bromopyridin-2-yl)-5-methyl-1H-pyrazole-4-carboxylate

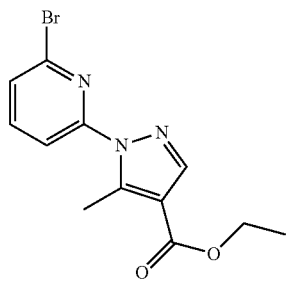 [SMILES: CCOC(=O)c1cnn(-c2cccc(Br)n2)c1C]

A mixture of 2-bromo-6-hydrazinylpyridine (5.04 g, 26.8 mmol) and ethyl 2-acetyl-3-(dimethylamino)acrylate (CAS#51145-57-4; 4.96 g, 26.8 mmol) in EtOH (81 mL) was heated to 70° C. for 1.5 h. The reaction mixture was then allowed to cool to room temperature during which time a precipitate formed. Water (80 mL) was then added to the mixture and the resulting heterogeneous mixture was filtered. The filter cake was washed with water and dried under reduced pressure to yield the title compound. MS (ESI+) m/z 310.1 (M+H).

Intermediate 2-1

Intermediate 2-1-A. tert-Butyl 4-(4-hydroxy-3-methylphenyl)-5,6-dihydropyridine-1(2H)-carboxylate

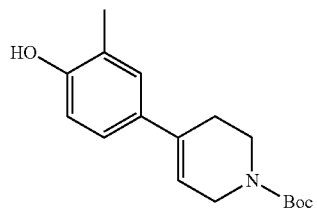 [SMILES: Cc1cc(C2=CCN(C(=O)OC(C)(C)C)CC2)ccc1O]

To a suspension of 4-bromo-2-methyl phenol (CAS#2362-12-1, 5 g, 26.7 mmol), tert-butyl 4-(4,4,5,5-tetramethyl-1,3,2-dioxaborolan-2-yl)-5,6-dihydropyridine-1 (2H)-carboxylate (CAS#286961-14-6, 8.27 g, 26.7 mmol), and K₃PO₄ (2 M in H₂O, 26.7 mL, 53.5 mmol) in acetonitrile (54 mL) was added PdCl₂(dppf) dichloromethane adduct (1.09 g, 1.33 mmol). The mixture was then stirred at 80° C. for 3 h, and then cooled to rt. Celite® was added to the reaction mixture and the solvent was removed under reduced pressure. The resulting residue was purified by silica gel flash column chromatography (heptane/EtOAc=1/0 to 1/1) to afford the title compound. MS (ESI+) m/z 290.1 (M+H).

Intermediate 2-1. tert-Butyl 4-(4-hydroxy-3-methylphenyl)piperidine-1-carboxylate

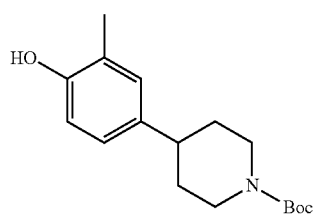 [SMILES: Cc1cc(C2CCN(C(=O)OC(C)(C)C)CC2)ccc1O]

A mixture of Intermediate 2-1-A (4.4 g, 15.21 mmol) and Pd/C (5%, 0.8 g) in MeOH (50 mL) was stirred under an H₂ atmosphere at rt for 2 h. The reaction mixture was then filtered through a plug of Celite®. The filtrate was then concentrated to furnish the title compound directly. MS (ESI−) m/z 290.2 (M−H).

Intermediate 2-2

Intermediate 2-2-A. tert-Butyl 4-(2-ethyl-4-hydroxyphenyl)-5,6-dihydropyridine-1(2H)-carboxylate

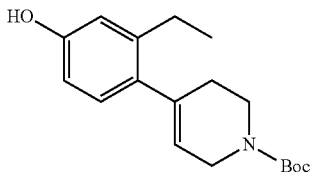

To a mixture of 4-chloro-3-ethylphenol (CAS#59-50-7, 3 g, 19.16 mmol), tert-butyl 4-(4,4,5,5-tetramethyl-1,3,2-dioxaborolan-2-yl)-5,6-dihydropyridine-1(2H)-carboxylate (7.70 g, 24.90 mmol), chloro(2-dicyclohexylphosphino-2',6'-dimethoxy-1,1'-biphenyl)[2-(2-aminoethylphenyl)]palladium(II) methyl-t-butylether adduct (CAS#1028206-58-7, 0.644 g, 0.958 mmol) in DMF (96 mL) was added 2 M aq. potassium phosphate (28.7 mL, 57.5 mmol). The mixture was stirred at 110° C. for 1 h, and then cooled to rt. The reaction mixture was diluted with EtOAc and $H_2O$. The organic layer was then separated, and dried over $Na_2SO_4$, filtered, and then concentrated. The resulting residue was purified by silica gel flash column chromatography (heptane/EtOAc=1/0 to 6/4) to afford the title compound. MS (ESI+) m/z 248.2 (M-tBu+2H).

Intermediate 2-2. tert-Butyl 4-(2-ethyl-4-hydroxyphenyl)piperidine-1-carboxylate

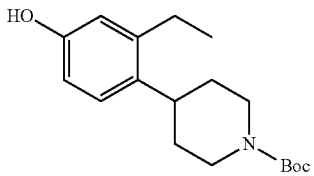 [SMILES: CCc1cc(O)ccc1C1CCN(C(=O)OC(C)(C)C)CC1]

A mixture of Intermediate 2-2-A (5.4 g, 17.80 mmol) and 10% Pd/C (1.894 g) in MeOH (250 mL) was stirred under an $H_2$ atmosphere at rt for 1 h. The reaction mixture was then filtered through a plug of Celite® which was then washed with MeOH. The filtrate was then concentrated to furnish the title compound directly. MS (ESI+) m/z 250.2 (M-tBu+2H).

Intermediate 2-3. 2-Methyl-4-(piperidin-4-yl)phenol

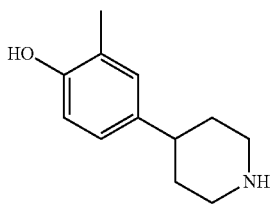

To a solution of Intermediate 2-1 (3.98 g, 13.66 mmol) in $CH_2Cl_2$ (137 mL) at 0° C. was added TFA (12.6 mL, 164 mmol). The mixture was then stirred for 1.5 h, and then concentrated to dryness to furnish the title compound. MS (ESI+) m/z 192.1 (M+H).

Intermediate 2-4. Cyclopropyl(4-(4-hydroxy-3-methylphenyl)piperidin-1-yl)methanone

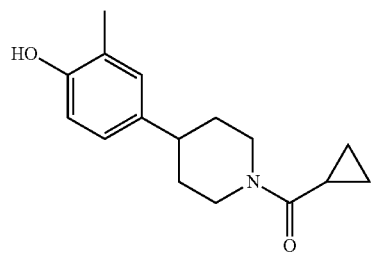 [SMILES: Cc1cc(C2CCN(C(=O)C3CC3)CC2)ccc1O]

To a solution of Intermediate 2-3 (2.6 g, 13.59 mmol) in $CH_2Cl_2$ (68 mL) at 0° C. was added DIPEA (9.5 mL, 54.4 mmol), followed by cyclopropanecarbonyl chloride (2.47 mL, 27.2 mmol). The mixture was then stirred at 0° C. for 1 h, and then quenched with $H_2O$. The mixture was then extracted with $CH_2Cl_2$. The organic layer was then concentrated. The residue was treated with $K_2CO_3$ (9.39 g, 68 mmol) in MeOH (68 mL) at rt with stirring for 2 h. The mixture was then diluted with $CH_2Cl_2$ and $H_2O$ and passed through an ISOLUTE® Phase Separator. The resulting organic layer was then concentrated to furnish the title compound. MS (ESI+) m/z 260.1 (M+H).

Intermediate 2-5

The following compounds were prepared with similar methods as described above using the appropriate starting materials, specifically Intermediate 2-5-1 can be prepared starting from Intermediate 2-2 in a fashion similar to the method to go from Intermediate 2-1 to Intermediate 2-4. Intermediate 2-5-2 can be accessed starting from 4-bromo-2-ethylphenol in a manner similar to the procedures outlined to access Intermediate 2-1-A and then the procedures to access to Intermediate 2-4.

| Intermediate | Structure/Chemical Name | Starting material(s) | Analytical data |
|---|---|---|---|
| 2-5-1 | Cyclopropyl(4-(2-ethyl-4-hydroxyphenyl)piperidin-1-yl)methanone | Intermediate 2-2 and cyclopropanecarbonyl chloride | MS (ESI+) m/z 274.3 (M + H) |
| 2-5-2 | Cyclopropyl(4-(3-ethyl-4-hydroxyphenyl)piperidin-1-yl)methanone | 4-bromo-2-ethylphenol (CAS# 18980-21-7) and cyclopropane carbonyl chloride | MS (ESI+) m/z 274.3 (M + H) |

Intermediate 3

Intermediate 3-1. tert-Butyl 6-hydroxy-3,4-dihydroisoquinoline-2(1H)-carboxylate

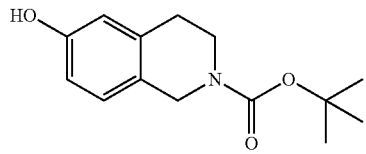 [SMILES: CC(C)(C)OC(=O)N1CCc2cc(O)ccc2C1]

To a solution of 1,2,3,4-tetrahydroisoquinolin-6-ol hydrobromide (CAS #59839-23-5, 0.5 g, 2.17 mmol) in MeOH (20 mL) was added triethylamine (0.73 mL, 5.22 mmol) followed by di-tert-butyl dicarbonate (0.87 mL, 3.76 mmol) at rt. The mixture was then stirred at rt for 16 h. The reaction mixture was concentrated, and then diluted with EtOAc and water. The organic phase was then separated. The organic layer was then washed with 1 N HCl, water, and sat'd. NaHCO$_3$. The organic layer was dried over Na$_2$SO$_4$, filtered, and then concentrated. The resulting residue was purified by silica gel flash column chromatography (0-100% EtOAc in heptane) to afford the title compound. $^1$H NMR (400 MHz, CDCl$_3$) δ 6.98 (d, J=8.2 Hz, 1H), 6.68 (dd, J=2.6, 8.3 Hz, 1H), 6.62 (d, J=2.6 Hz, 1H), 4.62 (br. s., 1H), 4.50 (s, 2H), 3.62 (t, J=5.9 Hz, 2H), 2.78 (t, J=5.9 Hz, 2H), 1.50 (s, 9H).

Intermediate 3-2. 2-(Pyridin-2-ylmethyl)-1,2,3,4-tetrahydroisoquinolin-6-ol

To a mixture of 1,2,3,4-tetrahydroisoquinolin-6-ol hydrobromide (CAS #59839-23-5, 2 g, 8.69 mmol) and TEA (4.85 mL, 34.8 mmol) in DCM (87 ml) at 0° C. was added 2-(bromomethyl)pyridine hydrobromide (CAS #31106-82-8, 2.42 g, 9.56 mmol) portionwise. The mixture was then stirred at rt for 1 h, and then diluted with 1:1 water/saturated sodium bicarbonate and DCM. The mixture was then passed through an ISOLUTE® Phase Separator. The organic phase was then concentrated. The resulting residue was purified by flash column chromatography (acetone/heptane, 0-50%) to afford title compound. MS (ESI+) m/z 241.1 (M+H).

Intermediate 4

Intermediate 4-A. 2-Bromocyclohex-1-enecarbaldehyde

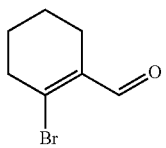

PBr$_3$ (CAS #7789-60-8, 27.4 mL, 290 mmol) was added to a mixture of chloroform (160 mL) and DMF (25 mL, 319 mmol) at 0° C. The mixture was then stirred at 0° C. for 1 h. To the solution, cyclohexanone (CAS #108-94-1, 10 mL, 97 mmol) was added dropwise. The resulting mixture was allowed to slowly warm to rt, and then stir for 16 h. The reaction mixture was then poured into ice cold aqueous NaOAc (47.6 g in 150 mL). The pH was adjusted to ~5 using 5 N NaOH and the chloroform was removed under the reducing pressure. The aqueous layer was extracted with heptane. The combined organic extracts were washed with water and brine. The organic layer was then dried over sodium sulfate, filtered, and then concentrated to furnish the title compound. $^1$H NMR (400 MHz, CDCl$_3$) δ 10.05 (s, 1H), 2.77 (tt, J=6.3, 2.3 Hz, 2H), 2.30 (tt, J=5.8, 2.3 Hz, 2H), 1.84-1.66 (m, 4H).

Intermediate 4-B.
(2-Bromocyclohex-1-en-1-yl)methanol

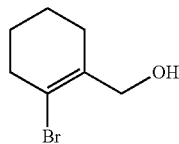

NaBH$_4$ (2.17 g, 57.3 mmol) was added slowly in portions over 15 min to a methanol solution of Intermediate 4-A (8.33 g, 44.1 mmol) at 0° C. The reaction was stirred at 0° C. for 2.5 h. Acetone and water were added and mixture was partially concentrated. The aqueous phase was acidified with 0.1 N HCl and extracted with EtOAc. The organic phase was washed with water and brine. The organic phase was then dried over sodium sulfate, filtered and concentrated to give the title compound. $^1$H NMR (400 MHz, DMSO-d$_6$) δ 4.80 (t, J=5.7 Hz, 1H), 4.03 (dtd, J=5.9, 1.6, 0.8 Hz, 2H), 2.43 (tq, J=5.9, 2.0 Hz, 2H), 2.21-2.12 (m, 2H), 1.68-1.54 (m, 4H).

Intermediate 4. ((2-Bromocyclohex-1-en-1-yl)methoxy)(tert-butyl)dimethylsilane

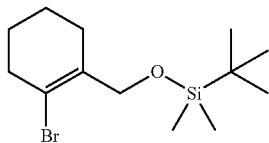 [SMILES: CC(C)(C)[Si](C)(C)OCC1=C(Br)CCCC1]

TBSCl (6.1 g, 40.5 mmol) was added to a DMF (30 mL) solution of Intermediate 4-B (7.03 g, 36.8 mmol) and imidazole (2.88 g, 43.3 mmol) at rt. The resulting solution was stirred at rt for 16 h. The reaction mixture was diluted with water, and then extracted with a 1/1 mixture of EtOAc/heptane. The organic phase was washed with water and brine. The organic phase was then dried over sodium sulfate, filtered, and concentrated to furnish the title compound. $^1$H NMR (400 MHz, DMSO-d$_6$) δ 4.18 (m, 2H), 2.41-2.35 (m, 2H), 2.15-2.06 (m, 2H), 1.63-1.49 (m, 2H), 1.21-1.14 (m, 2H), 0.81 (d, J=5.1 Hz, 9H), −0.06 (s, 6H).

Intermediate 5

Intermediate 5-1-A.
2-(Hydroxymethyl)cyclohex-1-en-1-yl trifluoromethanesulfonate

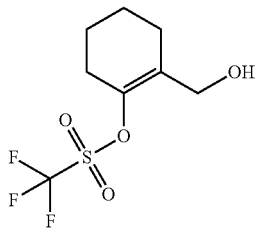 [SMILES: O=S(=O)(OC1=C(CO)CCCC1)C(F)(F)F]

DIBAL-H (1 M in heptane, 34.7 mL, 34.7 mmol) was added dropwise to a DCM (50 mL) solution of ethyl 2-(((trifluoromethyl)sulfonyl)oxy)cyclohex-1-enecarboxylate (CAS #122135-83-5, 5 g, 16.54 mmol) at −78° C. The mixture was stirred for 1 h at −78° C., and then stirred at rt for 16 h. The reaction was quenched with 1:1 water/saturated Rochelle's salt solution. The mixture was then stirred at rt for 1 h. The mixture was extracted with DCM. The organic extracts were dried over sodium sulfate, filtered, and then concentrated. The resulting residue was purified by silica gel flash column chromatography (0-50% EtOAc in heptane) to afford the title compound. MS (ESI+) m/z 243.0 (M-OH)$^+$.

Intermediate 5-1. 2-((4-(1-(Cyclopropanecarbonyl)piperidin-4-yl)-2-methylphenoxy)methyl)cyclohex-1-en-1-yl trifluoromethanesulfonate

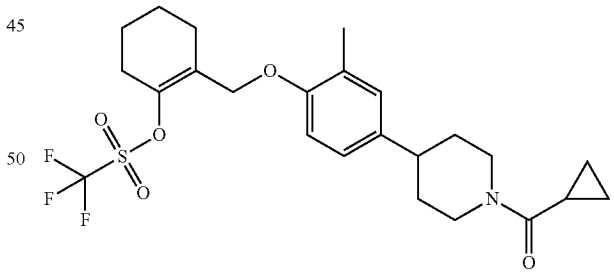

DIAD (95 μl, 0.486 mmol) was added dropwise over 5 min to a 0° C. THF (1.8 mL) solution of Intermediate 2-4 (126 mg, 0.486 mmol), triphenylphosphine (127 mg, 0.486 mmol) and Intermediate 5-1-A (115 mg, 0.442 mmol). The resulting mixture was stirred at 0° C. for 20 min, then stirred at rt for 3.5 h, and then diluted with ca. 2 mL of heptane. The mixture was purified by silica gel flash column chromatography (0-20% EtOAc/heptane) to afford the title compound. MS (ESI+) m/z 502.3 (M+H).

Intermediate 5-2. tert-Butyl 4-(3-methyl-4-((2-(((trifluoromethyl)sulfonyl)oxy)cyclohex-1-en-1-yl)methoxy)phenyl)piperidine-1-carboxylate

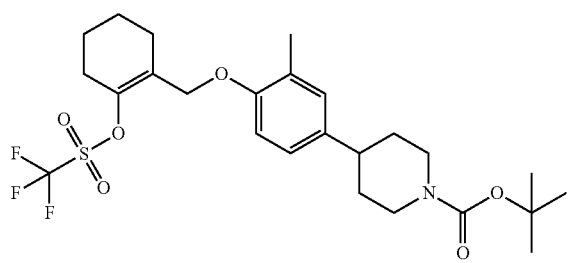 [SMILES: Cc1cc(C2CCN(C(=O)OC(C)(C)C)CC2)ccc1OCC1=C(OS(=O)(=O)C(F)(F)F)CCCC1]

The title compound was synthesized from Intermediate 5-1-A and Intermediate 2-1 in a similar manner as described for Intermediate 5-1. MS (ESI+) m/z 434.2 (M-t-Boc+2H).

Intermediate 6

Intermediate 6-A. (±)-Ethyl 4-methyl-2-(((trifluoromethyl)sulfonyl)oxy)cyclohex-1-enecarboxylate

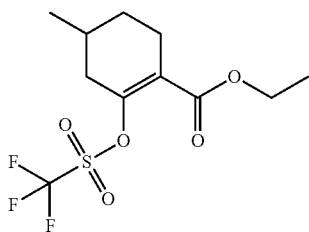 [SMILES: CCOC(=O)C1=C(OS(=O)(=O)C(F)(F)F)CC(C)CC1]

NaH (0.56 g, 14.1 mmol, 60% in mineral oil) was added to a DCM (60 mL) solution of ethyl 4-methyl-2-oxocyclohexanecarboxylate (CAS #13537-82-1, 2.0 g, 10.9 mmol) at 0° C. The suspension was allowed to warm to rt and stir for 10 min. The reaction was then cooled to −78° C. At that time triflic anhydride (2.4 mL, 14.1 mmol) was added. The reaction mixture was allowed to gradually warm to rt. After 1 hour at room temperature, the reaction was quenched by the slow addition of 10% citric acid solution. The mixture was then diluted with DCM and water. The layers were mixed and then separated. The aqueous layer was further extracted with DCM. The combined organic layers were then dried over $Na_2SO_4$ and filtered. The solvent was removed under reduced pressure to give the title compound, which was used without further purification. MS (ESI+) m/z 317.0 (M+H).

Intermediate 6-B. (±)-2-(Hydroxymethyl)-5-methylcyclohex-1-en-1-yl trifluoromethanesulfonate

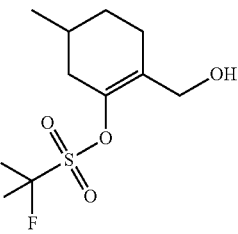

DIBAL-H (23.6 mL, 23.6 mmol, 1 M heptane) was added dropwise to a solution of Intermediate 6-A (3.4 g, 10.8 mmol) in DCM (100 mL) at −78° C. After 15 min the solution was removed from the cold bath and allowed to warm gradually to rt. After stirring at rt for 0.5 h the reaction was quenched by the addition of 1 mL of water, 1 mL of 15% NaOH, and 2.5 mL of water. The mixture was vigorously stirred for 30 min before $MgSO_4$ was added. Stirring continued for 15 min and then the mixture was filtered over Celite®. The solvent was removed under reduced pressure to give the title compound, which was taken to the next step without further purification. $^1$H NMR (400 MHz, $CDCl_3$) δ 4.29-4.12 (m, 2H), 2.48-2.22 (m, 3H), 2.08-1.96 (m, 1H), 1.95-1.82 (m, 1H), 1.81-1.71 (m, 1H), 1.28 (m, 2H), 1.03 (d, J=6.6 Hz, 3H).

Intermediate 6. (±)-2-(((tert-Butyldimethylsilyl)oxy)methyl)-5-methylcyclohex-1-en-1-yl trifluoromethanesulfonate

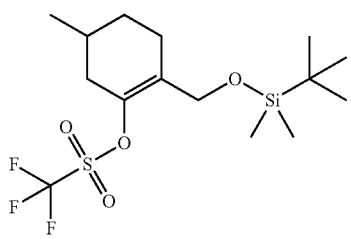 [SMILES: CC1CCC(CO[Si](C)(C)C(C)(C)C)=C(OS(=O)(=O)C(F)(F)F)C1]

To a solution of Intermediate 6-B (2.76 g, 10.1 mmol) and imidazole (1.71 g, 25.2 mmol) in DCM (50 mL) was added TBSCl (1.59 g, 10.6 mmol). After 1.5 h the reaction was diluted with DCM and washed with 2% citric acid solution. The organic layer was further washed with brine before being dried over sodium sulfate and filtered. The solvent was removed under reduced pressure to give the title compound, which was used without further purification. $^1$H NMR (400 MHz, $CDCl_3$) δ 4.33-4.20 (m, 2H), 2.42-2.17 (m, 3H), 2.06-1.98 (m, 1H), 1.93-1.81 (m, 1H), 1.78-1.69 (m, 1H), 1.34-1.18 (m, 1H), 1.02 (d, J=6.6 Hz, 3H), 0.90 (d, J=0.8 Hz, 9H), 0.07 (d, J=0.7 Hz, 6H).

Intermediate 7

Intermediate 7-A. Methyl 3-oxooct-6-enoate

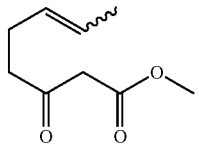

Methyl acetoacetate (CAS #105-45-3, 1.85 mL, 17.2 mmol) was added dropwise to a suspension of NaH (0.76 g, 18.9 mmol, 60% in mineral oil) and THF (60 mL) at 0° C. After 10 min n-BuLi (7.58 mL, 18.9 mmol, 2.5 M in heptane) was added dropwise. After an additional 10 min crotonyl bromide (CAS #55600-70-9, 1.77 mL, 17.2 mmol) was added and the reaction was allowed to slowly warm to rt. After 2 h the reaction was quenched with 1 M HCl and the mixture was extracted with Et$_2$O (200 mL). The organic layer was then dried over MgSO$_4$, filtered, and concentrated under reduced pressure. The residue was purified by silica gel flash column chromatography (5% EtOAc/heptane) to give the title compound as a mixture of E- and Z-isomers. MS (ESI+) m/z 171.1 (M+H).

Intermediate 7-B. (±)-Methyl 2-methyl-6-oxocyclohexanecarboxylate

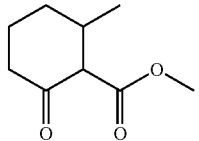

A mixture of Intermediate 7-A (4.35 g, 25.6 mmol), ytterbium(III) trifluoromethanesulfonate (CAS#54761-04-5, 4.76 g, 7.67 mmol), and dichlorobis(acetonitrile)palladium (II) (CAS#14592-56-4, 0.66 g, 2.56 mmol) in dioxane (250 mL) was heated at 50° C. for 30 h. At that point the solvent was removed under reduced pressure. The residue was passed through a silica gel plug, eluting with 30% EtOAc/heptane. The solvent was then removed under reduced pressure to give the title compound which was used without further purification. MS (ESI+) m/z 171.1 (M+H).

Intermediate 7-C. (±)-Methyl 6-methyl-2-(((trifluoromethyl)sulfonyl)oxy)cyclohex-1-enecarboxylate

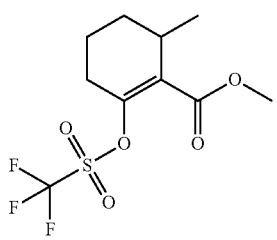 [SMILES: COC(=O)C1=C(OS(=O)(=O)C(F)(F)F)CCCC1C]

To a solution of Intermediate 7-B (1.00 g, 5.88 mmol) in DCM (30 mL) at 0° C., NaH (0.305 g, 7.64 mmol, 60% in mineral oil) was added. The suspension was allowed to warm to rt and stir for 10 min. The reaction was then cooled to −78° C. At that time triflic anhydride (1.29 mL, 14.1 mmol) was then added. The reaction mixture was then allowed to gradually warm to rt. After 1 hour at that temperature, the reaction was quenched with the slow addition of 10% citric acid solution. The mixture was then diluted with DCM and water. The layers were mixed and then separated. The aqueous layer was further extracted with DCM. The combined organic layers were then dried over Na$_2$SO$_4$ and filtered. The solvent was removed under reduced pressure. The resulting residue was purified by silica gel flash column chromatography (0-10% EtOAc/heptane) to give the title compound. $^1$H NMR (400 MHz, CDCl$_3$) δ 3.74 (s, 3H), 2.91-2.78 (m, 1H), 2.40-2.21 (m, 2H), 1.85-1.73 (m, 1H), 1.73-1.62 (m, 2H), 1.45-1.35 (m, 1H), 1.02 (d, J=6.9 Hz, 3H).

Intermediate 7-D. (±)-2-(Hydroxymethyl)-3-methylcyclohex-1-en-1-yl trifluoromethanesulfonate

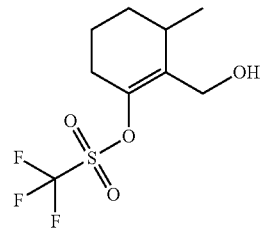 [SMILES: CC1CCCC(OS(=O)(=O)C(F)(F)F)=C1CO]

Intermediate 7-C (5.1 g, 16.9 mmol) was dissolved in DCM (170 mL). The solution was cooled to −78° C. under a nitrogen atmosphere. A solution of DIBAL-H (35.4 mL, 35.4 mmol, 1 M) was added to the cool solution. The reaction was allowed to slowly warm to rt over 1 h, at which point the reaction showed complete conversion (TLC, 25% EtOAc/heptane, KMnO$_4$ stain). The reaction was then quenched with the addition of 2.1 mL of water with vigorous stirring at rt for 15 min. Following this, 2.1 mL of 15% aqueous NaOH was added. The reaction was agitated further with vigorous stirring until solids formed. The solids were removed by filtration and the filtrate was concentrated to afford the title compound which was used without further purification. $^1$H NMR (400 MHz, CD$_3$OD) δ 4.40 (d, J=12.8 Hz, 1H), 4.05 (d, 1H), 2.62-2.76 (m, 1H), 2.30-2.39 (m, 2H), 1.64-1.95 (m, 3H), 1.37-1.50 (m, 1H), 1.15 (d, J=7.0 Hz, 3H).

Intermediate 7. (±)-2-(((tert-Butyldimethylsilyl)oxy)methyl)-3-methylcyclohex-1-en-1-yl trifluoromethanesulfonate

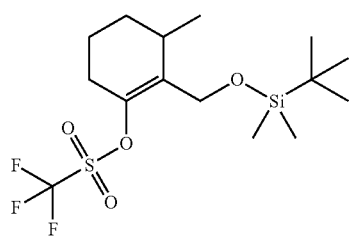 [SMILES: CC1CCCC(OS(=O)(=O)C(F)(F)F)=C1CO[Si](C)(C)C(C)(C)C]

Intermediate 7-D (6.0 g, 21.9 mmol) was dissolved in DMF (220 mL). To this solution was added imidazole (1.71 g, 25.2 mmol) and TBSCl (3.63 g, 24.1 mmol) at rt. The resulting solution was stirred at rt for 3 h. The reaction was monitored by TLC with a 25% solution of EtOAc in heptane and stained with $KMnO_4$. The reaction was then filtered through a pad of Celite® eluting with 25% EtOAc-heptane. The resulting solution was then concentrated. To the residue was added water and it was extracted with ca. 1/1 mixture of EtOAc/heptane, the organic phase was washed with dilute NaCl solution and then dried over sodium sulfate. The solution was filtered, and concentrated to afford the title compound. $^1$H NMR (400 MHz, $CD_3OD$) δ 4.40 (d, J=12.4 Hz, 1H), 4.07-4.14 (m, 1H), 2.55-2.67 (m, 1H), 2.18-2.30 (m, 2H), 1.72-1.85 (m, 1H), 1.57-1.72 (m, 2H), 1.30-1.41 (m, 1H), 1.06 (d, J=7.0 Hz, 3H), 0.83 (s, 9H), 0.01 (d, J=5.2 Hz, 6H).

Intermediate 8

Intermediate 8-A. Methyl 7-methyl-3-oxooct-6-enoate

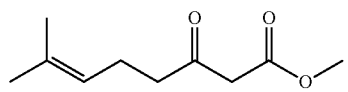

Methyl acetoacetate (CAS #105-45-3, 7.43 ml, 68.9 mmol) was added dropwise to a suspension of NaH (3.03 g, 76 mmol) and THF (200 ml) at 0° C. After 10 min n-BuLi (30.3 ml, 76 mmol) was added dropwise. After an additional 10 min 1-bromo-3-methylbut-2-ene (CAS #870-63-3, 8.02 ml, 68.9 mmol) was added and the reaction was allowed to slowly warm to rt. After 2 h the reaction was quenched with 1 M HCl and the mixture was extracted with $Et_2O$ (200 mL). The organic layer was then dried over $MgSO_4$, filtered, and concentrated under reduced pressure. The resulting residue was purified by silica gel flash column chromatography (5% EtOAc/heptane) to give the title compound. MS (ESI+) m/z 185.2 (M+H).

Intermediate 8-B. Methyl 2,2-dimethyl-6-oxocyclohexanecarboxylate

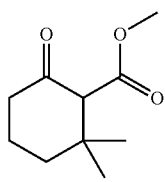

A solution of Intermediate 8-A (12.5 g, 67.8 mmol), ytterbium(III) trifluoromethanesulfonate (12.5 g, 20.4 mmol), and dichlorobis(acetonitrile)palladium(II) (1.76 g, 6.78 mmol) in dioxane (200 mL) was heated at 50° C. After 30 h the solvent was removed under reduced pressure. The residue was passed through a silica gel plug, eluting with 30% EtOAc/heptane. The solvent was then removed under reduced pressure to afford the title compound. $^1$H NMR (400 MHz, $CD_3OD$) δ 3.24-3.37 (m, 3H), 2.30-2.58 (m, 2H), 1.86-1.98 (m, 2H), 1.57-1.85 (m, 3H), 1.05 (d, J=15.4 Hz, 6H).

Intermediate 8-C. Methyl 6,6-dimethyl-2-(((trifluoromethyl)sulfonyl)oxy)cyclohex-1-enecarboxylate

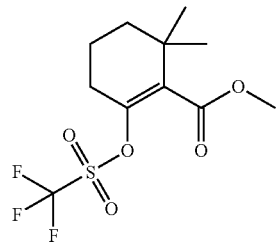 [SMILES: COC(=O)C1=C(OS(=O)(=O)C(F)(F)F)CCCC1(C)C]

Intermediate 8-B (6.3 g, 34.2 mmol) was dissolved in DCM (340 mL) and NaH (1.43 g, 35.9 mmol, 60% in mineral oil) was added. The mixture was stirred at rt for 30 min. It was then cooled to −78° C. Triflic anhydride (5.78 mL, 34.2 mmol) was then added and the reaction was allowed to slowly warm to rt. The reaction was diluted with water and stirred for 10 min. The mixture was extracted with DCM and the organic layer was dried over magnesium sulfate, filtered and concentrated. The resulting residue was purified by silica gel flash column chromatography (0-100% EtOAc/heptane) to afford the title compound. MS (ESI+) m/z 317.2 (M+H).

Intermediate 8-D. 2-(Hydroxymethyl)-3,3-dimethylcyclohex-1-en-1-yl trifluoromethanesulfonate

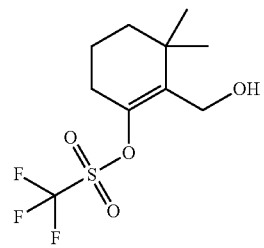 [SMILES: CC1(C)CCCC(OS(=O)(=O)C(F)(F)F)=C1CO]

Intermediate 8-C (7.2 g, 22.8 mmol) was dissolved in DCM (230 mL) and cooled to −78° C. DIBAL-H (50 mL, 50 mmol, 1 M) was added and the reaction was allowed to return to rt and stir overnight. Then, 0.17 mL of water was added. After stirring for 5 min, 0.17 mL of 15% (aq) NaOH was added. Stirring continued until solids form. The reaction mixture was then filtered and concentrated under reduced pressure. The residue was then purified by silica gel flash column chromatography (0-100% EtOAc/heptane) to afford the title compound. $^1$H NMR (400 MHz, $CD_3OD$) δ 4.20-4.25 (m, 2H), 2.34-2.41 (m, 2H), 1.75-1.86 (m, 2H), 1.46-1.55 (m, 2H), 1.17 (s, 6H).

Intermediate 8. 2-(((tert-Butyldimethylsilyl)oxy)methyl)-3,3-dimethylcyclohex-1-en-1-yl trifluoromethanesulfonate

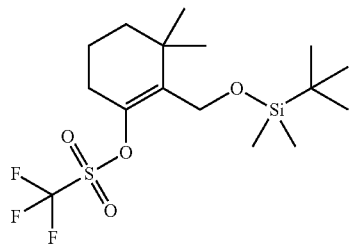 [SMILES: CC1(C)CCCC(OS(=O)(=O)C(F)(F)F)=C1CO[Si](C)(C)C(C)(C)C]

Intermediate 8-D (6.7 g, 23.2 mmol) was dissolved in DMF (200 mL) and imidazole (1.82 g, 26.7 mmol) was added. TBSCl (3.85 g, 25.6 mmol) was then added. The reaction was stirred at rt for 16 h. The reaction was monitored by TLC (25% EtOAc/heptane stained with KMnO$_4$). The reaction was then filtered through a pad of Celite® eluting with 25% EtOAc/heptane and then concentrated. Water was added and extraction done with 1:1 EtOAc/heptane. The organic phase was washed with water then brine before being dried over sodium sulfate. Filtration followed by concentration under reduced pressure afforded the title compound. $^1$H NMR (400 MHz, Methanol-d$_4$) δ 4.30 (t, J=1.0 Hz, 2H), 2.36 (t, J=6.4 Hz, 2H), 1.77-1.88 (m, 2H), 1.46-1.54 (m, 2H), 1.19 (d, J=2.0 Hz, 6H), 0.91 (d, J=1.6 Hz, 9H), 0.10 (s, 6H).

Intermediate 9

Intermediate 9-A. Ethyl 1-(6-(2-(((tert-butyldimethylsilyl)oxy)methyl)cyclohex-1-en-1-yl)pyridin-2-yl)-5-(trifluoromethyl)-1H-pyrazole-4-carboxylate

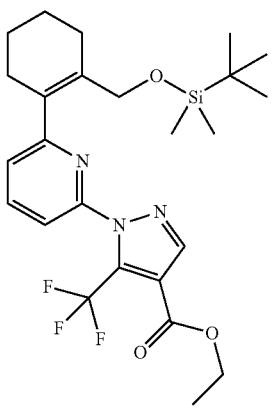 [SMILES: CCOC(=O)c1cnn(-c2cccc(C3=C(CO[Si](C)(C)C(C)(C)C)CCCC3)n2)c1C(F)(F)F]

A suspension of Intermediate 1-1 (5.00 g, 13.73 mmol), bis(pinacolato)diboron (CAS #73183-34-3 (3.84 g, 15.10 mmol), potassium acetate (2.022 g, 20.60 mmol) and chloro (2-dicyclohexylphosphino-2',6'-dimethoxy-1,1'-biphenyl)[2-(2-aminoethylphenyl)]palladium(II) methyl-t-butylether adduct (CAS #1028206-58-7) (0.185 g, 0.275 mmol) in dioxane (35 mL) was stirred at 110° C. for 3.5 h. To the mixture was then added a solution of Intermediate 4 (5.87 g, 19.22 mmol) in dioxane (14 mL), followed by chloro(2-dicyclohexylphosphino-2',6'-dimethoxy-1,1'-biphenyl)[2-(2-aminoethylphenyl)]palladium(II) methyl-t-butylether adduct (0.462 g, 0.687 mmol) and Na$_2$CO$_3$ (1 M aq., 13.73 mL, 27.5 mmol). The mixture was stirred at 110° C. for 18 h. The reaction mixture was diluted with EtOAc and water. The organic phase was separated and washed with water and then brine. The combined extracts were then dried over sodium sulfate, filtered, and concentrated. The resulting residue was purified by silica gel flash column chromatography (0-10% EtOAc in heptane) to afford the title compound. MS (ESI+) m/z 510.3 (M+H).

Intermediate 9. Ethyl 1-(6-(2-(hydroxymethyl)cyclohex-1-en-1-yl)pyridin-2-yl)-5-(trifluoromethyl)-1H-pyrazole-4-carboxylate

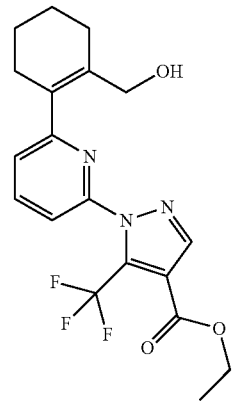 [SMILES: CCOC(=O)c1cnn(-c2cccc(C3=C(CO)CCCC3)n2)c1C(F)(F)F]

TBAF (1 M in THF 2.81 mL, 2.81 mmol) was added to a THF solution of Intermediate 9-A (1.365 g, 2.68 mmol) at rt. The reaction mixture was stirred at rt for 1 h, and then diluted with EtOAc and water. The organic phase was separated and washed with water and then brine. The combined extracts were then dried over sodium sulfate, filtered, and concentrated. The resulting residue was purified by silica gel flash column chromatography (100% heptane to 100% EtOAc) to afford the title compound. MS (ESI+) m/z 396.2 (M+H).

Intermediate 10. (±)-tert-Butyl 4-(2-ethyl-4-((6-methyl-2-(((trifluoromethyl)-sulfonyl)oxy)cyclohex-1-en-1-yl)methoxy)phenyl)piperidine-1-carboxylate

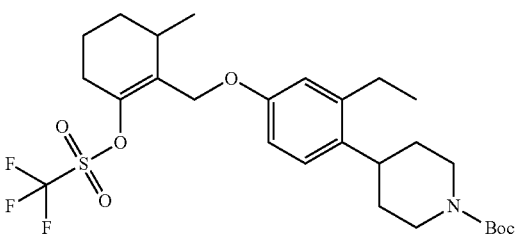 [SMILES: CCc1cc(OCC2=C(OS(=O)(=O)C(F)(F)F)CCCC2C)ccc1C1CCN(C(=O)OC(C)(C)C)CC1]

DIAD (6.43 mL, 33.1 mmol) was added dropwise over 2.5 min to a 0° C. THF (118 mL) solution of Intermediate 2-2 (11.8 g, 38.6 mmol), triphenylphosphine (8.68 g, 33.1 mmol) and Intermediate 7-D (8.25 g, 30.1 mmol). The resulting mixture was stirred at room temperature for 20 h. The reaction mixture was diluted with EtOAc. The mixture was washed with water, dried over $Na_2SO_4$, filtered, and then concentrated. The resulting residue was purified by silica gel flash column chromatography (0-50% EtOAc/heptane) to afford the title compound. MS (ESI+) m/z 506.3 $(M-tBu+2H)^+$.

Intermediate 11

Intermediate 11-A. (±)-Methyl 5-methyl-2-(((trifluoromethyl)sulfonyl)oxy)cyclopent-1-enecarboxylate

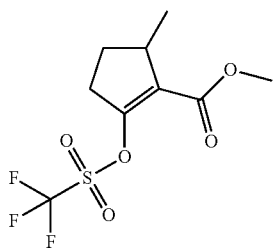 [SMILES: COC(=O)C1=C(OS(=O)(=O)C(F)(F)F)CCC1C]

The title compound was synthesized from (±)-methyl 2-methyl-5-oxocyclopentanecarboxylate (*J. Org. Chem.* 5364-5366 (1983), CAS #18067-33-9) by a similar method as described for Intermediate 6-A except for using DIPEA in the place of NaH. $^1$H NMR (400 MHz, CDCl$_3$) δ 3.80 (s, 3H), 3.19-3.04 (m, 1H), 2.86-2.76 (m, 1H), 2.69-2.60 (m, 1H), 2.30-2.19 (m, 1H), 1.64-1.54 (m, 1H), 1.21 (d, J=6.8 Hz, 3H).

Intermediate 11-B. (±)-2-(Hydroxymethyl)-3-methylcyclopent-1-en-1-yl trifluoromethanesulfonate

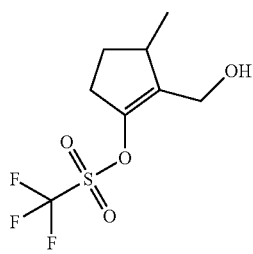 [SMILES: CC1CCC(OS(=O)(=O)C(F)(F)F)=C1CO]

The title compound was synthesized starting from (±)-methyl 5-methyl-2-(((trifluoromethyl)sulfonyl)oxy)cyclopent-1-enecarboxylate analogously to the method described for Intermediate 6-B. $^1$H NMR (400 MHz, CDCl$_3$) δ 3.80 (s, 3H), 3.18-3.03 (m, 1H), 2.86-2.76 (m, 1H), 2.69-2.59 (m, 1H), 2.30-2.19 (m, 1H), 1.64-1.50 (m, 1H), 1.21 (d, J=6.8 Hz, 3H).

Intermediate 11. (±)-2-(((tert-Butyldimethylsilyl)oxy)methyl)-3-methylcyclopent-1-en-1-yl trifluoromethanesulfonate

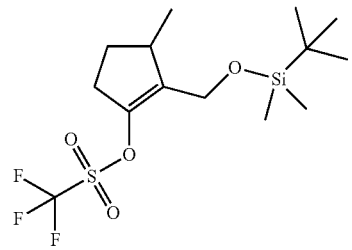 [SMILES: CC1CCC(OS(=O)(=O)C(F)(F)F)=C1CO[Si](C)(C)C(C)(C)C]

The title compound was synthesized starting from (±)-2-(hydroxymethyl)-3-methylcyclopent-1-en-1-yl trifluoromethanesulfonate analogously to the preparation of Intermediate 6. $^1$H NMR (400 MHz, DMSO-d$_6$) δ 4.31-4.22 (m, 1H), 4.19-4.14 (m, 1H), 3.28 (s, 1H), 2.87-2.78 (m, 1H), 2.63-2.55 (m, 1H), 2.24-2.13 (m, 1H), 1.53-1.44 (m, 1H), 1.07 (d, J=6.9 Hz, 3H), 0.87 (s, 9H), 0.06 (d, J=3.2 Hz, 6H).

Intermediate 12. ((2-Bromocyclopent-1-en-1-yl)methoxy)(tert-butyl)dimethylsilane

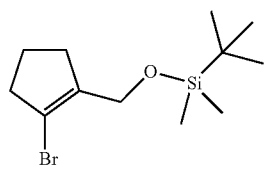

The title compound was synthesized starting from (2-bromocyclopent-1-en-1-yl)methanol (CAS#121898-54-2) analogously to the preparation of Intermediate 6. $^1$H NMR (400 MHz, CDCl$_3$) δ 4.19 (s, 2H), 2.60-2.53 (m, 2H), 2.35 (t, J=7.2 Hz, 2H), 1.86 (app. quin, J=7.6 Hz, 2H), 0.82 (s, 9H), 0.00 (s, 6H)

Intermediate 13

Intermediate 13-A. tert-Butyl 4-(4-amino-2-ethylphenyl)-5,6-dihydropyridine-1(2H)-carboxylate

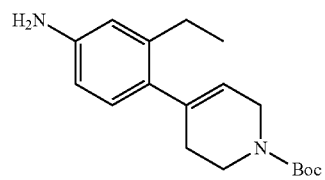 [SMILES: CCc1cc(N)ccc1C1=CCN(C(=O)OC(C)(C)C)CC1]

To a mixture of 4-bromo-3-ethylaniline (CAS#52121-42-3, 5 g, 24.99 mmol), 2-(3,6-dihydro-2H-pyran-4-yl)-4,4,5,5-tetramethyl-1,3,2-dioxaborolane (9.66 g, 31.2 mmol), and Pd(dppf)Cl$_2$CH$_2$Cl$_2$ adduct (1.02 g, 1.25 mmol) in DMF (100 mL) was added 2 M aq. potassium phosphate (37.5 mL, 75.0 mmol). The mixture was then stirred at 110° C. for 50 min, and then cooled to room temperature, and then diluted with EtOAc. The organic layer was then separated from the aqueous layer, and dried over Na₂SO₄, filtered, and then concentrated. The resulting residue was purified by silica gel flash column chromatography (heptane/EtOAc=1/0 to 4/6) to afford the title compound. MS (ESI+) m/z 303.1 (M+H).

Intermediate 13. tert-Butyl 4-(4-amino-2-ethylphenyl)piperidine-1-carboxylate

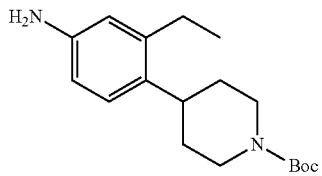 [SMILES: CCc1cc(N)ccc1C1CCN(C(=O)OC(C)(C)C)CC1]

The title compound was synthesized in a similar manner as described in the synthesis of Intermediate 2-1 starting from tert-butyl 4-(4-amino-2-ethylphenyl)-5,6-dihydropyridine-1(2H)-carboxylate. MS (ESI+) m/z 249.3 (M-tBu+2H).

Intermediate 14

Intermediate 14-A. tert-Butyl 4-(3-methyl-4-nitrophenyl)-5,6-dihydropyridine-1(2H)-carboxylate

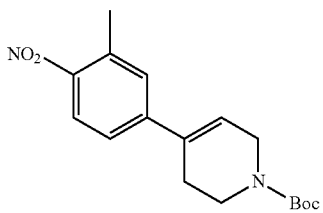 [SMILES: Cc1cc(C2=CCN(C(=O)OC(C)(C)C)CC2)ccc1[N+](=O)[O-]]

The title compound was synthesized analogously to the preparation of Intermediate 2-1-A using 4-bromo-2-methyl-1-nitrobenzene (CAS#52414-98-9) and tert-butyl 4-(4,4,5,5-tetramethyl-1,3,2-dioxaborolan-2-yl)-5,6-dihydropyridine-1(2H)-carboxylate. MS (ESI−) m/z 317.2 (M−H).

Intermediate 14-B. Cyclopropyl(4-(3-methyl-4-nitrophenyl)-5,6-dihydropyridin-1(2H)-yl)methanone

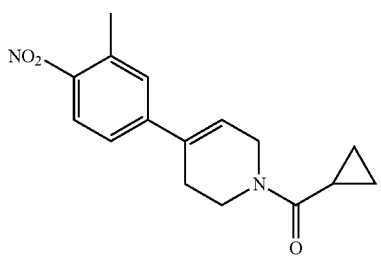 [SMILES: Cc1cc(C2=CCN(C(=O)C3CC3)CC2)ccc1[N+](=O)[O-]]

The title compound was synthesized from Intermediate 14-A in a similar manner as described in the synthesis of Intermediate 2-4 by way of first deprotecting the Boc moiety as described for Intermediate 2-3. MS (ESI+) m/z 287.2 (M+H).

Intermediate 14. (4-(4-Amino-3-methylphenyl)piperidin-1-yl)(cyclopropyl)methanone

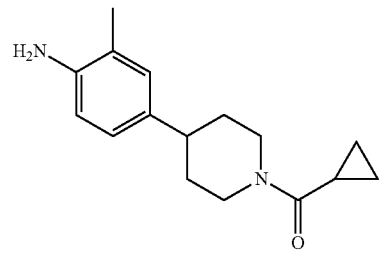 [SMILES: Cc1cc(C2CCN(C(=O)C3CC3)CC2)ccc1N]

A mixture of Intermediate 14-B (5.98 g, 20.89 mmol) and Pd/C (1.11 g) in EtOH (104 mL) was stirred under H₂ atmosphere at room temperature for 8 h. The mixture was filtered through a plug of Celite®, which was rinsed with EtOH. The filtrate was concentrated. The resulting residue was resubjected to the same reaction conditions for 8 h, and the mixture was filtered through a plug of Celite®, which was rinsed with EtOH. The filtrate was concentrated and the resulting residue was purified by silica gel flash column chromatography (0.2% Et₃N in heptane/EtOAc=1/0 to 0/1) to afford the title compound. MS (ESI+) m/z 259.3 (M+H).

Intermediate 15. (4-(4-Aminophenyl)piperidin-1-yl)(cyclopropyl)methanone

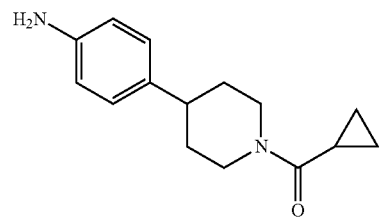 [SMILES: Nc1ccc(C2CCN(C(=O)C3CC3)CC2)cc1]

The title compound was synthesized by the similar method as described in the synthesis of Intermediate 14 but using 4-bromo-1-nitrobenzene (CAS#586-78-7) in the place of 4-bromo-2-methyl-1-nitrobenzene. MS (ESI+) m/z 245.1 (M+H).

Intermediate 16. (±)-Cyclopropyl((3,4-trans)-3-hydroxy-4-(4-hydroxyphenyl)piperidin-1-yl)methanone

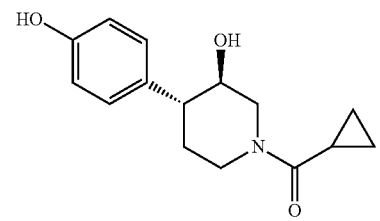 [SMILES: O=C(C1CC1)N1CC[C@H](c2ccc(O)cc2)[C@@H](O)C1]

To a suspension of (±)-(3,4-trans)-4-(4-hydroxyphenyl) piperidin-3-ol (CAS#188866-44-6, 295 mg, 1.527 mmol) in 5% aq. NaHCO₃/THF/CH₂Cl₂ (5 mL/5 mL/10 mL) was added cyclopropanecarbonyl chloride (200 μL, 2.20 mmol).

The mixture was then stirred at room temperature for 15 h. To the mixture was then added cyclopropanecarbonyl chloride (100 µL, 1.53 mmol). The mixture was then stirred at room temperature for additional 6 h. The reaction was then quenched with N,N-dimethylaminoethylenediamine. The mixture was then stirred for 2 h. The mixture was then rendered acidic by half satd. KHSO₄. The mixture was then extracted with EtOAc. The mixture was then washed successively with H₂O and brine, dried over Na₂SO₄, filtered, and then concentrated. The resulting residue was triturated with Et₂O. The resulting solid was collected by filtration to furnish the title compound. MS (ESI+) m/z 262.1 (M+H).

Example 1

Example 1-A. tert-Butyl 4-(4-((2-(6-(4-(ethoxycarbonyl)-5-(trifluoromethyl)-1H-pyrazol-1-yl)pyridin-2-yl)cyclohex-1-en-1-yl)methoxy)-3-methylphenyl)piperidine-1-carboxylate

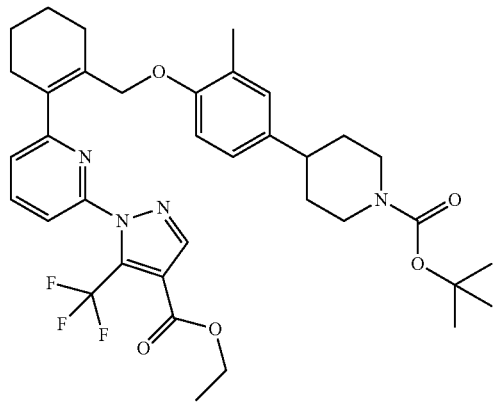 [SMILES: CCOC(=O)c1cnn(-c2cccc(C3=C(COc4ccc(C5CCN(C(=O)OC(C)(C)C)CC5)cc4C)CCCC3)n2)c1C(F)(F)F]

DIAD (0.209 mL, 1.072 mmol) was added dropwise to a THF (5 mL) solution of Intermediate 9 (373 mg, 0.944 mmol), Intermediate 2-1 (250 mg, 0.858 mmol) and PPh₃ (281 mg, 1.072 mmol) at rt. The mixture was stirred for 1 h and then concentrated. The residue was purified by silica gel flash column chromatography (heptane to 25% EtOAc in heptane) to afford the title compound. MS (ESI+) m/z 669.3 (M+H).

Example 1-B. Ethyl 1-(6-(2-((2-methyl-4-(piperidin-4-yl)phenoxy)methyl)cyclohex-1-en-1-yl)pyridin-2-yl)-5-(trifluoromethyl)-1H-pyrazole-4-carboxylate

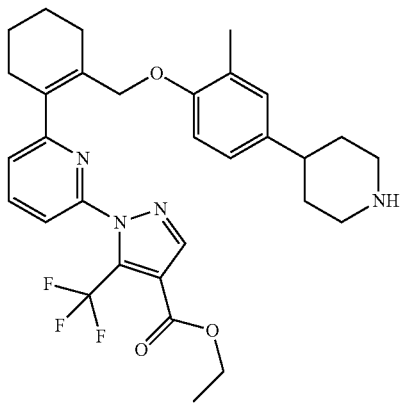 [SMILES: CCOC(=O)c1cnn(-c2cccc(C3=C(COc4ccc(C5CCNCC5)cc4C)CCCC3)n2)c1C(F)(F)F]

Trifluoroacetic acid (5 mL, 64.9 mmol) was added dropwise to a DCM (5 mL) solution of Example 1-A (396 mg, 0.592 mmol) at 0° C. The whole mixture was stirred for 30 min at 0° C. Acetonitrile (10 mL) was added to the mixture and then the solvent was removed under reduced pressure. The resulting residue was diluted with DCM and sat'd. aq. NaHCO₃, and then passed through an ISOLUTE® Phase Separator. The organics were concentrated to furnish the title compound. MS (ESI+) m/z 569.4 (M+H).

Example 1-C. Ethyl 1-(6-(2-((4-(1-(cyclopropanecarbonyl)piperidin-4-yl)-2-methylphenoxy)methyl)cyclohex-1-en-1-yl)pyridin-2-yl)-5-(trifluoromethyl)-1H-pyrazole-4-carboxylate

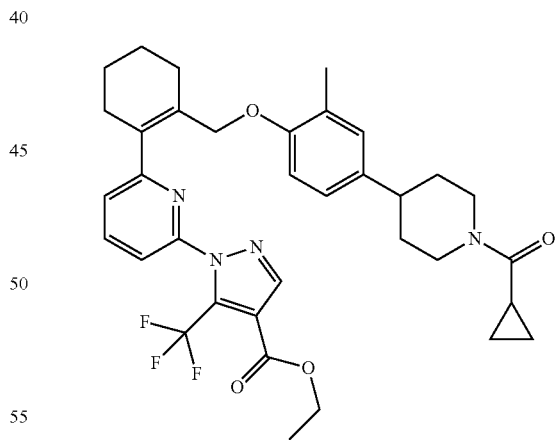

Cyclopropylcarbonyl chloride (CAS #4023-34-1, 0.006 mL, 0.100 mmol) was added to a DCM (2 mL) solution of Example 1-B (38 mg, 0.067 mmol) and DIPEA (0.035 mL, 0.200 mmol) at 0° C. The resulting mixture was stirred for 30 min at 0° C. and then water was added. The mixture was then passed through an ISOLUTE® Phase Separator. The organics were concentrated. The resulting residue was purified by silica gel flash column chromatography (heptane to 50% EtOAc in heptane) to afford the title compound. MS (ESI+) m/z 637.3 (M+H).

Example 1. 1-(6-(2-((4-(1-(Cyclopropanecarbonyl)piperidin-4-yl)-2-methylphenoxy)methyl)cyclohex-1-en-1-yl)pyridin-2-yl)-5-(trifluoromethyl)-1H-pyrazole-4-carboxylic acid

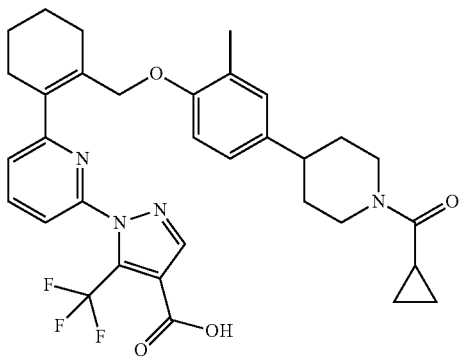 [SMILES: Cc1cc(C2CCN(C(=O)C3CC3)CC2)ccc1OCC1=C(c2cccc(-n3ncc(C(=O)O)c3C(F)(F)F)n2)CCCC1]

LiOH (0.18 mL, 1M aq.) was added to a THF/MeOH solution (1 mL/1 mL) of Example 1-C (23 mg, 0.036 mmol). The mixture was then stirred at 50° C. for 16 h. The reaction mixture was rendered acidic by the addition of 0.1 N aq HCl until pH<4. The mixture was then extracted with EtOAc. The organic phase was washed with water, brine and then dried over sodium sulfate, filtered, and then concentrated. The resulting residue was purified by RP-HPLC (HC-B) to afford the title compound. $^1$H NMR (400 MHz, DMSO-$d_6$) δ 13.44 (s, 1H), 8.28 (s, 1H), 8.08 (t, J=7.8 Hz, 1H), 7.67 (dd, J=8.0, 0.8 Hz, 1H), 7.50 (dd, J=7.8, 0.9 Hz, 1H), 7.00 (d, J=2.2 Hz, 1H), 6.89 (dd, J=8.3, 2.2 Hz, 1H), 6.60 (d, J=8.4 Hz, 1H), 4.53-4.43 (m, 1H), 4.40 (s, 2H), 4.38-4.30 (m, 1H), 3.12 (t, J=12.8 Hz, 1H), 2.71-2.53 (m, 2H), 2.43 (s, 2H), 2.32 (dd, J=5.0, 2.5 Hz, 2H), 2.11 (s, 3H), 2.04-1.92 (m, 1H), 1.79-1.66 (m, 6H), 1.49 (d, J=13.1 Hz, 1H), 1.37 (s, 1H), 0.77-0.65 (m, 4H). HRMS; calcd. for $C_{33}H_{36}F_3N_4O_4$ (M+H) 609.2689, found 609.2682.

Example 2

The following compounds were prepared with similar methods as described above using the appropriate starting materials. Specifically, Example 2-1, Example 2-6, Example 2-7, Example 2-8, Example 2-9, Example 2-10, Example 2-11, and Example 2-12 were prepared in a fashion similar to Example 1. Example 2-2, Example 2-3, Example 2-4, and Example 2-5 were prepared via a Suzuki-type coupling in a manner similar to that described for Intermediate 9-A, but employing Intermediate 1-1 and Intermediate 5-2 as starting material, the subsequent product could then be further transformed to the title compounds in a manner similar to the process to transform Example 1-A to Example 1.

| Example | Structure/Name | Starting Materials | Analytical Data |
|---|---|---|---|
| 2-1 | 1-(6-(2-((2-Methyl-4-(1-propionylpiperidin-4-yl)phenoxy)methyl)cyclohex-1-en-1-yl)pyridin-2-yl)-5-(trifluoromethyl)-1H-pyrazole-4-carboxylic acid | Intermediate 9, Intermediate 2-1, and propionic anhydride(CAS # 123-62-6) | $^1$H NMR (400 MHz, DMSO-$d_6$) δ 13.43 (s, 1H), 8.27 (s, 1H), 8.08 (t, J = 7.9 Hz, 1H), 7.67 (dd, J = 7.9, 0.8 Hz, 1H), 7.50 (dd, J = 7.8, 0.9 Hz, 1H), 7.02-6.96 (m, 1H), 6.87 (dd, J = 8.3, 2.3 Hz, 1H), 6.60 (d, J = 8.4 Hz, 1H), 4.51 (d, J = 12.8 Hz, 1H), 4.40 (s, 2H), 3.92 (d, J = 13.2 Hz, 1H), 3.28 (s, 1H), 3.04 (t, J = 12.8 Hz, 1H), 2.67-2.51 (m, 2H), 2.42 (s, 2H), 2.33 (q, J = 7.1 Hz, 4H), 2.11 (s, 3H), 1.69 (br. s., 5H), 1.48 (t, J = 10.5 Hz, 1H), 1.36 (dd, J = 13.1, 8.9 Hz, 1H), 0.99 (t, J = 7.4 Hz, 3H). HRMS calcd. for $C_{32}H_{36}F_3N_4O_4$ (M + H) 597.2689, found 597.2677. |
| 2-2 | 1-(6-(2-((4-(1-(Methoxycarbonyl)piperidin-4-yl)-2-methylphenoxy)methyl)cyclohex-1-en-1-yl)pyridin-2-yl)-5-(trifluoromethyl)-1H-pyrazole-4-carboxylic acid | Intermediate 1-1, Intermediate 5-2, and methyl chloroformate, CAS # 79-22-1. | $^1$H NMR (400 MHz DMSO-$d_6$) δ 7.97 (t, J = 7.8 Hz, 1H), 7.70 (s, 1H), 7.55 (dd, J = 0.7, 8.0 Hz, 1H), 7.36 (dd, J = 0.6, 7.7 Hz, 1H), 6.99 (d, J = 2.0 Hz, 1H), 6.88 (dd, J = 2.2, 8.3 Hz, 1H), 6.61 (d, J = 8.3 Hz, 1H), 4.42-4.38 (s, 2H), 4.11-4.01 (m, 2H), 3.59 (s, 3H), 3.52-3.46 (m, 1H), 3.44-3.39 (m, 1H), 2.83 (br. s., 1H), 2.44 (br. s., 2H), 2.31 (br. s., 2H), 2.12 (s, 3H), 1.70 (br. s., 6H), 1.43 (dq, J = 4.2, 12.6 Hz, 2H). HRMS calcd. for $C_{31}H_{34}F_3N_4O_5$ (M + H) 599.2481, found 599.2518. |

| Example | Structure/Name | Starting Materials | Analytical Data |
|---|---|---|---|
| 2-3 | 1-(6-(2-((2-Methyl-4-(1-(methylsulfonyl)piperidin-4-yl)phenoxy)methyl)cyclohex-1-en-1-yl)pyridin-2-yl)-5-(trifluoromethyl)-1H-pyrazole-4-carboxylic acid | Intermediate 1-1, Intermediate 5-2, and methanesulfonyl chloride (CAS # 124-63-0) | $^1$H NMR (400 MHz, DMSO-$d_6$) δ 13.54 (s, 1H), 8.04 (app. t, J = 7.8 Hz, 2H), 7.63 (d, J = 7.8 Hz, 1H), 7.45 (d, J = 7.6 Hz, 1H), 7.02 (d, J = 2.1 Hz, 1H), 6.91 (dd, J = 2.2, 8.3 Hz, 1H), 6.62 (d, J = 8.4 Hz, 1H), 4.41 (s, 2H), 3.64 (d, J = 11.7 Hz, 2H), 2.88 (s, 3H), 2.77 (dt, J = 2.3, 12.1 Hz, 2H), 2.43 (br. s., 2H), 2.31 (br. s., 2H), 2.12 (s, 3H), 1.79 (d, J = 12.7 Hz, 2H), 1.70 (br. s., 4H), 1.59 (dq, J = 4.1, 12.6 Hz, 2H). HRMS calcd. for $C_{30}H_{34}F_3N_4O_5S$ (M + H) 619.2202, found 619.2217. |
| 2-4 | 1-(6-(2-((4-(1-(Dimethylcarbamoyl)piperidin-4-yl)-2-methylphenoxy)methyl)cyclohex-1-en-1-yl)pyridin-2-yl)-5-(trifluoromethyl)-1H-pyrazole-4-carboxylic acid | Intermediate 1-1, Intermediate 5-2, and dimethylcarbamyl chloride (CAS # 79-44-7) | $^1$H NMR (400 MHz, DMSO-$d_6$) δ 7.99 (t, J = 7.8 Hz, 1H), 7.81 (br. s., 1H), 7.58 (d, J = 7.7 Hz, 1H), 7.39 (d, J = 7.6 Hz, 1H), 6.99 (d, J = 2.0 Hz, 1H), 6.89 (dd, J = 2.1, 8.4 Hz, 1H), 6.61 (d, J = 8.4 Hz, 1H), 4.40 (s, 2H), 3.61 (d, J = 13.1 Hz, 2H), 2.74 (s, 6H), 2.44 (br. s., 2H), 2.31 (br. s., 2H), 2.13 (s, 3H), 1.70 (br. s., 5H), 1.66 (br. s., 1H), 1.50 (dq, J = 3.7, 12.4 Hz, 2H). HRMS; calcd. for $C_{32}H_{37}F_3N_5O_4$ (M + H) 612.2798, found 612.2801. |
| 2-5 | 1-(6-(2-((4-(1-(2-Hydroxyacetyl)piperidin-4-yl)-2-methylphenoxy)methyl)cyclohex-1-en-1-yl)pyridin-2-yl)-5-(trifluoromethyl)-1H-pyrazole-4-carboxylic acid | Intermediate 1-1, Intermediate 5-2, and acetoxyacetyl chloride (CAS # 13831-31-7) | $^1$H NMR (400 MHz, DMSO-$d_6$) δ 7.97 (t, J = 7.8 Hz, 1H), 7.69 (s, 1H), 7.55 (dd, J = 0.7, 8.0 Hz, 1H), 7.35 (dd, J = 0.6, 7.6 Hz, 1H), 6.98 (d, J = 2.0 Hz, 1H), 6.87 (dd, J = 2.2, 8.3 Hz, 1H), 6.61 (d, J = 8.4 Hz, 1H), 4.48 (t, J = 5.4 Hz, 1H), 4.40 (s, 2H), 4.17-4.00 (m, 2H), 3.74 (d, J = 12.8 Hz, 1H), 3.06-2.95 (m, 1H), 2.65-2.57 (m, 2H), 2.44 (br. s., 2H), 2.30 (br. s., 2H), 2.12 (s, 3H), 1.69 (br. s., 6H), 1.58-1.32 (m, 2H). HRMS; calcd. for $C_{31}H_{34}F_3N_4O_5$ (M + H) 599.2481, found 599.2504. |

| Example | Structure/Name | Starting Materials | Analytical Data |
|---|---|---|---|
| 2-6 | 1-(6-(2-((4-(1-(Cyclopropanecarbonyl)piperidin-4-yl)phenoxy)methyl)cyclohex-1-en-1-yl)pyridin-2-yl)-5-(trifluoromethyl)-1H-pyrazole-4-carboxylic acid | Intermediate 9, t-butyl 4-(4-hydroxyphenyl)piperidine-1-carboxylate (CAS # 149377-19-5), and cyclopropyl carbonyl chloride | $^1$H NMR (400 MHz, DMSO-$d_6$) δ 13.43 (br s, 1H). 8.28 (s, 1H), 8.07 (t, J = 7.8 Hz, 1H), 7.67 (dd, J = 8.0, 0.8 Hz, 1H), 7.49 (dd, J = 7.7, 0.9 Hz, 1H), 7.13-7.04 (m, 2H), 6.79-6.70 (m, 2H), 4.48 (s, 1H), 4.38 (s, 2H), 3.13 (s, 1H), 2.78-2.54 (m, 2H), 2.42 (s, 2H), 2.28 (s, 2H), 1.98 (tt, J = 7.6, 5.2 Hz, 2H), 1.77 (s, 1H), 1.69 (br. s., 5H), 1.58-1.27 (m, 2H), 0.77-0.66 (m, 4H). HRMS calcd. for $C_{32}H_{34}N_4O_4F_3$ (M + H) 595.2532, found 595.2554. |
| 2-7 | 1-(6-(2-((4-(1-(Diethylcarbamoyl)piperidin-4-yl)-2-methylphenoxy)methyl)cyclohex-1-en-1-yl)pyridin-2-yl)-5-(trifluoromethyl)-1H-pyrazole-4-carboxylic acid | Intermediate 2-1, Intermediate 9, and diethylcarbamic chloride (CAS # 88-10-8) | $^1$H NMR (400 MHz, DMSO-$d_6$) δ 13.45 (br. s., 1H), 8.25 (s, 1H), 8.08 (t, J = 7.8 Hz, 1H), 7.67 (d, J = 7.9 Hz, 1H), 7.50 (d, J = 7.7 Hz, 1H), 6.99 (d, J = 1.8 Hz, 1H), 6.88 (dd, J = 2.0, 8.4 Hz, 1H), 6.60 (d, J = 8.4 Hz, 1H), 4.40 (s, 2H), 3.57 (d, J = 13.0 Hz, 2H), 3.12 (q, J = 7.0 Hz, 4H), 2.74 (t, J = 11.7 Hz, 1H), 2.43 (br. s., 2H), 2.31 (br. s., 2H), 2.11 (s, 3H), 1.74-1.65 (m, 6H), 1.49 (dq, J = 3.8, 12.4 Hz, 2H), 1.04 (t, J = 7.0 Hz, 6H); HRMS calcd. for $C_{34}H_{41}F_3N_5O_4$ (M + H) 640.3111, found 640.3168. |
| 2-8 | 1-(6-(2-((4-(1-(Ethylsulfonyl)piperidin-4-yl)-2-methylphenoxy)methyl)cyclohex-1-en-1-yl)pyridin-2-yl)-5-(trifluoromethyl)-1H-pyrazole-4-carboxylic acid | Intermediate 2-1, Intermediate 9, and ethanesulfonyl chloride (CAS # 594-44-5) | $^1$H NMR (400 MHz, DMSO-$d_6$) δ 13.43 (br. s., 1H), 8.27 (br. s., 1H), 8.08 (t, J = 7.8 Hz, 1H), 7.67 (d, J = 7.8 Hz, 1H), 7.50 (d, J = 7.6 Hz, 1H), 7.00 (d, J = 1.8 Hz, 1H), 6.89 (dd, J = 2.1, 8.4 Hz, 1H), 6.61 (d, J = 8.3 Hz, 1H), 4.41 (s, 2H), 3.68 (d, J = 12.0 Hz, 2H), 3.06 (q, J = 7.3 Hz, 2H), 2.86 (dt, J = 2.1, 12.1 Hz, 2H), 2.43 (br. s., 2H), 2.12 (s, 3H), 1.78 (d, J = 12.5 Hz, 2H), 1.70 (br. s., 3H), 1.55 (dq, J = 4.2, 12.5 Hz, 2H), 1.22 (t, J = 7.4 Hz, 3H). HRMS calcd. for $C_{31}H_{36}F_3N_4O_5S$ (M + H) 633.2359, found 633.2401. |

| Example | Structure/Name | Starting Materials | Analytical Data |
|---|---|---|---|
| 2-9 | 1-(6-(2-((4-(1-(Cyclopropylsulfonyl)piperidin-4-yl)-2-methylphenoxy)methyl)cyclohex-1-en-1-yl)pyridin-2-yl)-5-(trifluoromethyl)-1H-pyrazole-4-carboxylic acid | Intermediate 2-1, Intermediate 9, and cyclopropylsulfonyl chloride (CAS # 139631-62-2) | $^1$H NMR (400 MHz, DMSO-$d_6$) δ 13.43 (br. s., 1H), 8.27 (s, 1H), 8.08 (t, J = 7.8 Hz, 1H), 7.67 (d, J = 7.9 Hz, 1H), 7.50 (d, J = 7.2 Hz, 1H), 7.01 (d, J = 2.1 Hz, 1H), 6.90 (dd, J = 2.1, 8.3 Hz, 1H), 6.61 (d, J = 8.4 Hz, 1H), 4.41 (s, 2H), 3.68 (d, J = 12.0 Hz, 2H), 2.89 (dt, J = 2.0, 12.1 Hz, 2H), 2.43 (br. s., 2H), 2.12 (s, 3H), 1.79 (d, J = 12.2 Hz, 2H), 1.68-1.68 (m, 1H), 1.72-1.66 (m, 4H), 1.59 (dq, J = 3.7, 12.4 Hz, 2H), 1.25-1.20 (m, 1H), 1.03-0.90 (m, 4H). HRMS calcd. for $C_{32}H_{36}F_3N_4O_5S$ (M + H) 645.2359 found 645.2430. |
| 2-10 | 1-(6-(2-((4-(1-Isobutyrylpiperidin-4-yl)-2-methylphenoxy)methyl)cyclohex-1-en-1-yl)pyridin-2-yl)-5-(trifluoromethyl)-1H-pyrazole-4-carboxylic acid | Intermediate 2-1, Intermediate 9, and isobutyryl chloride (CAS # 79-30-1) | $^1$H NMR (400 MHz, DMSO-$d_6$) δ 8.14 (s, 1H), 8.05 (t, J = 7.8 Hz, 1H), 7.64 (dd, J = 8.1, 0.9 Hz, 1H), 7.47 (dd, J = 7.7, 0.9 Hz, 1H), 6.99 (d, J = 2.2 Hz, 1H), 6.88 (dd, J = 8.4, 2.3 Hz, 1H), 6.60 (d, J = 8.4 Hz, 1H), 4.53 (d, J = 12.5 Hz, 1H), 4.40 (s, 2H), 4.02 (d, J = 13.3 Hz, 1H), 3.16 (d, J = 10.9 Hz, 1H), 3.07 (t, J = 12.9 Hz, 1H), 2.88 (p, J = 6.7 Hz, 1H), 2.61 (dt, J = 12.0, 3.6 Hz, 2H), 2.43 (s, 2H), 2.31 (d, J = 4.6 Hz, 2H), 2.11 (s, 3H), 1.70 (br. s., 6H), 1.52-1.27 (m, 2H), 1.00 (app dd, J = 10.7, 6.5 Hz, 6H). HRMS calcd. for $C_{33}H_{38}F_3N_4O_4$ (M + H) 611.2840, found 611.2902. |
| 2-11 | 1-(6-(2-((4-(1-(Cyclobutanecarbonyl)piperidin-4-yl)-2-methylphenoxy)methyl)cyclohex-1-en-1-yl)pyridin-2-yl)-5-(trifluoromethyl)-1H-pyrazole-4-carboxylic acid | Intermediate 2-1, Intermediate 9, and cyclobutanecarbonyl chloride (CAS # 5006-22-4) | $^1$H NMR (400 MHz, DMSO-$d_6$) δ 8.09 (s, 1H), 8.04 (t, J = 7.8 Hz, 1H), 7.63 (dd, J = 8.1, 0.8 Hz, 1H), 7.45 (dd, J = 7.7, 0.9 Hz, 1H), 6.98 (d, J = 2.2 Hz, 1H), 6.87 (dd, J = 8.4, 2.3 Hz, 1H), 6.60 (d, J = 8.4 Hz, 1H), 4.48 (d, J = 13.0 Hz, 1H), 4.40 (s, 2H), 3.75 (d, J = 13.6 Hz, 1H), 3.03-2.93 (m, 1H), 2.65-2.53 (m, 3H), 2.43 (s, 2H), 2.31 (s, 2H), 2.19 (ddd, J = 20.3, 10.2, 2.6 Hz, 2H), 2.11 (s, 4H), 2.10-2.02 (m, 2H), 1.95-1.85 (dp, J = 10.8, 8.9 Hz, 1H), 1.78-1.64 (m, 7H), 1.46-1.28 (m, 2H). HRMS calcd. for $C_{34}H_{38}F_3N_4O_4$ (M + H) 623.28396, found 623.2897 |

| Example | Structure/Name | Starting Materials | Analytical Data |
|---|---|---|---|
| 2-12 | 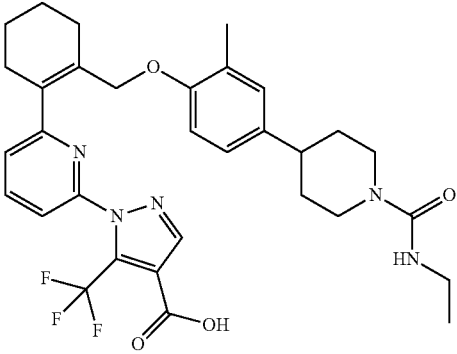 [SMILES: Cc1cc(C2CCN(C(=O)[C@H](C)O)CC2)ccc1OCC1=C(c2cccc(-n3ncc(C(=O)O)c3C(F)(F)F)n2)CCCC1]<br>1-(6-(2-((4-(1-(Ethylcarbamoyl)piperidin-4-yl)-2-methylphenoxy)methyl)cyclohex-1-en-1-yl)pyridin-2-yl)-5-(trifluoromethyl)-1H-pyrazole-4-carboxylic acid | Intermediate 2-1, Intermediate 9, and ethyl isocyanate (CAS # 109-90-0) | $^1$H NMR (400 MHz, DMSO-$d_6$) δ 13.42 (br. s., 1H), 8.28 (s, 1H), 8.08 (t, J = 7.9 Hz, 1H), 7.67 (dd, J = 0.6, 7.9 Hz, 1H), 7.50 (dd, J = 0.6, 7.8 Hz, 1H), 6.97 (d, J = 1.8 Hz, 1H), 6.86 (dd, J = 2.3, 8.4 Hz, 1H), 6.60 (d, J = 8.4 Hz, 1H), 6.41 (t, J = 5.3 Hz, 1H), 4.40 (s, 2H), 4.04 (d, J = 13.1 Hz, 2H), 3.04 (dq, J = 5.6, 7.1 Hz, 2H), 2.72-2.62 (m, 4H), 2.43 (br. s., 2H), 2.11 (s, 3H), 1.70 (br. s., 3H), 1.64 (d, J = 13.7 Hz, 2H), 1.38 (dq, J = 3.2, 12.3 Hz, 2H), 1.00 (t, J = 7.2 Hz, 3H). HRMS calcd. for $C_{32}H_{37}F_3N_5O_4$ (M + H) 612.2798, found 612.2844. |
| 2-13 | 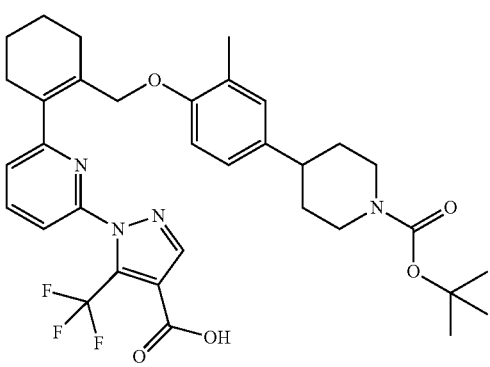<br>1-(6-(2-((4-(1-(tert-butoxycarbonyl)piperidin-4-yl)-2-methylphenoxy)methyl)cyclohex-1-en-1-yl)pyridin-2-yl)-5-(trifluoromethyl)-1H-pyrazole-4-carboxylic acid | (Example 1-A was saponified by the method analogous to the method for the synthesis of Example 1) | $^1$H NMR (400 MHz, DMSO-$d_6$) δ 8.28 (s, 1H), 8.08 (t, J = 7.9 Hz, 1H), 7.67 (d, J = 8.0 Hz, 1H), 7.50 (d, J = 7.1 Hz, 1H), 6.98 (d, J = 1.9 Hz, 1H), 6.91-6.83 (m, 1H), 6.59 (d, J = 8.4 Hz, 1H), 4.40 (s, 2H), 4.03 (d, J = 12.2 Hz, 2H), 2.75 (s, 2H), 2.43 (s, 2H), 2.32 (d, J = 7.0 Hz, 2H), 2.11 (s, 3H), 1.76-1.59 (m, J = 16.2 Hz, 6H), 1.41 (s, 12H). HRMS calcd. for $C_{34}H_{40}F_3N_4O_5$ (M + H) 641.2951, found 641.2924. |

Example 3

Example 3-A. (S)-Ethyl 1-(6-(2-((4-(1-(2-hydroxypropanoyl)piperidin-4-yl)-2-methylphenoxy)methyl)cyclohex-1-en-1-yl)pyridin-2-yl)-5-(trifluoromethyl)-1H-pyrazole-4-carboxylate

Example 3. (S)-1-(6-(2-((4-(1-(2-hydroxypropanoyl)piperidin-4-yl)-2-methylphenoxy)methyl)cyclohex-1-en-1-yl)pyridin-2-yl)-5-(trifluoromethyl)-1H-pyrazole-4-carboxylic acid

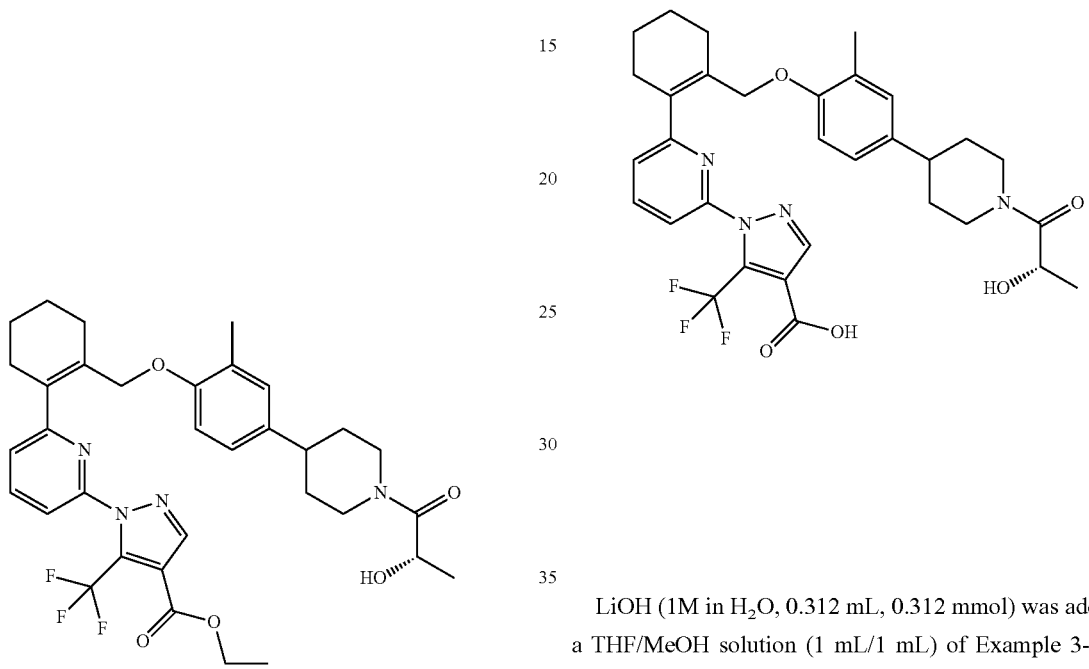

HATU (38.4 mg, 0.101 mmol) was added to a DMF (2 mL) solution of Example 1-B (50 mg, 0.088 mmol), L-(+)-lactic acid (CAS #79-33-4, 8.71 mg, 0.097 mmol) and DIPEA (0.023 mL, 0.132 mmol) at rt. The mixture was then stirred for 1 h, and then diluted with water and EtOAc. The organic phase was washed with water and brine, dried over sodium sulfate, filtered, and then concentrated. The resulting residue was purified by silica gel flash column chromatography (heptane to 100% EtOAc/heptane) to afford the title compound. MS (ESI+) m/z 641.4 (M+H).

LiOH (1M in $H_2O$, 0.312 mL, 0.312 mmol) was added to a THF/MeOH solution (1 mL/1 mL) of Example 3-A (40 mg, 0.062 mmol). The mixture was then stirred at 50° C. for 3 h. The reaction mixture was rendered acidic by the addition of 0.1 N aq. HCl until pH<4. The mixture was then extracted with EtOAc. The organic phase was washed with water, brine and then dried over sodium sulfate, filtered, and then concentrated. The resulting residue was purified by RP-HPLC (HC-B) to afford the title compound. $^1$H NMR (400 MHz, DMSO-$d_6$) δ 13.42 (br s, 1H), 8.27 (s, 1H), 8.08 (t, J=7.9 Hz, 1H), 7.67 (dd, J=8.0, 0.8 Hz, 1H), 7.50 (dd, J=7.8, 0.9 Hz, 1H), 6.99 (s, 1H), 6.88 (d, J=8.2 Hz, 1H), 6.60 (d, J=8.4 Hz, 1H), 4.79 (s, 1H), 4.54-4.43 (m, 2H), 4.04 (s, 2H), 3.04 (t, J=12.8 Hz, 1H), 2.71-2.52 (m, 2H), 2.43 (br s, 2H), 2.31 (br s, 2H), 2.11 (s, 3H), 1.77-1.66 (m, 7H), 1.55-1.43 (m, 1H), 1.42-1.35 (m, 1H), 1.26-1.14 (m, 4H). HRMS; calcd. for $C_{32}H_{36}F_3N_4O_5$ (M+H) 612.2560, found 613.2686.

Example 4

The following compounds were prepared with similar methods as described for Example 3 using Intermediate 2-1, Intermediate 9 and the appropriate acid starting materials.

| Ex | Structure/Name | Starting Materials | Analytical Data |
|---|---|---|---|
| 4-1 | (R)-1-(6-(2-((4-(1-(2-Hydroxypropanoyl)piperidin-4-yl)-2-methylphenoxy)methyl)cyclohex-1-en-1-yl)pyridin-2-yl)-5-(trifluoromethyl)-1H-pyrazole-4-carboxylic acid | D-(−)-lactic acid (CAS # 10326-41-7) | $^1$H NMR (400 MHz, DMSO-$d_6$) δ 8.26 (s, 1H), 8.08 (t, J = 7.9 Hz, 1H), 7.67 (dd, J = 8.0, 0.8 Hz, 1H), 7.50 (dd, J = 7.8, 0.9 Hz, 1H), 6.99 (s, 1H), 6.88 (d, J = 8.3 Hz, 1H), 6.60 (d, J = 8.4 Hz, 1H), 4.53-4.38 (m, 4H), 3.04 (t, J = 12.9 Hz, 1H), 2.71-2.56 (m, 3H), 2.43 (s, 2H), 2.31 (d, J = 4.3 Hz, 2H), 2.09 (d, J = 15.7 Hz, 4H), 1.74-1.66 (m, 6H), 1.55-1.43 (m, 1H), 1.38 (s, 1H), 1.26-1.13 (m, 4H). HRMS; calcd. for $C_{32}H_{36}F_3N_4O_5$ (M + H) 613.2632, found 613.2689 |
| 4-2 | 1-(6-(2-((2-Methyl-4-(1-picolinoylpiperidin-4-yl)phenoxy)methyl)cyclohex-1-en-1-yl)pyridin-2-yl)-5-(trifluoromethyl)-1H-pyrazole-4-carboxylic acid | picolinic acid (CAS # 98-98-6) | $^1$H NMR (400 MHz, DMSO-$d_6$) δ 13.43 (br. s., 1H), 8.59 (d, J = 3.9 Hz, 1H), 8.28 (s, 1H), 8.08 (t, J = 7.8 Hz, 1H), 7.92 (t, J = 7.2 Hz, 1H), 7.67 (d, J = 7.8 Hz, 1H), 7.57 (d, J = 7.6 Hz, 1H), 7.53-7.43 (m, 2H), 7.01 (br. s., 1H), 6.90 (d, J = 7.8 Hz, 1H), 6.61 (d, J = 8.3 Hz, 1H), 4.62 (d, J = 12.0 Hz, 1H), 4.40 (br. s., 2H), 3.70 (d, J = 12.5 Hz, 1H), 3.11 (t, J = 12.2 Hz, 1H), 2.83 (t, J = 12.0 Hz, 1H), 2.74-2.65 (m, 1H), 2.43 (br. s., 2H), 2.31 (br. s., 2H), 2.12 (s, 3H), 1.82 (d, J = 12.7 Hz, 1H), 1.70 (br. s., 4H), 1.64-1.49 (m, 3H). HRMS calcd. for $C_{35}H_{35}F_3N_5O_4$ (M + H) 646.2641 found 646.2706. |

Example 5

Example 5-A. tert-Butyl 6-((2-(6-(4-(ethoxycarbonyl)-5-(trifluoromethyl)-1H-pyrazol-1-yl)pyridin-2-yl)cyclohex-1-en-1-yl)methoxy)-3,4-dihydroisoquinoline-2(1H)-carboxylate

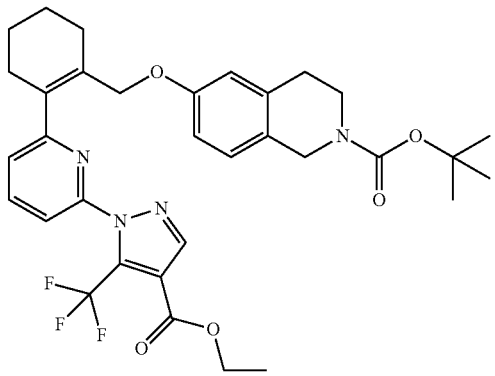 [SMILES: CCOC(=O)c1cnn(-c2cccc(C3=C(COc4ccc5c(c4)CCN(C(=O)OC(C)(C)C)C5)CCCC3)n2)c1C(F)(F)F]

DIAD (0.060 mL, 0.308 mmol) was added dropwise to a THF (5 mL) solution of Intermediate 3-1 (64 mg, 0.257 mmol), Intermediate 9 (110 mg, 0.277 mmol) and PPh$_3$ (81 mg, 0.308 mmol) at rt. The reaction was stirred for 16 h and then concentrated. The residue was purified by silica gel flash column chromatography (heptane to 60% EtOAc in heptane) to afford the title compound. MS (ESI+) m/z 627.3 (M+H).

Example 5-B. Ethyl 1-(6-(2-(((1,2,3,4-tetrahydroisoquinolin-6-yl)oxy)methyl)cyclohex-1-en-1-yl)pyridin-2-yl)-5-(trifluoromethyl)-1H-pyrazole-4-carboxylate

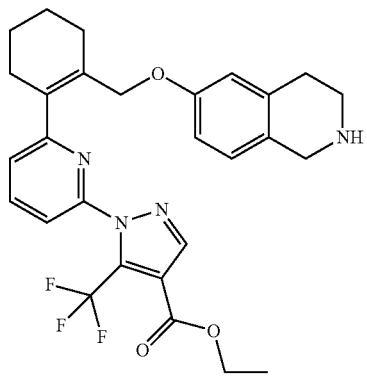 [SMILES: CCOC(=O)c1cnn(-c2cccc(C3=C(COc4ccc5c(c4)CCNC5)CCCC3)n2)c1C(F)(F)F]

Trifluoroacetic acid (0.5 mL, 6.49 mmol) was added dropwise to a DCM (2 mL) solution of Example 5-A (80 mg, 0.128 mmol) at 0° C. The whole mixture was stirred for 45 min at 0° C. Acetonitrile (3 mL) was added to the mixture and it was then concentrated. The resulting residue was diluted with EtOAc and sat'd. aq. NaHCO$_3$. The organic layer was then separated. The aqueous layer was extracted with EtOAc. The combined organic layers were washed successively with brine, dried over Na$_2$SO$_4$, filtered, and then concentrated to furnish the title compound. MS (ESI+) m/z 527.3 (M+H).

Example 5-C. Ethyl 1-(6-(2-(((2-((6-methylpyridin-2-yl)methyl)-1,2,3,4-tetrahydroisoquinolin-6-yl)oxy)methyl)cyclohex-1-en-1-yl)pyridin-2-yl)-5-(trifluoromethyl)-1H-pyrazole-4-carboxylate

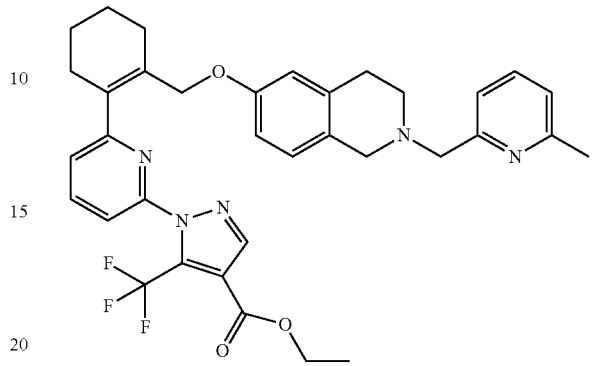

A mixture of Example 5-B (23 mg, 0.044 mmol), DIPEA (0.023 mL, 0.131 mmol), and 2-(bromomethyl)-6-methylpyridine (CAS #68470-59-7, 12.2 mg, 0.066 mmol) in DCM (1 mL) was stirred at rt for 16 h, and then concentrated. The resulting residue was purified by silica gel flash column chromatography (0-10% (MeOH with 10% NH$_4$OH) in DCM) to afford the title compound. MS (ESI+) m/z 632.4 (M+H).

Example 5. 1-(6-(2-(((2-((6-Methylpyridin-2-yl)methyl)-1,2,3,4-tetrahydroisoquinolin-6-yl)oxy)methyl)cyclohex-1-en-1-yl)pyridin-2-yl)-5-(trifluoromethyl)-1H-pyrazole-4-carboxylic acid

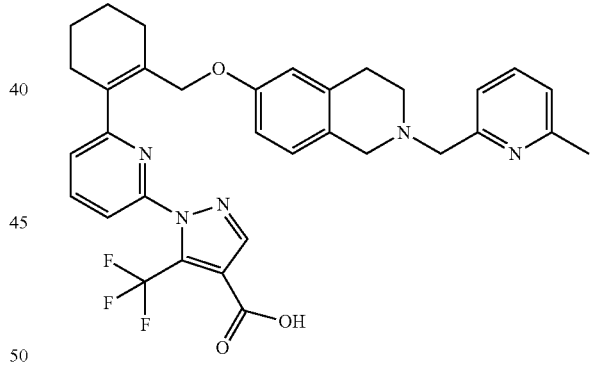

A mixture of Example 5-C (16 mg, 0.025 mmol) in THF (1 mL), MeOH (1 mL) and 1 N aq NaOH (1 mL, 1.00 mmol) was heated at 50° C. for 1.5 h, and then cooled to room temperature. The reaction mixture was then diluted with EtOAc and water. The mixture was rendered acidic (pH 5-6) by the addition of 1 N aq. HCl. The organic phase was washed with brine, then dried over sodium sulfate, filtered, and concentrated. The resulting residue was triturated with acetonitrile, and then the resulting precipitate was collected by filtration to afford the title compound. $^1$H NMR (400 MHz, DMSO-d6) δ 8.19 (s, 1H), 8.06 (t, J=7.8 Hz, 1H), 7.70-7.60 (m, 2H), 7.48 (d, J=7.7 Hz, 1H), 7.25 (d, J=7.7 Hz, 1H), 7.12 (d, J=7.6 Hz, 1H), 6.85 (d, J=8.4 Hz, 1H), 6.57 (dd, J=2.4, 8.4 Hz, 1H), 6.53 (s, 1H), 4.38 (s, 2H), 3.68 (s, 2H), 3.49 (s, 2H), 2.72-2.62 (m, 4H), 2.45 (s, 3H), 2.42 (br. s., 2H), 2.27 (br. s., 2H), 1.68 (br. s., 4H). HRMS calcd. for C$_{33}$H$_{33}$F$_3$N$_5$O$_3$ (M+H) 604.2535 found 604.2563.

Example 6

The following compounds were prepared with similar methods as described for Example 5 using the appropriate starting materials.

| Example | Structure/Name | Starting Materials | Analytical Data |
| --- | --- | --- | --- |
| 6-1 | 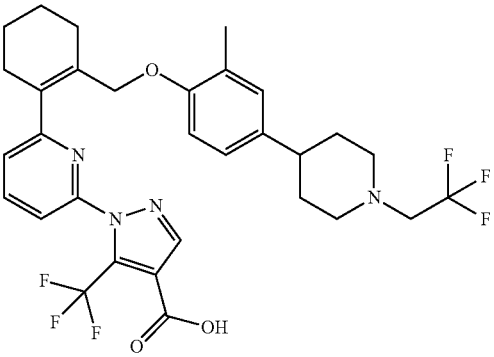<br>1-(6-(2-((2-Methyl-4-(1-(2,2,2-trifluoroethyl)piperidin-4-yl)phenoxy)methyl)cyclohex-1-en-1-yl)pyridin-2-yl)-5-(trifluoromethyl)-1H-pyrazole-4-carboxylic acid | Example 1-B and 2,2,2-trifluoroethyl trifluoromethane-sulfonate (CAS # 6226-25-1) | $^1$H NMR (400 MHz, DMSO-$d_6$) δ 8.01 (t, J = 7.9 Hz, 1H), 7.91 (br. s., 1H), 7.60 (d, J = 7.7 Hz, 1H), 7.41 (d, J = 7.6 Hz, 1H), 7.00 (d, J = 2.1 Hz, 1H), 6.89 (dd, J = 2.2, 8.4 Hz, 1H), 6.60 (d, J = 8.4 Hz, 1H), 4.40 (s, 2H), 3.16 (q, J = 10.3 Hz, 2H), 2.97 (d, J = 11.5 Hz, 2H), 2.44 (br. s., 2H), 2.41-2.35 (m, 2H), 2.31 (br. s., 2H), 2.12 (s, 3H), 1.70 (br. s., 4H), 1.64-1.54 (m, 4H). HRMS calcd. for $C_{31}H_{33}F_6N_4O_3$ (M + H) 623.2457, found 623.2485. |
| 6-2 | 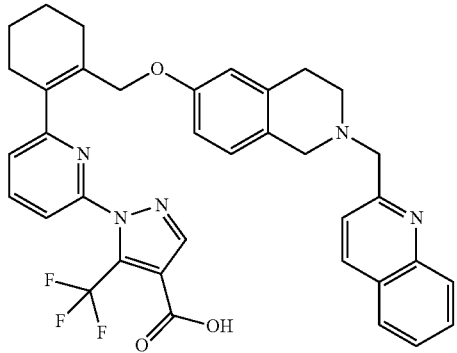<br>1-(6-(2-(((2-(Quinolin-2-ylmethyl)-1,2,3,4-tetrahydro-isoquinolin-6-yl)oxy)methyl)cyclohex-1-en-1-yl)pyridin-2-yl)-5-(trifluoromethyl)-1H-pyrazole-4-carboxylic acid | Example 5-B, and 2-(chloro-methyl)quinoline hydrochloride (CAS # 3747-74-8) | $^1$H NMR (400 MHz, DMSO-$d_6$) δ 8.33 (d, J = 8.4 Hz, 1H), 8.05-7.93 (m, 3H), 7.87 (br. s., 1H), 7.74 (ddd, J = 1.4, 6.9, 8.4 Hz, 1H), 7.66 (d, J = 8.4 Hz, 1H), 7.59 (d, J = 8.1 Hz, 2H), 7.40 (d, J = 7.6 Hz, 1H), 6.85 (d, J = 8.4 Hz, 1H), 6.58 (dd, J = 2.6, 8.3 Hz, 1H), 6.55 (d, J = 2.4 Hz, 1H), 4.38 (s, 2H), 3.91 (s, 2H), 3.53 (s, 2H), 2.72 (m., 4H), 2.43 (br. s., 2H), 2.27 (br. s., 2H), 1.68 (br. s., 4H). HRMS calcd. for $C_{36}H_{33}F_3N_5O_3$ (M + H) 640.2535 found 640.2568. |
| 6-3 | 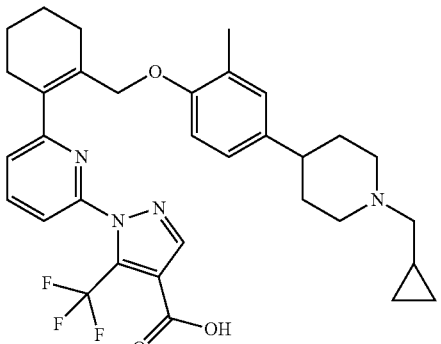<br>1-(6-(2-((4-(1-(Cyclopropylmethyl)piperidin-4-yl)-2-methylphenoxy)methyl)cyclohex-1-en-1-yl)pyridin-2-yl)-5-(trifluoromethyl)-1H-pyrazole-4-carboxylic acid | Example 1-B and (bromo-methyl)cyclo propane (CAS # 7051-34-5) | $^1$H NMR (400 MHz, CD$_3$OD) δ 7.95 (app. t, J = 7.8 Hz, 1H), 7.92 (s, 1H), 7.60 (dd, J = 0.7, 8.0 Hz, 1H), 7.36 (dd, J = 0.7, 7.8 Hz, 1H), 6.90-6.94 (m, 1H), 6.74-6.80 (m, 1H), 6.65 (d, J = 8.4 Hz, 1H), 4.46 (s, 2H), 3.61-3.72 (m, 2H), 2.93-3.08 (m, 4H), 2.62-2.73 (m, 1H), 2.44 (br. s., 2H), 2.29 (br. s., 2H), 2.13 (s, 3H), 1.83-2.04 (m, 4H), 1.69-1.79 (m, 4H), 1.10-1.23 (m, 1H), 0.73-0.81 (m, 2H), 0.41-0.50 (m, 2H) HRMS calcd. for $C_{33}H_{38}F_3N_4O_3$ (M + H) 595.2896, found 595.2922. |

Example 7

Example 7-A. Ethyl 1-(6-(2-((4-(1-(cyclopropanecarbonyl)piperidin-4-yl)-3-ethylphenoxy)methyl)cyclohex-1-en-1-yl)pyridin-2-yl)-5-(trifluoromethyl)-1H-pyrazole-4-carboxylate

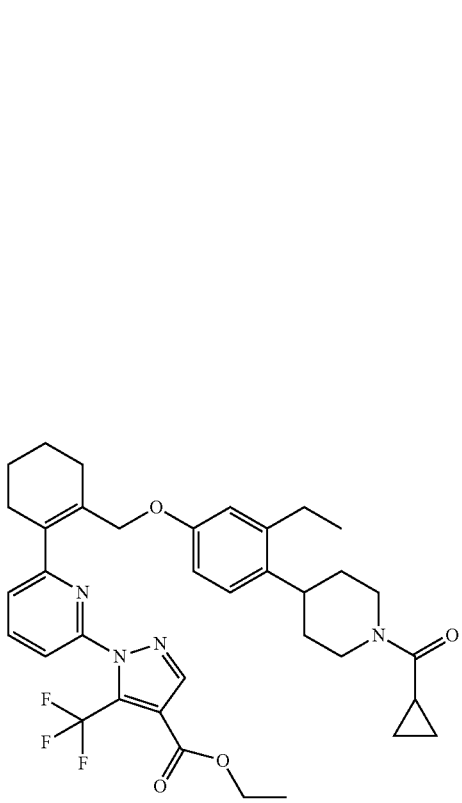 [SMILES: CCOC(=O)c1cnn(-c2cccc(C3=C(COc4ccc(C5CCN(C(=O)C6CC6)CC5)c(CC)c4)CCCC3)n2)c1C(F)(F)F]

DIAD (0.031 mL, 0.160 mmol) was added dropwise to a THF (5 mL) solution of Intermediate 9 (55.7 mg, 0.141 mmol), Intermediate 2-5-1 (35 mg, 0.128 mmol) and PPh$_3$ (42.0 mg, 0.160 mmol) at rt. The mixture was stirred for 2 h and then concentrated. The residue was purified by silica gel flash column chromatography (heptane to 50% EtOAc in heptane) to afford the title compound. MS (ESI+) m/z 651.5 (M+H).

Example 7. 1-(6-(2-((4-(1-(Cyclopropanecarbonyl)piperidin-4-yl)-3-ethylphenoxy)methyl)cyclohex-1-en-1-yl)pyridin-2-yl)-5-(trifluoromethyl)-1H-pyrazole-4-carboxylic acid

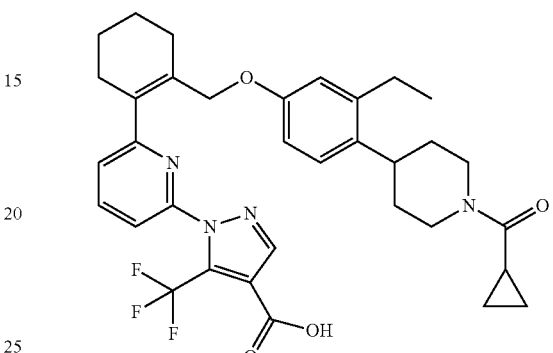

1 M aqueous NaOH (0.6 mL, 0.60 mmol) was added to a solution of Example 7-A (64 mg, 0.098 mmol) in THF (2 mL) and MeOH (2 mL). The mixture was then stirred at 50° C. for 3 h, then at rt for 16 h. The reaction mixture was diluted with water, and then rendered acidic by the addition of 10% citric acid until pH 6. The mixture was diluted with EtOAc and water. The organic phase was separated, and then washed with water (twice), then brine, dried over sodium sulfate, filtered, and then concentrated. The resulting residue was triturated with acetonitrile, and then the resulting solid was collected by filtration to afford the title compound. $^1$H NMR (400 MHz, DMSO-d6) δ 13.42 (br. s., 1H), 8.27 (br. s., 1H), 8.08 (t, J=7.89 Hz, 1H), 7.67 (d, J=7.82 Hz, 1H), 7.49 (d, J=7.70 Hz, 1H), 7.03 (d, J=8.93 Hz, 1H), 6.57-6.61 (m, 2H), 4.50 (d, J=11.37 Hz, 1H), 4.31-4.41 (m, 3H), 3.11-3.22 (m, 1H), 2.90 (tt, J=3.45, 11.83 Hz, 1H), 2.54-2.64 (m, 2H), 2.42 (br. s., 2H), 2.27 (br. s., 2H), 1.95-2.03 (m, 1H), 1.62-1.72 (m, 4H), 1.49-1.62 (m, 2H), 1.34-1.45 (m, 1H), 1.08 (t, J=7.52 Hz, 3H), 0.65-0.79 (m, 4H). HRMS calcd. for C$_{34}$H$_{38}$F$_3$N$_4$O$_4$ 623.2845 (M+H), found 623.2904.

Example 8

The following compounds were prepared with similar methods as described above for Example 7 using the appropriate starting materials.

| Example | Structure/Name | Starting Materials | Analytical Data |
|---|---|---|---|
| 8-1 | 1-(6-(2-((4-(1-(Cyclopropanecarbonyl)piperidin-4-yl)-2-ethylphenoxy)methyl)cyclohex-1-en-1-yl)pyridin-2-yl)-5-(trifluoromethyl)-1H-pyrazole-4-carboxylic acid | Intermediate 9 and Intermediate 2-5-2 | $^1$H NMR (400 MHz, CD$_3$OD) δ 8.14 (s, 1H), 7.98 (t, J = 7.8 Hz, 1H), 7.58 (dd, J = 8.0, 0.8 Hz, 1H), 7.47 (dd, J = 7.7, 0.8 Hz, 1H), 6.98 (d, J = 2.2 Hz, 1H), 6.88 (dd, J = 8.4, 2.3 Hz, 1H), 6.59 (d, J = 8.4 Hz, 1H), 4.62 (d, J = 11.1 Hz, 1H), 4.49-4.37 (m, 3H), 3.18-3.26 (m, 1H), 2.67-2.78 (m, 2H), 2.60 (q, J = 7.5 Hz, 2H), 2.45-2.54 (m, 2H), 2.34-2.41 (m, 2H), 1.95-2.04 (m, 1H), 1.90 (d, J = 12.7 Hz, 1H), 1.73-1.85 (m, 5H), 1.44-1.69 (m, 2H), 1.16 (t, J = 7.5 Hz, 3H), 0.75-0.93 (m, 4H). HRMS calcd. for C$_{34}$H$_{38}$F$_3$N$_4$O$_4$ (M + H) 623.2845 found 623.2863 (M + H) |
| 8-2 | 1-(6-(2-(((2-(Pyridin-2-ylmethyl)-1,2,3,4-tetrahydro-isoquinolin-6-yl)oxy)methyl)cyclohex-1-en-1-yl)pyridin-2-yl)-5-(trifluoromethyl)-1H-pyrazole-4-carboxylic acid | Intermediate 9 and Intermediate 3-2 | $^1$H NMR (400 MHz, DMSO-d$_6$) δ 13.37 (br. s., 1H), 8.50 (dd, J = 0.7, 4.8 Hz, 1H), 8.25 (s, 1H), 8.08 (t, J = 7.9 Hz, 1H), 7.77 (dt, J = 1.7, 7.6 Hz, 1H), 7.67 (d, J = 7.8 Hz, 1H), 7.49 (d, J = 7.7 Hz, 1H), 7.46 (d, J = 7.8 Hz, 1H), 7.27 (dd, J = 5.1, 6.5 Hz, 1H), 6.85 (d, J = 8.4 Hz, 1H), 6.57 (dd, J = 2.5, 8.4 Hz, 1H), 6.53 (d, J = 2.3 Hz, 1H), 4.38 (s, 2H), 3.75 (s, 2H), 3.51 (s, 2H), 2.68 (dd, J = 3.8, 7.5 Hz, 4H), 2.41 (br. s., 2H), 2.27 (br. s., 2H), 1.68 (br. s., 4H). HRMS calcd. for C$_{32}$H$_{31}$F$_3$N$_5$O$_3$ (M + H) 590.2379, found 590.2405. |

Example 9

Example 9-A. Ethyl 1-(6-(2-(((tert-butyldimethylsilyl)oxy)methyl)cyclohex-1-en-1-yl)pyridin-2-yl)-5-ethyl-1H-pyrazole-4-carboxylate

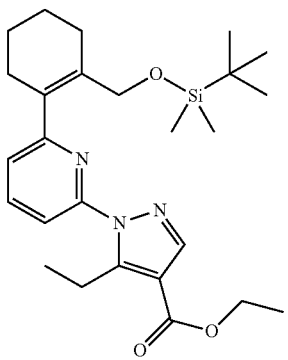 [SMILES: CCOC(=O)c1cnn(-c2cccc(C3=C(CO[Si](C)(C)C(C)(C)C)CCCC3)n2)c1CC]

To a suspension of Intermediate 1-3 (584 mg, 1.801 mmol), bis(pinacolato)diboron (457 mg, 1.801 mmol), KOAc (321 mg, 3.28 mmol) in dioxane (8.2 mL) was added chloro(2-dicyclohexylphosphino-2',6'-dimethoxy-1,1'-biphenyl)[2-(2-aminoethylphenyl)]palladium(II) methyl-t-butylether adduct (CAS #1028206-58-7, 55.1 mg, 0.082 mmol). The mixture was then stirred at 120° C. under microwave irradiation for 30 min. To the reaction mixture was then added a solution of Intermediate 4 (500 mg, 1.638 mmol) in dioxane (8.2 mL), followed by 2M aq. potassium phosphate (2.4 mL, 4.91 mmol), Pd(dppf)Cl$_2$·CH$_2$Cl$_2$ (66.9 mg, 0.082 mmol). The mixture was then stirred at 110° C. under microwave irradiation for 30 min. The organic phase was then separated, and then concentrated onto Celite®. The resulting residue was purified by silica gel flash column chromatography (0-20% EtOAc/heptane) to afford the title compound. MS (ESI+) m/z 470.7 (M+H).

Example 9-B. Ethyl 5-ethyl-1-(6-(2-(hydroxymethyl)cyclohex-1-en-1-yl)pyridin-2-yl)-1H-pyrazole-4-carboxylate

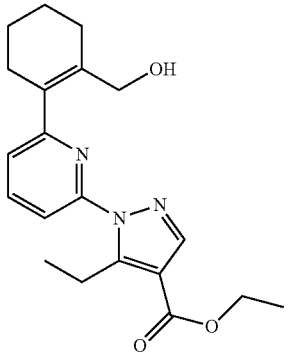 [SMILES: CCOC(=O)c1cnn(-c2cccc(C3=C(CO)CCCC3)n2)c1CC]

TBAF (1 M in THF, 478 μl, 0.478 mmol) was added to a THF (4.5 mL) solution of Example 9-A (214 mg, 0.456 mmol) at 0° C. The solution was stirred at 0° C. for 1 h, and then warmed to rt for 1 h. The reaction mixture was then diluted with EtOAc and 1/1 water:saturated. aq. sodium bicarbonate. The organic layer was then separated, and then washed with brine, dried over sodium sulfate, filtered, and then concentrated to furnish the title compound. MS (ESI+) m/z 356.4 (M+H).

Example 9-C. Ethyl 1-(6-(2-((4-(1-(cyclopropanecarbonyl)piperidin-4-yl)-2-methylphenoxy)methyl)cyclohex-1-en-1-yl)pyridin-2-yl)-5-ethyl-1H-pyrazole-4-carboxylate

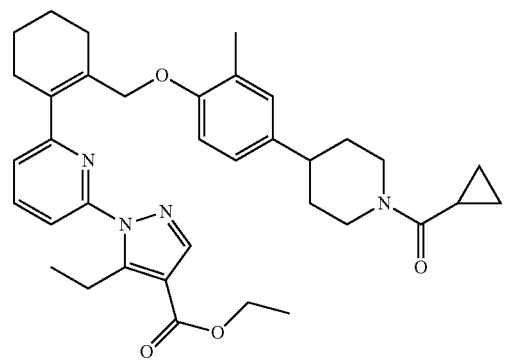 [SMILES: CCOC(=O)c1cnn(-c2cccc(C3=C(COc4ccc(C5CCN(C(=O)C6CC6)CC5)cc4C)CCCC3)n2)c1CC]

To a solution of Example 9-B (162 mg, 0.456 mmol), Intermediate 2-1 (118 mg, 0.456 mmol) and PPh$_3$ (143 mg, 0.547 mmol) in THF (2.28 mL), DIAD (106 μl, 0.547 mmol) was added at rt. The mixture was then stirred for 1 h, and then diluted with DCM and water. The mixture was then passed through an ISOLUTE® Phase Separator. The organic phase was then concentrated onto Celite®. The resulting residue was purified by silica gel flash column chromatography (heptane/EtOAc=100/0 to 50/50) to afford the title compound. MS (ESI+) m/z 597.5 (M+H).

Example 9. 1-(6-(2-((4-(1-(Cyclopropanecarbonyl)piperidin-4-yl)-2-methylphenoxy)methyl)cyclohex-1-en-1-yl)pyridin-2-yl)-5-ethyl-1H-pyrazole-4-carboxylic acid

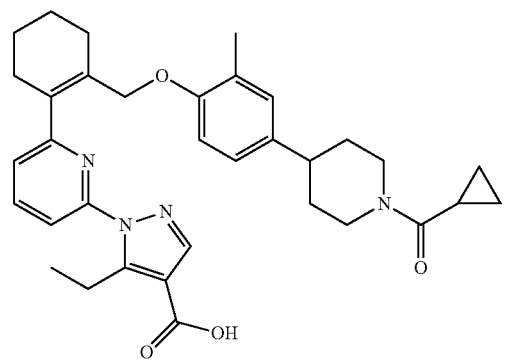 [SMILES: CCc1c(C(=O)O)cnn1-c1cccc(C2=C(COc3ccc(C4CCN(C(=O)C5CC5)CC4)cc3C)CCCC2)n1]

To a solution of Example 9-C (148 mg, 0.186 mmol) in MeOH (2.5 mL) and THF (2.5 mL) was added 1 M aq. LiOH (2.42 mL, 2.42 mmol). The mixture was then stirred at 50° C. for 5 h, and the cooled to room temperature. The reaction mixture was rendered acidic by the addition of 1 M HCl (ca. 2.5 mL), and then extract with EtOAc. The organic layer was separated and then concentrated. The resulting residue was purified by SFC (Princeton, 2-ethylpyridine 21×150 mm 5 um, MeOH w/NH₄OH modifier) to afford the title compound. ¹H NMR (400 MHz, CD₃OD) δ 7.99 (s, 1H), 7.95-7.87 (m, 1H), 7.64 (dd, J=8.1, 0.8 Hz, 1H), 7.33 (dd, J=7.7, 0.9 Hz, 1H), 6.96 (d, J=2.2 Hz, 1H), 6.85 (dd, J=8.3, 2.3 Hz, 1H), 6.55 (d, J=8.4 Hz, 1H), 4.61 (d, J=13.0 Hz, 1H), 4.43 (s, 3H), 3.35 (d, J=7.4 Hz, 2H), 3.27-3.17 (m, 1H), 2.77-2.63 (m, 2H), 2.51 (t, J=4.6 Hz, 2H), 2.38 (dd, J=6.7, 3.8 Hz, 2H), 2.15 (s, 3H), 1.98 (tt, J=7.9, 4.8 Hz, 1H), 1.83-1.74 (m, 6H), 1.66-1.41 (m, 2H), 1.19 (t, J=7.3 Hz, 3H), 0.92-0.84 (m, 2H), 0.84-0.75 (m, 2H). HRMS calcd for $C_{34}H_{41}N_4O_4$ (M+H)⁺ 569.3050, found 569.3129.

Example 10

Example 10-A. Ethyl 1-(6'-((4-(1-(cyclopropanecarbonyl)piperidin-4-yl)-2-methylphenoxy)methyl)-2',3',4',5'-tetrahydro-[1,1'-biphenyl]-3-yl)-5-(trifluoromethyl)-1H-pyrazole-4-carboxylate

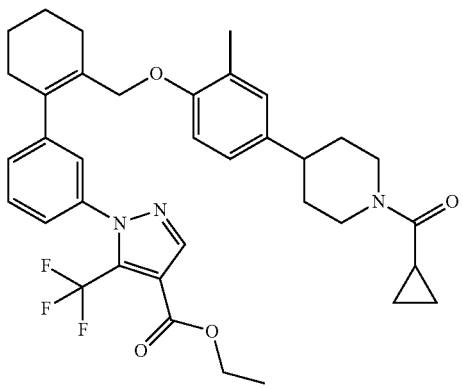 [SMILES: CCOC(=O)c1cnn(-c2cccc(C3=C(COc4ccc(C5CCN(C(=O)C6CC6)CC5)cc4C)CCCC3)c2)c1C(F)(F)F]

To a suspension of Intermediate 1-4 (70.0 mg, 0.171 mmol), Intermediate 5-1 (107 mg, 0.171 mmol), and Cs₂CO₃ (167 mg, 0.512 mmol) in dioxane (2.1 mL) and DMF (348 µl), and water (50 µL) was added chloro(2-dicyclohexylphosphino-2',6'-dimethoxy-1,1'-biphenyl)[2-(2-aminoethylphenyl)]palladium(II)-methyl-t-butyl ether adduct (CAS #1028206-58-7, 5.74 mg, 8.53 µmol). The mixture was then stirred at 110° C. under microwave irradiation for 1 h. The reaction mixture was diluted with EtOAc and water. The organic phase was separated, and then concentrated onto Celite®. The resulting residue was purified by silica gel flash column chromatography (0-50% EtOAc in heptane) to afford the title compound. MS (ESI+) m/z 636.2 (M+H).

Example 10. 1-(6'-((4-(1-(Cyclopropanecarbonyl)piperidin-4-yl)-2-methylphenoxy)methyl)-2',3',4',5'-tetrahydro-[1,1'-biphenyl]-3-yl)-5-(trifluoromethyl)-1H-pyrazole-4-carboxylic acid

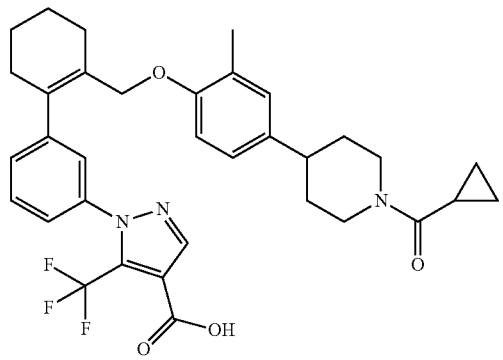 [SMILES: Cc1cc(C2CCN(C(=O)C3CC3)CC2)ccc1OCC1=C(c2cccc(-n3ncc(C(=O)O)c3C(F)(F)F)c2)CCCC1]

Example 10-A (38 mg, 0.060 mmol) was dissolved in MeOH (0.6 mL) and THF (0.6 mL) and LiOH (2M in water, 149 µl, 0.299 mmol) was stirred at rt for 16 h. The reaction mixture was rendered acidic by the addition of 1 M HCl (ca. 0.3 mL), and then and extract with EtOAc. The organic layer was separated and then concentrated. The resulting residue was purified by RP-HPLC (HC-C) to afford the title compound. ¹H NMR (400 MHz, CD₃OD) δ 8.04 (d, J=0.7 Hz, 1H), 7.49 (t, J=7.8 Hz, 1H), 7.37 (dt, J=7.8, 1.4 Hz, 1H), 7.34 (ddd, J=7.9, 2.2, 1.1 Hz, 1H), 7.23 (t, J=1.8 Hz, 1H), 6.92 (d, J=2.3 Hz, 1H), 6.86 (dd, J=8.4, 2.3 Hz, 1H), 6.50 (d, J=8.3 Hz, 1H), 4.61 (d, J=13.1 Hz, 1H), 4.43 (d, J=13.5 Hz, 1H), 4.29 (s, 2H), 3.27-3.17 (m, 1H), 2.77-2.63 (m, 2H), 2.43-2.31 (m, 4H), 2.12 (s, 3H), 2.05-1.95 (m, 1H), 1.87 (d, J=13.5 Hz, 1H), 1.78 (m, 5H), 1.67-1.41 (m, 2H), 0.93-0.77 (m, 4H). HRMS calcd for $C_{34}H_{36}F_3N_3O_4$ (M+H)+ 608.2658, found 608.2673.

Example 11. 1-(6-(2-((4-(1-(2-Aminoacetyl)piperidin-4-yl)-2-methylphenoxy)methyl)cyclohex-1-en-1-yl)pyridin-2-yl)-5-(trifluoromethyl)-1H-pyrazole-4-carboxylic acid

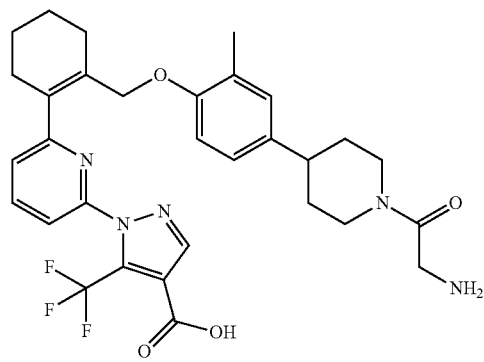 [SMILES: Cc1cc(C2CCN(C(=O)CN)CC2)ccc1OCC1=C(c2cccc(-n3ncc(C(=O)O)c3C(F)(F)F)n2)CCCC1]

The title compound was synthesized starting from Example 1-B. To a solution of Example 1-B (21 mg, 0.030 mmol) in DCM (0.5 mL) was DIPEA (0.015 mL, 0.089 mmol) followed by N-Boc glycine (CAS #4530-20-5, 7.76 mg, 0.044 mmol) and HATU (12 mg, 0.032 mmol). The reaction mixture was stirred at room temperature for approximately 15 h at which time the mixture was charged with additional HATU (3 mg, 0.008 mmol) and stirred for an additional 2 h. The mixture was then concentrated to near dryness and the resulting residue diluted with 1,4-dioxane (0.5 mL) and charged with 2N aqueous LiOH. The mixture was then heated at 50° C. for approximately 30 minutes. The mixture was then acidified by the slow addition of 1N aqueous HCl and further diluted with DCM and water, the resulting mixture was passed through a ISOLUTE® Phase Separator and the organic eluent is collected and concentrated. The resulting residue is dissolved in DCM (1 mL), cooled to 0° C. and charged with TFA (0.3 mL) and stirred for 15 minutes at which time the mixture was concentrated to dryness and purified via RP-HPLC (HC-B) to furnish the title compound. $^1$H NMR (400 MHz, DMSO-d$_6$) δ 8.48 (br. s., 1H), 8.05 (t, J=7.8 Hz, 1H), 7.83 (s, 1H), 7.66 (dd, J=0.6, 7.9 Hz, 1H), 7.37 (dd, J=0.6, 7.6 Hz, 1H), 6.91 (d, J=8.6 Hz, 1H), 6.84 (d, J=1.8 Hz, 1H), 6.59-6.53 (m, 1H), 4.45-4.37 (m, 2H), 4.35-4.22 (m, 2H), 3.78 (d, J=13.6 Hz, 1H), 3.60 (d, J=15.5 Hz, 1H), 3.51-3.45 (m, 1H), 3.10-2.99 (m, 2H), 2.64-2.57 (m, 2H), 2.30 (br. s., 2H), 2.15 (br. s., 2H), 2.05 (s, 3H), 1.85-1.72 (m, 1H), 1.71-1.61 (m, 4H), 1.60-1.53 (m, 2H), 1.15 (dq, J=4.2, 12.5 Hz, 1H). HRMS calcd. for $C_{31}H_{35}F_3N_5O_4$ (M+H) 598.2641, found 598.2657.

Example 12

Example 12-A. (±)-Ethyl 1-(6-(2-(((tert-butyldimethylsilyl)oxy)methyl)-5-methylcyclohex-1-en-1-yl)pyridin-2-yl)-5-(trifluoromethyl)-1H-pyrazole-4-carboxylate

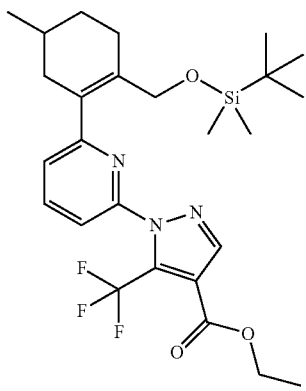 [SMILES: CCOC(=O)c1cnn(-c2cccc(C3=C(CO[Si](C)(C)C(C)(C)C)CCC(C)C3)n2)c1C(F)(F)F]

A mixture of Intermediate 1-1 (2.40 g, 6.59 mmol), bis(pinacolato)diboron (1.84 g, 7.25 mmol), chloro(2-dicyclohexylphosphino-2',6'-dimethoxy-1,1'-biphenyl)[2-(2-aminoethylphenyl)]palladium(II) methyl-t-butylether adduct (0.089 g, 0.132 mmol), and KOAc (0.97 g, 9.89 mmol) in dioxane (60 mL) was stirred at 110° C. for 2.25 h. To the mixture was then added chloro(2-dicyclohexylphosphino-2',6'-dimethoxy-1,1'-biphenyl)[2-(2-aminoethylphenyl)]palladium(II) methyl-t-butylether adduct (0.089 g, 0.132 mmol). The mixture was then stirred for 1 h and then cooled to 65° C. The reaction mixture was added via cannula to a solution of Intermediate 6 (3.33 g, 8.57 mmol), chloro(2-dicyclohexylphosphino-2',6'-dimethoxy-1,1'-biphenyl)[2-(2-aminoethylphenyl)]palladium(II) methyl-t-butylether adduct (0.222 g, 0.330 mmol), and Na$_2$CO$_3$ (2 M in H$_2$O, 6.59 mL, 13.2 mmol). The whole mixture was then stirred at 100° C. for 16 h. The reaction mixture was concentrated with silica gel. The resulting residue was purified by silica gel flash column chromatography (0-5% acetone in heptane) to afford the title compound. MS (ESI+) m/z (M+H) 524.2.

Example 12-B. (±)-Ethyl 1-(6-(2-(hydroxymethyl)-5-methylcyclohex-1-en-1-yl)pyridin-2-yl)-5-(trifluoromethyl)-1H-pyrazole-4-carboxylate

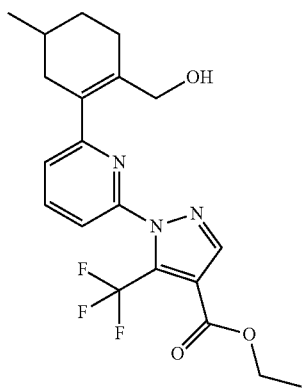 [SMILES: CCOC(=O)c1cnn(-c2cccc(C3=C(CO)CCC(C)C3)n2)c1C(F)(F)F]

To a solution of Example 12-A (0.720 g, 1.37 mmol) in THF (10 mL) was added a solution of TBAF (2.1 mL, 2.1 mmol, 1 M THF). The mixture was then stirred at rt for 1 h, and then concentrated. The resulting residue was then dissolved in EtOAc. The organic layer was then washed with brine, dried over sodium sulfate, filtered and then concentrated. The resulting residue was purified by silica gel flash column chromatography (0-50% EtOAc in heptane) to afford the title compound. MS (ESI+) m/z 410.3 (M+H).

Example 12-C. (±)-Ethyl 1-(6-(2-((4-(1-(cyclopropanecarbonyl)piperidin-4-yl)-2-methylphenoxy)methyl)-5-methylcyclohex-1-en-1-yl)pyridin-2-yl)-5-(trifluoromethyl)-1H-pyrazole-4-carboxylate

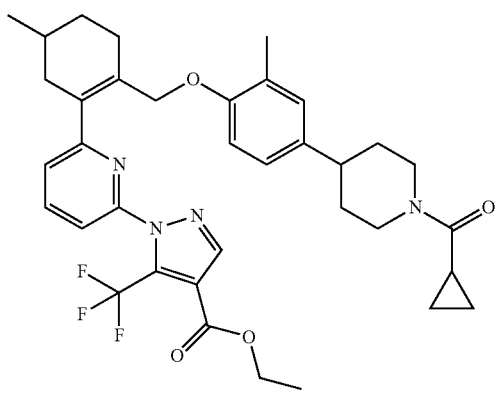 [SMILES: CCOC(=O)c1cnn(-c2cccc(C3=C(COc4ccc(C5CCN(C(=O)C6CC6)CC5)cc4C)CCC(C)C3)n2)c1C(F)(F)F]

The title compound was synthesized in a similar manner to the preparation of Example 7 starting from Example 12-B using Intermediate 2-1. MS (ESI+) m/z (M+H) 651.2.

Example 12a. (±)-1-(6-(2-((4-(1-(cyclopropanecarbonyl)piperidin-4-yl)-2-methylphenoxy)methyl)-5-methylcyclohex-1-en-1-yl)pyridin-2-yl)-5-(trifluoromethyl)-1H-pyrazole-4-carboxylic acid Example 12b. (+)-1-(6-(2-((4-(1-(cyclopropanecarbonyl)piperidin-4-yl)-2-methylphenoxy)methyl)-5-methylcyclohex-1-en-1-yl)pyridin-2-yl)-5-(trifluoromethyl)-1H-pyrazole-4-carboxylic acid and (−)-1-(6-(2-((4-(1-(cyclopropanecarbonyl)piperidin-4-yl)-2-methylphenoxy)methyl)-5-methylcyclohex-1-en-1-yl)pyridin-2-yl)-5-(trifluoromethyl)-1H-pyrazole-4-carboxylic acid

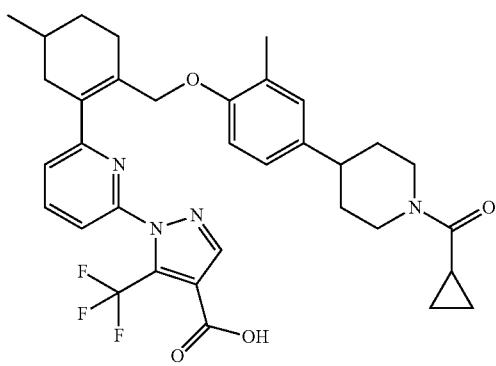 [SMILES: Cc1cc(C2CCN(C(=O)C3CC3)CC2)ccc1OCC1=C(c2cccc(-n3ncc(C(=O)O)c3C(F)(F)F)n2)CC(C)CC1]

Resolution of the enantiomers of (±)-1-(6-(2-((4-(1-(cyclopropanecarbonyl)piperidin-4-yl)-2-methylphenoxy)methyl)-5-methylcyclohex-1-en-1-yl)pyridin-2-yl)-5-(trifluoromethyl)-1H-pyrazole-4-carboxylic acid was achieved by chiral SFC using a CHIRALPAK® AS-H column with 15% MeOH in CO2 to afford (+)-1-(6-(2-((4-(1-(cyclopropanecarbonyl)piperidin-4-yl)-2-methylphenoxy)methyl)-5-methylcyclohex-1-en-1-yl)pyridin-2-yl)-5-(trifluoromethyl)-1H-pyrazole-4-carboxylic acid (enantiomer-1, $t_r$=2.7 min) and (−)-1-(6-(2-((4-(1-(cyclopropanecarbonyl)piperidin-4-yl)-2-methylphenoxy)methyl)-5-methylcyclohex-1-en-1-yl)pyridin-2-yl)-5-(trifluoromethyl)-1H-pyrazole-4-carboxylic acid (enantiomer-2, $t_r$=3.23 min).

To a mixture of Example 12-C (0.061 g, 0.094 mmol) in THF (2 mL)/MeOH (1 mL)/water (1 mL) was added LiOH.H$_2$O (0.071 g, 1.687 mmol). The mixture was then stirred at rt for 3 h. The reaction mixture was rendered acidic by the addition of 3 M aq. HCl (~pH=3). The mixture was then diluted with EtOAc and water. The organic layer was then separated. The aqueous layer was then extracted twice with EtOAc. The combined organic layers were dried over sodium sulfate, filtered and concentrated. The resulting residue was purified by silica gel flash column chromatography (5-20% MeOH in DCM) to afford the title compound. $^1$H NMR (400 MHz, CD$_3$OD) δ 7.99 (s, 1H), 7.94 (t, J=7.8 Hz, 1H), 7.56 (dd, J=8.0, 0.8 Hz, 1H), 7.40 (dd, J=7.7, 0.9 Hz, 1H), 6.96 (d, J=2.3 Hz, 1H), 6.87 (dd, J=8.4, 2.3 Hz, 1H), 6.56 (d, J=8.4 Hz, 1H), 4.62 (d, J=13.0 Hz, 1H), 4.48-4.37 (m, 3H), 3.28-3.17 (m, 1H), 2.76-2.61 (m, 3H), 2.52-2.43 (m, 1H), 2.41-2.28 (m, 1H), 2.16 (s, 3H), 2.08-1.94 (m, 2H), 1.82 (dd, J=23.0, 12.4 Hz, 4H), 1.67-1.43 (m, 2H), 1.37 (ddd, J=12.4, 9.1, 5.5 Hz, 1H), 1.04 (d, J=6.4 Hz, 3H), 0.93-0.76 (m, 4H); HRMS; calcd. for C$_{34}$H$_{38}$F$_3$N$_4$O$_4$ (M+H) 623.2845, found 623.2882.

Example 13

Example 13-A. (±)-Ethyl 1-(6-(2-(((tert-butyldimethylsilyl)oxy)methyl)-3-methylcyclohex-1-en-1-yl)pyridin-2-yl)-5-(trifluoromethyl)-1H-pyrazole-4-carboxylate

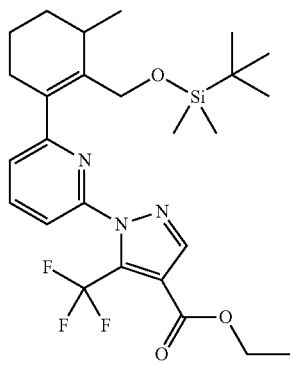 [SMILES: CCOC(=O)c1cnn(-c2cccc(C3=C(CO[Si](C)(C)C(C)(C)C)C(C)CCC3)n2)c1C(F)(F)F]

To a mixture of Intermediate 1-1 (2.81 g, 7.72 mmol) and bis(pinacolato)diboron (2.16 g, 8.49 mmol) in dioxane (50 mL), was added potassium acetate (1.14 g, 11.6 mmol), followed by chloro(2-dicyclohexylphosphino-2',6'-dimethoxy-1,1'-biphenyl)[2-(2-aminoethylphenyl)]palladium(II) methyl-t-butylether adduct (0.10 g, 0.15 mmol). The mixture was stirred at 110° C. for 20 h. To the reaction mixture were added (±)-2-(((tert-Butyldimethylsilyl)oxy)methyl)-3-methylcyclohex-1-en-1-yl trifluoromethanesulfonate (Intermediate 7) (3.0 g, 7.72 mmol), chloro(2-dicyclohexylphosphino-2',6'-dimethoxy-1,1'-biphenyl)[2-(2-aminoethylphenyl)]palladium(II) methyl-t-butylether adduct (0.26 g, 0.386 mmol), dioxane (50 mL) and then 1 M aq. $Na_2CO_3$ (15.5 mL, 15.5 mmol). The mixture was then stirred at 100° C. for 20 h, and then cooled to room temperature. The reaction mixture was then diluted with EtOAc, and then washed with water (×2) and brine. The aqueous layer was then extracted with EtOAc, which was then washed with water and brine. The combined organic layers were dried over sodium sulfate, filtered, and then concentrated. The resulting residue was purified by silica gel flash column chromatography (0-100% EtOAc in heptane) to afford the title compound. MS (ESI+) m/z 524.3 (M+H).

Example 13-B. (±)-Ethyl 1-(6-(2-(hydroxymethyl)-3-methylcyclohex-1-en-1-yl)pyridin-2-yl)-5-(trifluoromethyl)-1H-pyrazole-4-carboxylate

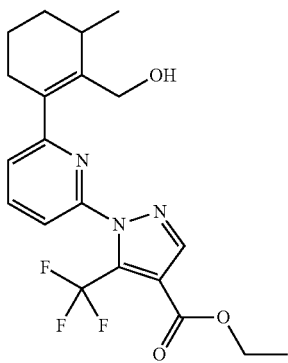 [SMILES: CCOC(=O)c1cnn(-c2cccc(C3=C(CO)C(C)CCC3)n2)c1C(F)(F)F]

TBAF (1M in THF, 2.9 mL, 2.9 mmol, 1 M) was added to a THF (19 mL) solution of Example 13-A (1.0 g, 1.93 mmol) at rt. The mixture was stirred at rt for 3 h, and then diluted with EtOAc and water. The organic layer was separated, and then washed with water, and then brine, dried over sodium sulfate, filtered and concentrated. The resulting residue was purified by silica gel flash column chromatography (0-100% EtOAc in heptane) to afford the title compound. MS (ESI+) m/z 410.6 (M+H).

Example 13-C(a). (±)-Ethyl 1-(6-(2-((4-(1-(cyclopropanecarbonyl)piperidin-4-yl)-3-ethylphenoxy)methyl)-3-methylcyclohex-1-en-1-yl)pyridin-2-yl)-5-(trifluoromethyl)-1H-pyrazole-4-carboxylate

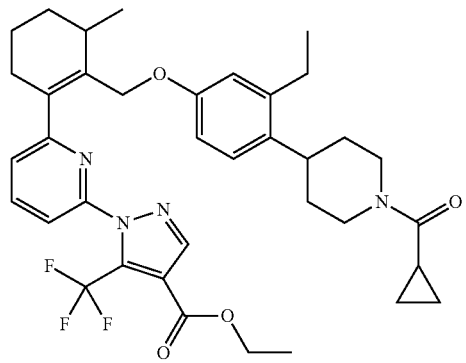 [SMILES: CCOC(=O)c1cnn(-c2cccc(C3=C(COc4ccc(C5CCN(C(=O)C6CC6)CC5)c(CC)c4)C(C)CCC3)n2)c1C(F)(F)F]

To a solution of Intermediate 2-4 (200 mg, 0.74 mmol), Example 13-B (300 mg, 0.74 mmol), and $PPh_3$ (240 mg, 0.93 mmol) in THF (6 mL) was added DIAD (0.2 mL, 0.93 mmol). The mixture was stirred at rt for 1 h, and then diluted with water. The mixture was then extracted with EtOAc. The organic layer was dried over magnesium sulfate, filtered and concentrated. The resulting residue was purified by silica gel flash column chromatography (0-100% EtOAc in heptane) to give the title compound.

Example 13-C(b). (+) or (−)-Ethyl 1-(6-(2-((4-(1-(cyclopropanecarbonyl)piperidin-4-yl)-3-ethylphenoxy)methyl)-3-methylcyclohex-1-en-1-yl)pyridin-2-yl)-5-(trifluoromethyl)-1H-pyrazole-4-carboxylate (enantiomer-1, tr=2.3 min) and (−) or (+)-ethyl 1-(6-(2-((4-(1-(cyclopropanecarbonyl)piperidin-4-yl)-3-ethylphenoxy)methyl)-3-methylcyclohex-1-en-1-yl)pyridin-2-yl)-5-(trifluoromethyl)-1H-pyrazole-4-carboxylate (enantiomer-2, tr=2.5 min)

Resolution of the enantiomers of (±)-ethyl 1-(6-(2-((4-(1-(cyclopropanecarbonyl)piperidin-4-yl)-3-ethylphenoxy)methyl)-3-methylcyclohex-1-en-1-yl)pyridin-2-yl)-5-(trifluoromethyl)-1H-pyrazole-4-carboxylate was achieved by chiral SFC using a CHIRALPAK® AD-H column with 5-55% MeOH in CO2 to afford (+) or (−)-ethyl 1-(6-(2-((4-(1-(cyclopropanecarbonyl)piperidin-4-yl)-3-ethylphenoxy)methyl)-3-methylcyclohex-1-en-1-yl)pyridin-2-yl)-5-(trifluoromethyl)-1H-pyrazole-4-carboxylate (enantiomer-1, tr=2.3 min) and (−) or (+)-ethyl 1-(6-(2-((4-(1-(cyclopropanecarbonyl)piperidin-4-yl)-3-ethylphenoxy)methyl)-3-methylcyclohex-1-en-1-yl)pyridin-2-yl)-5-(trifluoromethyl)-1H-pyrazole-4-carboxylate (enantiomer-2, tr=2.5 min).

Example 13a. (+)-1-(6-(2-((4-(1-(Cyclopropanecarbonyl)piperidin-4-yl)-3-ethylphenoxy)methyl)-3-methylcyclohex-1-en-1-yl)pyridin-2-yl)-5-(trifluoromethyl)-1H-pyrazole-4-carboxylic acid

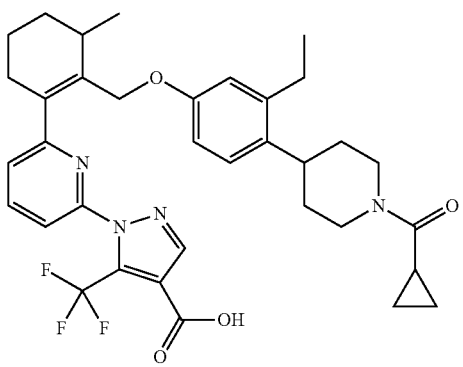 [SMILES: CCc1cc(OCC2=C(c3cccc(-n4ncc(C(=O)O)c4C(F)(F)F)n3)CCCC2C)ccc1C1CCN(C(=O)C2CC2)CC1]

To a solution of (+) or (−)-ethyl 1-(6-(2-((4-(1-(cyclopropanecarbonyl)piperidin-4-yl)-3-ethylphenoxy)methyl)-3-methylcyclohex-1-en-1-yl)pyridin-2-yl)-5-(trifluoromethyl)-1H-pyrazole-4-carboxylate (Example 13-C(b), enantiomer-1, tr=2.3 min) (73 mg, 0.110 mmol) in THF (2 mL)/MeOH (1 mL)/water (1 mL) was added LiOH (26 mg, 1.1 mmol). The mixture as then stirred at rt for 1 h. The reaction mixture was then diluted with water, and then rendered acidic by the addition of 1 M aq. HCl (pH~2). The mixture was extracted with EtOAc. The organic phase was dried over $MgSO_4$, filtered and then concentrated to afford the title compound. $^1$H NMR (400 MHz, $CD_3OD$) δ 8.06 (s, 1H), 7.95 (t, J=7.8 Hz, 1H), 7.56 (dd, J=8.0, 0.9 Hz, 1H), 7.45 (dd, J=7.7, 0.9 Hz, 1H), 6.96-7.05 (m, 1H), 6.52-6.63 (m, 2H), 4.64 (d, J=13.1 Hz, 1H), 4.32-4.54 (m, 3H), 2.93-3.07 (m, 1H), 2.68-2.80 (m, 1H), 2.50-2.67 (m, 4H), 2.31-2.44 (m, 1H), 2.27 (t, J=7.4 Hz, 1H), 1.93-2.06 (m, 1H), 1.46-1.92 (m, 8H), 1.21 (d, J=7.0 Hz, 3H), 1.14 (t, J=7.5 Hz, 3H), 0.75-0.99 (m, 4H). HRMS; calcd. for $C_{35}H_{40}F_3N_4O_4$ (M+H) 637.2996, found 637.3014.

Example 13b. (−)-1-(6-(2-((4-(1-(Cyclopropanecarbonyl)piperidin-4-yl)-3-ethylphenoxy)methyl)-3-methylcyclohex-1-en-1-yl)pyridin-2-yl)-5-(trifluoromethyl)-1H-pyrazole-4-carboxylic acid

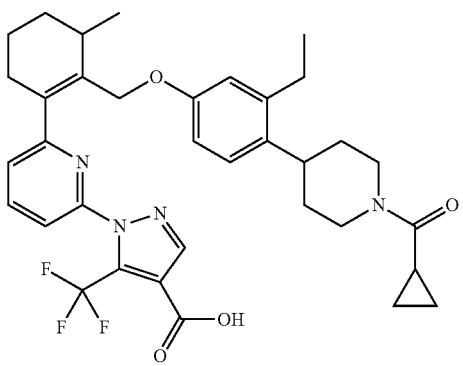 [SMILES: CCc1cc(OCC2=C(c3cccc(-n4ncc(C(=O)O)c4C(F)(F)F)n3)CCCC2C)ccc1C1CCN(C(=O)C2CC2)CC1]

The title compound was synthesized from (−) or (+)-ethyl 1-(6-(2-((4-(1-cyclopropanecarbonyl)piperidin-4-yl)-3-ethylphenoxy)methyl)-3-methylcyclohex-1-en-1-yl)pyridin-2-yl)-5-(trifluoromethyl)-1H-pyrazole-4-carboxylate (Example 13-C(b), (enantiomer-2, tr=2.5 min) analogously to the preparation of Example 13a. $^1$H NMR (400 MHz, $CD_3OD$) δ 8.06 (s, 1H), 7.95 (t, J=7.8 Hz, 1H), 7.56 (dd, J=8.0, 0.9 Hz, 1H), 7.45 (dd, J=7.7, 0.9 Hz, 1H), 6.96-7.05 (m, 1H), 6.52-6.63 (m, 2H), 4.64 (d, J=13.1 Hz, 1H), 4.32-4.54 (m, 3H), 2.93-3.07 (m, 1H), 2.68-2.80 (m, 1H), 2.50-2.67 (m, 4H), 2.31-2.44 (m, 1H), 2.27 (t, J=7.4 Hz, 1H), 1.93-2.06 (m, 1H), 1.46-1.92 (m, 8H), 1.21 (d, J=7.0 Hz, 3H), 1.14 (t, J=7.5 Hz, 3H), 0.75-0.99 (m, 4H). HRMS; calcd. for $C_{35}H_{40}F_3N_4O_4$ (M+H) 637.2996, found 637.3014.

Example 14

Example 14-A. Ethyl 1-(6-(2-(((tert-butyldimethylsilyl)oxy)methyl)-3,3-dimethylcyclohex-1-en-1-yl)pyridin-2-yl)-5-(trifluoromethyl)-1H-pyrazole-4-carboxylate

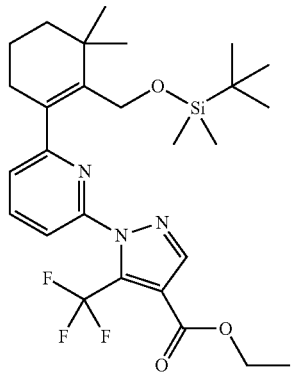 [SMILES: CCOC(=O)c1cnn(-c2cccc(C3=C(CO[Si](C)(C)C(C)(C)C)C(C)(C)CCC3)n2)c1C(F)(F)F]

A suspension of Intermediate 1-1, bis(pinacolato)diboron (2.08 g, 8.20 mmol), potassium acetate (1.10 g, 11.2 mmol) and chloro(2-dicyclohexylphosphino-2',6'-dimethoxy-1,1'-biphenyl)[2-(2-aminoethylphenyl)]palladium(II) methyl-t-butylether adduct (0.100 g, 0.149 mmol) in dioxane (50 mL) was stirred at 110° C. for 3 h. To the reaction mixture was then added Intermediate 8 (3.0 g, 7.45 mmol), chloro(2-dicyclohexylphosphino-2',6'-dimethoxy-1,1'-biphenyl)[2-(2-aminoethylphenyl)]palladium(II) methyl-t-butylether adduct (0.251 g, 0.373 mmol), dioxane (50 mL) and 1 M aq. $Na_2CO_3$ (14.9 mL, 14.9 mmol). The mixture was then stirred at 100° C. for 16 h, and then cooled to rt. The reaction mixture was then diluted with EtOAc and water. The organic layer was separated, and then washed with water and then brine. The aqueous layer was extracted with EtOAc, which was then washed with water and brine. The combined organic layers were dried over sodium sulfate, filtered and then concentrated. The resulting residue was purified by silica gel flash column chromatography (0-100% EtOAc in heptane) to afford the title compound. MS (ESI+) m/z 538.3 (M+H).

Example 14-B. Ethyl 1-(6-(2-(hydroxymethyl)-3,3-dimethylcyclohex-1-en-1-yl)pyridin-2-yl)-5-(trifluoromethyl)-1H-pyrazole-4-carboxylate

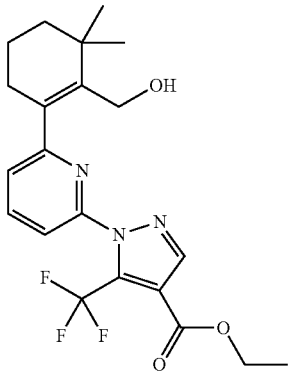 [SMILES: CCOC(=O)c1cnn(-c2cccc(C3=C(CO)C(C)(C)CCC3)n2)c1C(F)(F)F]

TBAF (1 M in THF, 0.72 mL, 0.72 mmol) was added to a THF (5 mL) solution of Example 14-A (257 mg, 0.478 mmol) at rt. The mixture was then stirred at rt for 3 h, and then diluted with EtOAc and water. The organic layer was then washed with water and brine, dried over sodium sulfate, filtered and concentrated. The resulting residue was purified by silica gel flash column chromatography (0-100% EtOAc in heptane) to afford the title compound. (ESI+) m/z 424.4 (M+H).

Example 14-C. tert-Butyl 4-(4-((2-(6-(4-(ethoxycarbonyl)-5-(trifluoromethyl)-1H-pyrazol-1-yl)pyridin-2-yl)-6,6-dimethylcyclohex-1-en-1-yl)methoxy)-2-ethylphenyl)piperidine-1-carboxylate

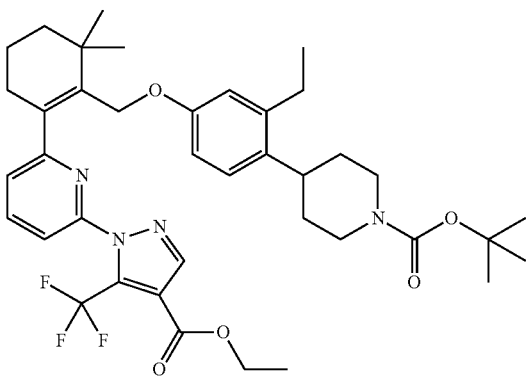 [SMILES: CCOC(=O)c1cnn(-c2cccc(C3=C(COc4ccc(C5CCN(C(=O)OC(C)(C)C)CC5)c(CC)c4)C(C)(C)CCC3)n2)c1C(F)(F)F]

To a solution Example 14-B (45 mg, 0.106 mmol), Intermediate 2-2 (48.7 mg, 0.159 mmol) and PPh$_3$ (41.8 mg, 0.159 mmol) in THF (3 mL) was added DIAD (0.04 mL, 0.206 mmol), and then the mixture was stirred at rt for 2 h. The reaction mixture was purified by silica gel flash column chromatography (0-100% EtOAc in heptane) to afford the title compound. (ESI+) m/z 711.5 (M+H).

Example 14-D. Ethyl 1-(6-(2-((3-ethyl-4-(piperidin-4-yl)phenoxy)methyl)-3,3-dimethylcyclohex-1-en-1-yl)pyridin-2-yl)-5-(trifluoromethyl)-1H-pyrazole-4-carboxylate

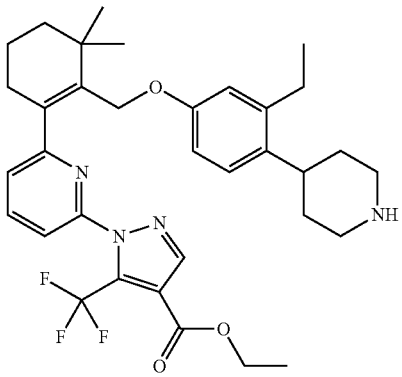 [SMILES: CCOC(=O)c1cnn(-c2cccc(C3=C(COc4ccc(C5CCNCC5)c(CC)c4)C(C)(C)CCC3)n2)c1C(F)(F)F]

A mixture of Example 14-C (62 mg, 0.087 mmol) and TFA (0.1 mL, 1.30 mmol) in DCM (3 mL) was stirred at rt for 2 h. The reaction mixture was then diluted with toluene, and then concentrated. The resulting residue was purified by silica gel flash column chromatography (0-20% MeOH/DCM) to afford the title compound. MS (ESI+) m/z 611.5 (M+H).

Example 14-E. Ethyl 1-(6-(2-((4-(1-(cyclopropanecarbonyl)piperidin-4-yl)-3-ethylphenoxy)methyl)-3,3-dimethylcyclohex-1-en-1-yl)pyridin-2-yl)-5-(trifluoromethyl)-1H-pyrazole-4-carboxylate

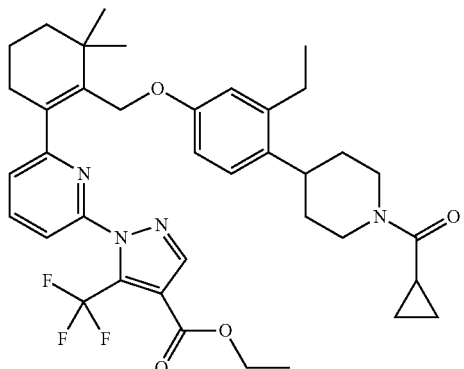

To a solution of Example 14-D (35 mg, 0.057 mmol) and DIPEA (0.03 mL, 0.17 mmol) in DCM (3 mL) was added cyclopropanecarbonyl chloride (0.01 mL, 0.110 mmol). The mixture was stirred at rt for 1 h. The reaction mixture purified by silica gel flash column chromatography (20% EtOAc in heptane) to afford the title compound. MS (ESI+) m/z 679.5 (M+H).

Example 14. 1-(6-(2-((4-(1-(Cyclopropanecarbonyl) piperidin-4-yl)-3-ethylphenoxy)methyl)-3,3-dimethylcyclohex-1-en-1-yl)pyridin-2-yl)-5-(trifluoromethyl)-1H-pyrazole-4-carboxylic acid

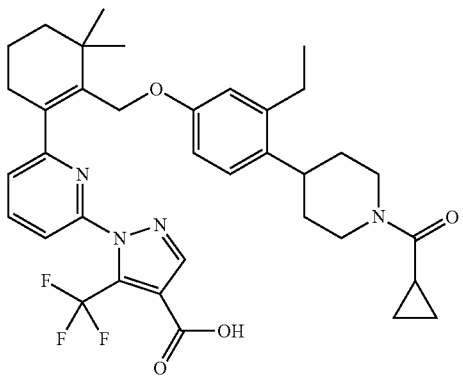 [SMILES: CCc1cc(OCC2=C(c3cccc(-n4ncc(C(=O)O)c4C(F)(F)F)n3)CCCC2(C)C)ccc1C1CCN(C(=O)C2CC2)CC1]

To a solution of Example 14-E (35 mg, 0.052 mmol) in THF (2 mL)/MeOH (1 mL)/water (1 mL) was added LiOH (14 mg, 0.619 mmol). The mixture was then stirred at rt for 20 h, and diluted with water, and then rendered acidic by 1M aq. HCl (pH=2). The mixture was then extracted with EtOAc. The organic phase was dried over sodium sulfate filtered and concentrated to afford the title compound. $^1$H NMR (400 MHz, CD$_3$OD) δ 8.11 (s, 1H), 7.87 (t, J=7.8 Hz, 1H), 7.56 (dd, J=7.7, 0.9 Hz, 1H), 7.51 (dd, J=8.0, 0.9 Hz, 1H), 6.98-7.07 (m, 1H), 6.59 (dt, J=4.4, 2.4 Hz, 2H), 4.65 (d, J=13.3 Hz, 1H), 4.46 (d, J=13.3 Hz, 1H), 4.30 (s, 2H), 3.01 (t, J=12.0 Hz, 1H), 2.74 (t, J=12.9 Hz, 1H), 2.65 (q, J=7.5 Hz, 2H), 2.48 (t, J=6.3 Hz, 2H), 2.27 (t, J=7.4 Hz, 1H), 1.95-2.07 (m, 1H), 1.49-1.93 (m, 9H), 1.21 (s, 6H), 1.17 (t, J=7.5 Hz, 3H), 0.73-0.99 (m, 4H). HRMS calcd. for C$_{36}$H$_{42}$F$_3$N$_4$O$_4$ (M+H) 651.3153, found 651.3165.

Example 15

Example 15-A(a). (±)-Ethyl 1-(6-(2-((4-(1-(cyclopropanecarbonyl)piperidin-4-yl)-2-methylphenoxy) methyl)-3-methylcyclohex-1-en-1-yl)pyridin-2-yl)-5-(trifluoromethyl)-1H-pyrazole-4-carboxylate

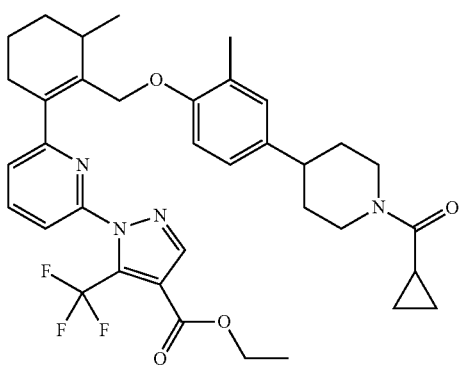 [SMILES: CCOC(=O)c1cnn(-c2cccc(C3=C(COc4ccc(C5CCN(C(=O)C6CC6)CC5)cc4C)C(C)CCC3)n2)c1C(F)(F)F]

To a solution of Intermediate 2-4 (152 mg, 0.586 mmol), PPh$_3$ (192 mg, 0.733 mmol) and Example 13-B (240 mg, 0.586 mmol) in THF (6 mL) at rt was added DIAD (0.15 mL, 0.733 mmol). The mixture was then stirred at room temperature for 1 h, and then diluted with water. The mixture was then extracted with EtOAc. The organic layer was then dried over magnesium sulfate, filtered and concentrated. The resulting residue was purified by silica gel flash column chromatography (0-100% EtOAc in heptane), followed by RP-HPLC (HC-B) to afford the title compound. MS (ESI+) m/z 651.4 (M+H).

Example 15-A(b). (+) or (−)-Ethyl 1-(6-(2-((4-(1-(cyclopropanecarbonyl)piperidin-4-yl)-2-methylphenoxy)methyl)-3-methylcyclohex-1-en-1-yl)pyridin-2-yl)-5-(trifluoromethyl)-1H-pyrazole-4-carboxylate (enantiomer-1, tr=2.6 min) and (−) or (+)-ethyl 1-(6-(2-((4-(1-(cyclopropanecarbonyl)piperidin-4-yl)-2-methylphenoxy)methyl)-3-methylcyclohex-1-en-1-yl)pyridin-2-yl)-5-(trifluoromethyl)-1H-pyrazole-4-carboxylate (enantiomer-2, tr=2.8 min)

Resolution of the enantiomers of (±)-ethyl 1-(6-(2-((4-(1-(cyclopropanecarbonyl)piperidin-4-yl)-2-methylphenoxy)methyl)-3-methylcyclohex-1-en-1-yl)pyridin-2-yl)-5-(trifluoromethyl)-1H-pyrazole-4-carboxylate was achieved by chiral SFC using a CHIRALPAK® AD-H column with 30% (10 mM NH$_4$OH in 2-propanol) in CO$_2$ to afford (+) or (−)-ethyl 1-(6-(2-((4-(1-(cyclopropanecarbonyl)piperidin-4-yl)-2-methylphenoxy)methyl)-3-methylcyclohex-1-en-1-yl)pyridin-2-yl)-5-(trifluoromethyl)-1H-pyrazole-4-carboxylate (enantiomer-1, tr=2.6 min) and (−) or (+)-ethyl 1-(6-(2-((4-(1-(cyclopropanecarbonyl)piperidin-4-yl)-2-methylphenoxy)methyl)-3-methylcyclohex-1-en-1-yl)pyridin-2-yl)-5-(trifluoromethyl)-1H-pyrazole-4-carboxylate (enantiomer-2, tr=2.8 min).

Example 15a. (+)-1-(6-(2-((4-(1-(cyclopropanecarbonyl)piperidin-4-yl)-2-methylphenoxy)methyl)-3-methylcyclohex-1-en-1-yl)pyridin-2-yl)-5-(trifluoromethyl)-1H-pyrazole-4-carboxylic acid

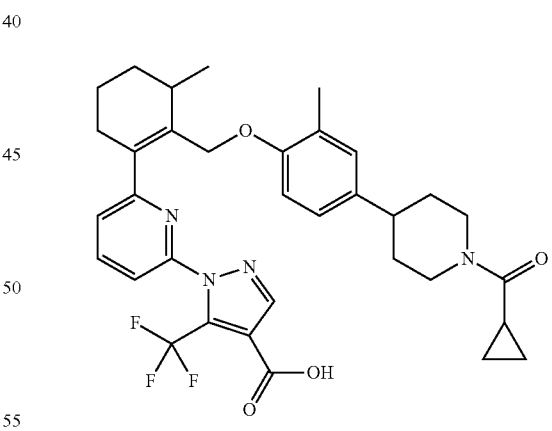

To a solution of (+) or (−)-ethyl 1-(6-(2-((4-(1-(cyclopropanecarbonyl)piperidin-4-yl)-2-methylphenoxy)methyl)-3-methylcyclohex-1-en-1-yl)pyridin-2-yl)-5-(trifluoromethyl)-1H-pyrazole-4-carboxylate (Example 15-A(b), enantiomer-1, tr=2.6 min) (70 mg, 0.108 mmol) in THF (2 mL)/MeOH (1 mL)/water (1 mL) was added LiOH (20 mg, 0.835 mmol). The mixture was then stirred at rt for 20 h. The reaction mixture was diluted with water, and then rendered acidic by the addition of 1M aq. HCl (ca. pH=2). The mixture was extracted with EtOAc. The organic layer was dried over MgSO$_4$, filtered and concentrated. The residue was purified by RP-HPLC (HC-A) to afford the title compound. ¹H NMR (400 MHz, CD₃OD) δ 8.06 (s, 1H), 7.95 (t, J=7.8 Hz, 1H), 7.56 (dd, J=8.0, 0.9 Hz, 1H), 7.45 (dd, J=7.7, 0.9 Hz, 1H), 7.05-6.96 (m, 1H), 6.63-6.52 (m, 2H), 4.64 (d, J=13.1 Hz, 1H), 4.56-4.30 (m, 3H), 2.99 (tt, J=12.4, 3.4 Hz, 1H), 2.81-2.67 (m, 1H), 2.66-2.50 (m, 4H), 2.45-2.31 (m, 1H), 2.06-1.94 (m, 1H), 1.91-1.44 (m, 9H), 1.21 (d, J=7.0 Hz, 3H), 1.14 (t, J=7.5 Hz, 3H), 0.97-0.73 (m, 4H).

HRMS calcd. for $C_{34}H_{38}F_3N_4O_4$ (M+H) 623.2840, found 623.2870.

Example 15b. (−)-1-(6-(2-((4-(1-(Cyclopropanecarbonyl)piperidin-4-yl)-2-methylphenoxy)methyl)-3-methylcyclohex-1-en-1-yl)pyridin-2-yl)-5-(trifluoromethyl)-1H-pyrazole-4-carboxylic acid

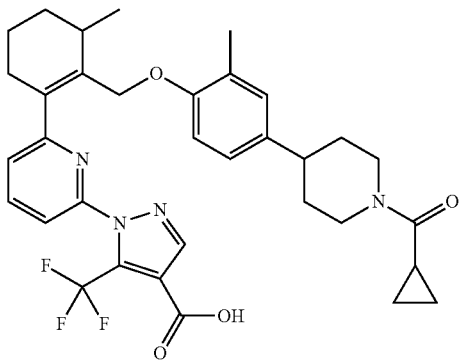 [SMILES: Cc1cc(C2CCN(C(=O)C3CC3)CC2)ccc1OCC1=C(c2cccc(-n3ncc(C(=O)O)c3C(F)(F)F)n2)CCCC1C]

The title compound was synthesized from (−) or (+)-ethyl 1-(6-(2-((4-(1-(cyclopropanecarbonyl)piperidin-4-yl)-2-methylphenoxy)methyl)-3-methylcyclohex-1-en-1-yl)pyridin-2-yl)-5-(trifluoromethyl)-1H-pyrazole-4-carboxylate (Example 15-A(b), enantiomer-2, tr=2.8 min) analogously to the preparation of Example 15a. ¹H NMR (400 MHz, CD₃OD) δ 8.06 (s, 1H), 7.95 (t, J=7.8 Hz, 1H), 7.56 (dd, J=8.0, 0.9 Hz, 1H), 7.45 (dd, J=7.7, 0.9 Hz, 1H), 7.05-6.96 (m, 1H), 6.63-6.52 (m, 2H), 4.64 (d, J=13.1 Hz, 1H), 4.56-4.30 (m, 3H), 2.99 (tt, J=12.4, 3.4 Hz, 1H), 2.81-2.67 (m, 1H), 2.66-2.50 (m, 4H), 2.45-2.31 (m, 1H), 2.06-1.94 (m, 1H), 1.91-1.44 (m, 9H), 1.21 (d, J=7.0 Hz, 3H), 1.14 (t, J=7.5 Hz, 3H), 0.97-0.73 (m, 4H). HRMS calcd. for $C_{34}H_{38}F_3N_4O_4$ (M+H) 623.2840, found 623.2870.

Example 16

Example 16-A. (±)-tert-Butyl 4-(2-ethyl-4-((6-methyl-2-(4,4,5,5-tetramethyl-1,3,2-dioxaborolan-2-yl)cyclohex-1-en-1-yl)methoxy)phenyl)piperidine-1-carboxylate

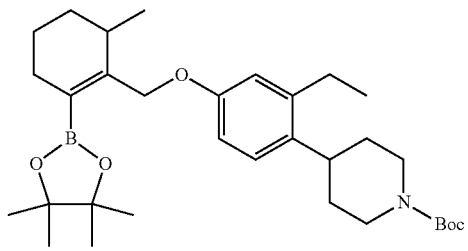 [SMILES: CCc1cc(OCC2=C(B3OC(C)(C)C(C)(C)O3)CCCC2C)ccc1C1CCN(C(=O)OC(C)(C)C)CC1]

To a suspension of (±)-tert-butyl 4-(2-ethyl-4-((6-methyl-2-(((trifluoromethyl)-sulfonyl)oxy)cyclohex-1-en-1-yl)methoxy)phenyl)piperidine-1-carboxylate (Intermediate 10) (1.22 g, 2.17 mmol), bis(pinacolato)diboron (0.827 g, 3.26 mmol), KOAc (0.384 g, 3.91 mmol) in dioxane (21.7 mL) was added PdCl₂(dppf).CH₂Cl₂ adduct (0.06 g, 0.07 mmol). The mixture was then stirred at 60° C. for 2 h, and then at 80° C. for 1.5 h. The reaction mixture was cooled to room temperature, and then diluted with EtOAc. The mixture was washed with water, dried over Na₂SO₄, filtered, and then concentrated. The resulting residue was purified by silica gel flash column chromatography (0-40% EtOAc/heptane) to afford the title compound. MS (ESI+) m/z 484.5 (M-tBu+2H)⁺

Example 16-B. (±)-tert-Butyl 4-(4-((2-(6-(4-(ethoxycarbonyl)-5-methyl-1H-pyrazol-1-yl)pyridin-2-yl)-6-methylcyclohex-1-en-1-yl)methoxy)-2-ethylphenyl)piperidine-1-carboxylate

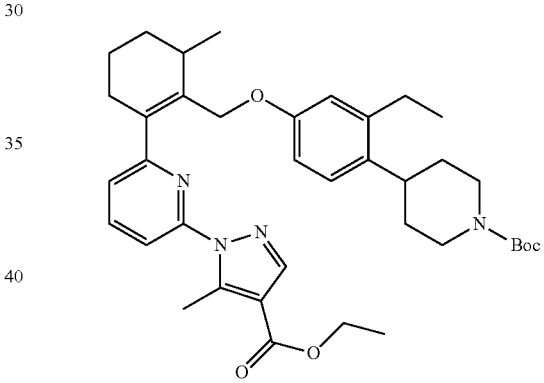

A suspension of (±)-tert-butyl 4-(2-ethyl-4-((6-methyl-2-(4,4,5,5-tetramethyl-1,3,2-dioxaborolan-2-yl)cyclohex-1-en-1-yl)methoxy)phenyl)piperidine-1-carboxylate (1.56 g, 2.89 mmol), ethyl 1-(6-bromopyridin-2-yl)-5-methyl-1H-pyrazole-4-carboxylate (Intermediate 1-5) (1.26 g, 4.05 mmol), 2 M aq. K₃PO₄ (4.34 mL, 8.68 mmol), and chloro(2-dicyclohexylphosphino-2',6'-dimethoxy-1,1'-biphenyl)[2-(2-aminoethylphenyl)]palladium(II) methyl-t-butylether adduct (CAS#1028206-58-7, 0.097 g, 0.145 mmol) in DMF (10 mL) was stirred at 110° C. for 3 h. The reaction mixture was cooled to room temperature, and then diluted with EtOAc. The mixture was then washed with water, dried over Na₂SO₄, filtered, and then concentrated. The resulting residue was purified by silica gel flash column chromatography (0-30% EtOAc/heptane) to afford the title compound. MS (ESI+) m/z 643.6 (M+H)⁺

Example 16-C. (±)-Ethyl 1-(6-(2-((3-ethyl-4-(piperidin-4-yl)phenoxy)methyl)-3-methylcyclohex-1-en-1-yl)pyridin-2-yl)-5-methyl-1H-pyrazole-4-carboxylate

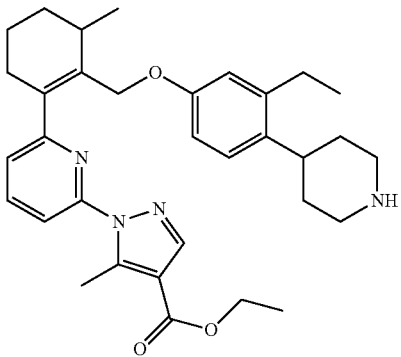 [SMILES: CCOC(=O)c1cnn(-c2cccc(C3=C(COc4ccc(C5CCNCC5)c(CC)c4)C(C)CCC3)n2)c1C]

A solution of (±)-tert-butyl 4-(4-((2-(6-(4-(ethoxycarbonyl)-5-methyl-1H-pyrazol-1-yl)pyridin-2-yl)-6-methylcyclohex-1-en-1-yl)methoxy)-2-ethylphenyl)piperidine-1-carboxylate (225 mg, 0.350 mmol) and TFA (1.1 mL) in DCM (5 mL) was stirred at 0° C. for 3 h. The reaction was quenched with satd. aq. NaHCO₃. The mixture was then extracted three times with EtOAc. The combined organic layers were washed with brine, dried over Na₂SO₄, filtered, and then concentrated to furnish the title compound. MS (ESI+) m/z 543.5 (M+H)⁺

Example 16-D(a). (±)-Ethyl 1-(6-(2-((4-(1-(cyclopropanecarbonyl)piperidin-4-yl)-3-ethylphenoxy)methyl)-3-methylcyclohex-1-en-1-yl)pyridin-2-yl)-5-methyl-1H-pyrazole-4-carboxylate

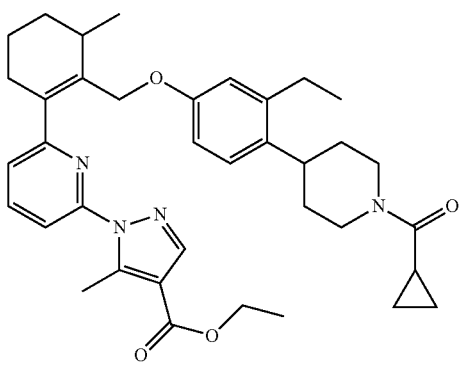 [SMILES: CCOC(=O)c1cnn(-c2cccc(C3=C(COc4ccc(C5CCN(C(=O)C6CC6)CC5)c(CC)c4)C(C)CCC3)n2)c1C]

To a solution of (±)-ethyl 1-(6-(2-((3-ethyl-4-(piperidin-4-yl)phenoxy)methyl)-3-methylcyclohex-1-en-1-yl)pyridin-2-yl)-5-methyl-1H-pyrazole-4-carboxylate (0.2 g, 0.37 mmol) in DCM (4 mL) was added DIPEA (0.26 mL), followed by cyclopropanecarbonyl chloride (0.067 mL, 0.737 mmol). The mixture was stirred at room temperature for 72 h, and then diluted with water. The mixture was extracted twice with DCM. Combined organic extracts were washed with brine, dried over Na₂SO₄, filtered, and then concentrated. The resulting residue was purified by silica gel flash column chromatography (0-70% EtOAc/heptane) to afford the title compound. MS (ESI+) m/z 611.5 (M+H)⁺.

Example 16-D(b). (+) or (−)-Ethyl 1-(6-(2-((4-(1-(cyclopropanecarbonyl)piperidin-4-yl)-3-ethylphenoxy)methyl)-3-methylcyclohex-1-en-1-yl)pyridin-2-yl)-5-methyl-1H-pyrazole-4-carboxylate (enantiomer-1, t$_r$=5.9 min) and (−) or (+)-ethyl 1-(6-(2-((4-(1-(cyclopropanecarbonyl)piperidin-4-yl)-3-ethylphenoxy)methyl)-3-methylcyclohex-1-en-1-yl)pyridin-2-yl)-5-methyl-1H-pyrazole-4-carboxylate (enantiomer-2, t$_r$=7.5 min)

Resolution of the enantiomers of (±)-ethyl 1-(6-(2-((4-(1-(cyclopropanecarbonyl)piperidin-4-yl)-3-ethylphenoxy)methyl)-3-methylcyclohex-1-en-1-yl)pyridin-2-yl)-5-methyl-1H-pyrazole-4-carboxylate was achieved by chiral SFC using a CHIRALPAK® AD-H column with 25% iPrOH in CO₂ to afford (+) or (−)-ethyl 1-(6-(2-((4-(1-(cyclopropanecarbonyl)piperidin-4-yl)-3-ethylphenoxy)methyl)-3-methylcyclohex-1-en-1-yl)pyridin-2-yl)-5-methyl-1H-pyrazole-4-carboxylate (enantiomer-1, t$_r$=5.9 min) and (−) or (+)-ethyl 1-(6-(2-((4-(1-(cyclopropanecarbonyl)piperidin-4-yl-3-ethylphenoxy)methyl)-3-methylcyclohex-1-en-1-yl)pyridin-2-yl)-5-methyl-1H-pyrazole-4-carboxylate (enantiomer-2, t$_r$=7.5 min).

Example 16a. (+)-1-(6-(2-((4-(1-(Cyclopropanecarbonyl)piperidin-4-yl)-3-ethylphenoxy)methyl)-3-methylcyclohex-1-en-1-yl)pyridin-2-yl)-5-methyl-1H-pyrazole-4-carboxylic acid

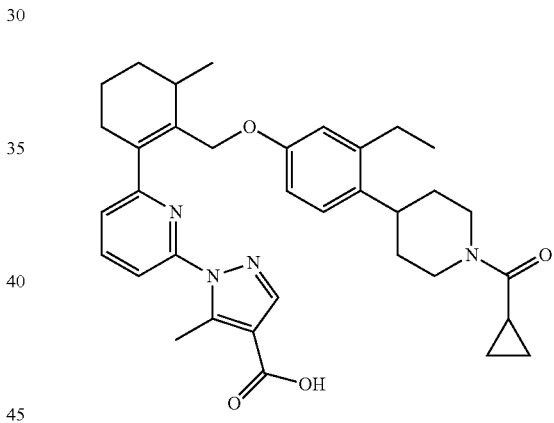

To a solution of (+) or (−)-ethyl 1-(6-(2-((4-(1-(cyclopropanecarbonyl)piperidin-4-yl)-3-ethylphenoxy)methyl)-3-methylcyclohex-1-en-1-yl)pyridin-2-yl)-5-methyl-1H-pyrazole-4-carboxylate (enantiomer-1, tr=5.9 min) (160 mg, 0.262 mmol) in MeOH/THF (0.2 mL/3 mL) was added 1M aq. NaOH (2.6 mL, 2.6 mmol). The mixture was stirred at room temperature for 20 h, and then stirred at 50° C. for 1 h. The mixture was diluted with EtOAc. The mixture was then rendered acidic by treatment with 1N aq. HCl, and was then extracted with three times with EtOAc. Combined organic extracts were then washed with brine, dried over Na₂SO₄, filtered, and then concentrated. The resulting residue was purified by silica gel flash column chromatography (0-10% MeOH/DCM) to afford the title compound. ¹H NMR (400 MHz, CD₃OD) δ 7.99 (s, 1H) 7.90 (dd, J=8.0, 7.8 Hz, 1H) 7.63 (dd, J=8.1, 0.8 Hz, 1H) 7.34 (dd, J=7.6, 0.8 Hz, 1H) 7.00 (d, J=8.1 Hz, 1H) 6.53-6.60 (m, 2H) 4.58-4.69 (m, 1H) 4.48-4.54 (m, 1H) 4.38-4.48 (m, 2H) 3.19-3.27 (m, 1H) 2.93-3.03 (m, 1H) 2.78 (s, 3H) 2.66-2.77 (m, 1H) 2.52-2.64 (m, 4H) 2.35-2.47 (m, 1H) 1.94-2.04 (m, 1H) 1.82-1.93 (m, 2H) 1.46-1.82 (m, 6H) 1.22 (d, J=7.0 Hz, 3H) 1.12 (t, J=7.6

Hz, 3H) 0.76-0.94 (m, 4H). HRMS; calcd. for $C_{35}H_{43}N_4O_4$ (M+H) 583.3279, found 583.3253.

Example 16b. (−)-1-(6-(2-((4-(1-(Cyclopropanecarbonyl)piperidin-4-yl)-3-ethylphenoxy)methyl)-3-methylcyclohex-1-en-1-yl)pyridin-2-yl)-5-methyl-1H-pyrazole-4-carboxylic acid (−) or (+)-Ethyl 1-(6-(2-((4-(1-(cyclopropanecarbonyl)piperidin-4-yl)-3-ethylphenoxy)methyl)-3-methylcyclohex-1-en-1-yl)pyridin-2-yl)-5-methyl-1H-pyrazole-4-carboxylate (enantiomer-2, $t_r$=7.5 min) was saponified as described in Example 16a to afford the title compound. $^1$H NMR and HRMS data were substantially identical to Example 16a.

Example 17

Example 17-A. (±)-tert-Butyl 4-(4-((2-(6-(4-(ethoxycarbonyl)-5-ethyl-1H-pyrazol-1-yl)pyridin-2-yl)-6-methylcyclohex-1-en-1-yl)methoxy)-2-ethylphenyl)piperidine-1-carboxylate

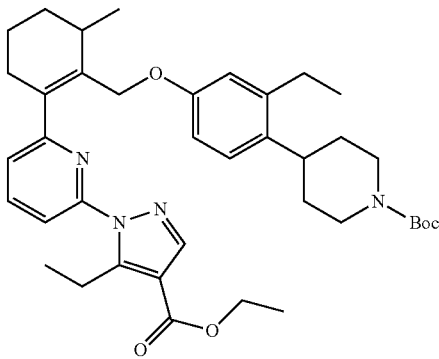 [SMILES: CCOC(=O)c1cnn(-c2cccc(C3=C(COc4ccc(C5CCN(C(=O)OC(C)(C)C)CC5)c(CC)c4)C(C)CCC3)n2)c1CC]

A suspension of ethyl 1-(6-bromopyridin-2-yl)-5-ethyl-1H-pyrazole-4-carboxylate (Intermediate 1-3) (0.56 g, 1.73 mmol), bis(pinacolato)diboron (0.48 g, 1.90 mmol), KOAc (0.34 g, 3.45 mmol) and chloro(2-dicyclohexylphosphino-2',6'-dimethoxy-1,1'-biphenyl)[2-(2-aminoethylphenyl)]palladium(II) methyl-t-butylether adduct (0.058 g, 0.086 mmol) in dioxane (5 mL) was stirred at 110° C. for 2 h. To the mixture at 50° C. were then added a solution of (±)-tert-butyl 4-(2-ethyl-4-((6-methyl-2-(((trifluoromethyl)-sulfonyl)oxy)cyclohex-1-en-1-yl)methoxy)phenyl)piperidine-1-carboxylate (Intermediate 10) (0.92 g, 1.64 mmol) in DMF (5 mL), $Cs_2CO_3$ (1.7 g, 5.2 mmol), and chloro(2-dicyclohexylphosphino-2',6'-dimethoxy-1,1'-biphenyl)[2-(2-aminoethylphenyl)]palladium(II) methyl-t-butylether adduct (0.058 g, 0.086 mmol). The mixture was then stirred at 50° C. for 15 h, and then at 110° C. for 5 h. The reaction mixture was cooled to room temperature, and then diluted with water. The mixture was then extracted twice with EtOAc. Combined organic extracts were successively washed three times with water and brine, dried over $Na_2SO_4$, filtered, and then concentrated. The resulting residue was purified by silica gel flash column chromatography (0-40% EtOAc/heptane) to afford the title compound. MS (ESI+) m/z 657.7 (M+H)$^+$

Example 17-B. (±)-Ethyl 5-ethyl-1-(6-(2-((3-ethyl-4-(piperidin-4-yl)phenoxy)methyl)-3-methylcyclohex-1-en-1-yl)pyridin-2-yl)-1H-pyrazole-4-carboxylate

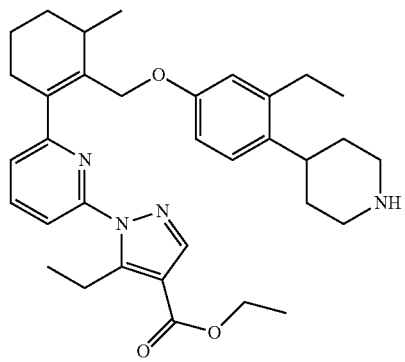 [SMILES: CCOC(=O)c1cnn(-c2cccc(C3=C(COc4ccc(C5CCNCC5)c(CC)c4)C(C)CCC3)n2)c1CC]

The title compound was synthesized starting from (±)-tert-butyl 4-(4-((2-(6-(4-(ethoxycarbonyl)-5-ethyl-1H-pyrazol-1-yl)pyridin-2-yl)-6-methylcyclohex-1-en-1-yl)methoxy)-2-ethylphenyl)piperidine-1-carboxylate analogously to the procedure as described in Example 16-C. MS (ESI+) m/z 557.5 (M+H)$^+$

Example 17-C(a). (±)-Ethyl 1-(6-(2-((4-(1-(cyclopropanecarbonyl)piperidin-4-yl)-3-ethylphenoxy)methyl)-3-methylcyclohex-1-en-1-yl)pyridin-2-yl)-5-ethyl-1H-pyrazole-4-carboxylate

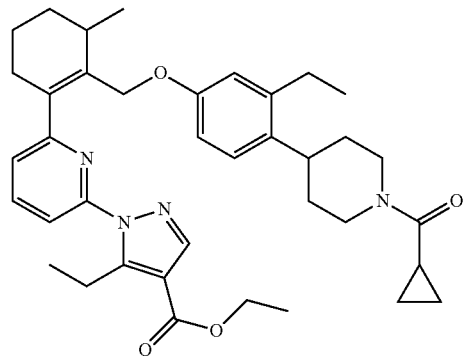 [SMILES: CCOC(=O)c1cnn(-c2cccc(C3=C(COc4ccc(C5CCN(C(=O)C6CC6)CC5)c(CC)c4)C(C)CCC3)n2)c1CC]

The title compound was synthesized by reacting (±)-ethyl 5-ethyl-1-(6-(2-((3-ethyl-4-(piperidin-4-yl)phenoxy)methyl)-3-methylcyclohex-1-en-1-yl)pyridin-2-yl)-1H-pyrazole-4-carboxylate with cyclopropanecarbonyl chloride analogously to the procedure described in Example 16-D(a). MS (ESI+) m/z 625.6 (M+H)$^+$.

Example 17-C(b). (+) or (−)-Ethyl 1-(6-(2-((4-(1-(cyclopropanecarbonyl)piperidin-4-yl)-3-ethylphenoxy)methyl)-3-methylcyclohex-1-en-1-yl)pyridin-2-yl)-5-ethyl-1H-pyrazole-4-carboxylate (enantiomer-1, $t_r$=6.5 min) and (−) or (+)-ethyl 1-(6-(2-((4-(1-(cyclopropanecarbonyl)piperidin-4-yl)-3-ethylphenoxy)methyl)-3-methylcyclohex-1-en-1-yl)pyridin-2-yl)-5-ethyl-1H-pyrazole-4-carboxylate (enantiomer-2, $t_r$=7.8 min)

Resolution of the enantiomers of (±)-ethyl 1-(6-(2-((4-(1-(cyclopropanecarbonyl)piperidin-4-yl)-3-ethylphenoxy)

methyl)-3-methylcyclohex-1-en-1-yl)pyridin-2-yl)-5-ethyl-1H-pyrazole-4-carboxylate was achieved by chiral SFC using a CHIRALPAK® IA column with 25% iPrOH in $CO_2$ to afford (+) or (−)-ethyl 1-(6-(2-((4-(1-(cyclopropanecarbonyl)piperidin-4-yl)-3-ethylphenoxy)methyl)-3-methylcyclohex-1-en-1-yl)pyridin-2-yl)-5-ethyl-1H-pyrazole-4-carboxylate (enantiomer-1, $t_r$=6.5 min) and (−) or (+)-ethyl 1-(6-(2-((4-(1-(cyclopropanecarbonyl)piperidin-4-yl)-3-ethylphenoxy)methyl)-3-methylcyclohex-1-en-1-yl)pyridin-2-yl)-5-ethyl-1H-pyrazole-4-carboxylate (enantiomer-2, $t_r$=7.8 min).

Example 17a. (+)-1-(6-(2-((4-(1-(Cyclopropanecarbonyl)piperidin-4-yl)-3-ethylphenoxy)methyl)-3-methylcyclohex-1-en-1-yl)pyridin-2-yl)-5-ethyl-1H-pyrazole-4-carboxylic acid

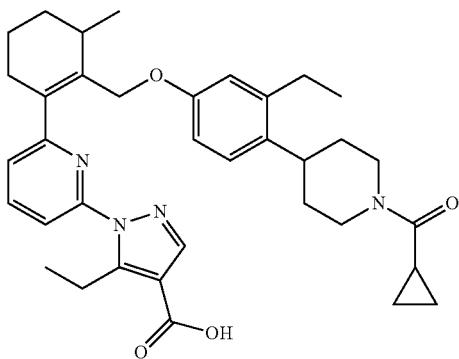 [SMILES: CCc1cc(OCC2=C(c3cccc(-n4ncc(C(=O)O)c4CC)n3)CCCC2C)ccc1C1CCN(C(=O)C2CC2)CC1]

The title compound was synthesized by a saponification of (+) or (−)-ethyl 1-(6-(2-((4-(1-(cyclopropanecarbonyl)piperidin-4-yl)-3-ethylphenoxy)methyl)-3-methylcyclohex-1-en-1-yl)pyridin-2-yl)-5-ethyl-1H-pyrazole-4-carboxylate (enantiomer-1, $t_r$=6.5 min) by an analogous method as described in Example 16a. $^1$H NMR (400 MHz, $CD_3OD$ δ 8.00 (s, 1H) 7.91 (t, J=7.8 Hz, 1H) 7.64 (d, J=7.5 Hz, 1H) 7.36 (d, J=7.6 Hz, 1H) 6.95-7.02 (m, 1H) 6.52-6.60 (m, 2H) 4.59-4.68 (m, 1H) 4.36-4.58 (m, 4H) 3.19-3.28 (m, 2H) 2.93-3.03 (m, 1H) 2.67-2.79 (m, 1H) 2.51-2.66 (m, 4H) 2.34-2.45 (m, 1H) 1.95-2.04 (m, 1H) 1.82-1.94 (m, 2H) 1.45-1.82 (m, 6H) 1.16-1.26 (m, 6H) 1.12 (t, J=7.5 Hz, 3H) 0.74-0.95 (m, 4H). HRMS; calcd. for $C_{36}H_{45}N_4O_4$ (M+H) 597.3435, found 597.3398.

Example 17b. (−)-1-(6-(2-((4-(1-(Cyclopropanecarbonyl)piperidin-4-yl)-3-ethylphenoxy)methyl)-3-methylcyclohex-1-en-1-yl)pyridin-2-yl)-5-ethyl-1H-pyrazole-4-carboxylic acid (−) or (+)-Ethyl 1-(6-(2-((4-(1-(cyclopropanecarbonyl)piperidin-4-yl)-3-ethylphenoxy)methyl)-3-methylcyclohex-1-en-1-yl)pyridin-2-yl)-5-ethyl-1H-pyrazole-4-carboxylate (enantiomer-2, $t_r$=7.8 min) was saponified by an analogous method as described in Example 16a to afford the title compound. $^1$H NMR and HRMS data were substantially identical to Example 17a.

Example 18

Example 18-A(a). Ethyl 5-ethyl-1-(6-(2-((3-ethyl-4-(1-((S)-2-hydroxypropanoyl)piperidin-4-yl)phenoxy)methyl)-3-methylcyclohex-1-en-1-yl)pyridin-2-yl)-1H-pyrazole-4-carboxylate

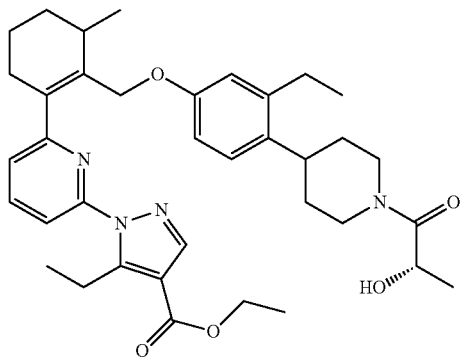 [SMILES: CCOC(=O)c1cnn(-c2cccc(C3=C(COc4ccc(C5CCN(C(=O)[C@H](C)O)CC5)c(CC)c4)C(C)CCC3)n2)c1CC]

HATU (0.27 g, 0.72 mmol) was added to a DMF (2.9 mL) solution of (±)-ethyl 5-ethyl-1-(6-(2-((3-ethyl-4-(piperidin-4-yl)phenoxy)methyl)-3-methylcyclohex-1-en-1-yl)pyridin-2-yl)-1H-pyrazole-4-carboxylate (Example 17-B) (0.32 g, 0.58 mmol), L-(+)-lactic acid (0.065 g, 0.72 mmol) and DIPEA (0.30 mL, 1.724 mmol) at 0° C. The mixture was then stirred at room temperature for 0.5 h, and then diluted with water. The mixture was then extracted twice with EtOAc. The combined organic extracts were washed with brine, dried over $Na_2SO_4$, filtered, and then concentrated. The resulting residue was purified by silica gel flash column chromatography (0-60% EtOAc/heptane) to afford the title compound. MS (ESI+) m/z 629.5 (M+H).

Example 18-A(b). Ethyl 5-ethyl-1-(6-(2-((3-ethyl-4-(1-((S)-2-hydroxypropanoyl)piperidin-4-yl)phenoxy)methyl)-3-methylcyclohex-1-en-1-yl)pyridin-2-yl)-1H-pyrazole-4-carboxylate (diastereomer-1) and ethyl 5-ethyl-1-(6-(2-((3-ethyl-4-(1-((S)-2-hydroxypropanoyl)piperidin-4-yl)phenoxy)methyl)-3-methylcyclohex-1-en-1-yl)pyridin-2-yl)-1H-pyrazole-4-carboxylate (diastereomer-2)

Resolution of the diastereomers of ethyl 1-(6-(2-((4-(1-(cyclopropanecarbonyl)piperidin-4-yl)-3-ethylphenoxy)methyl)-3-methylcyclohex-1-en-1-yl)pyridin-2-yl)-5-ethyl-1H-pyrazole-4-carboxylate was achieved by chiral SFC using a CHIRALPAK® AD-H column with 25% MeOH in $CO_2$ to afford ethyl 5-ethyl-1-(6-(2-((3-ethyl-4-(1-((S)-2-hydroxypropanoyl)piperidin-4-yl)phenoxy)methyl)-3-methylcyclohex-1-en-1-yl)pyridin-2-yl)-1H-pyrazole-4-carboxylate (diastereomer-1, $t_r$=10.1 min) and ethyl 5-ethyl-1-(6-(2-((3-ethyl-4-(1-((S)-2-hydroxypropanoyl)piperidin-4-yl)phenoxy)methyl)-3-methylcyclohex-1-en-1-yl)pyridin-2-yl)-1H-pyrazole-4-carboxylate (diastereomer-2, $t_r$=13.4 min).

Example 18a. 5-Ethyl-1-(6-(2-((3-ethyl-4-(1-((S)-2-hydroxypropanoyl)piperidin-4-yl)phenoxy)methyl)-3-methylcyclohex-1-en-1-yl)pyridin-2-yl)-1H-pyrazole-4-carboxylic acid (diastereomer-1)

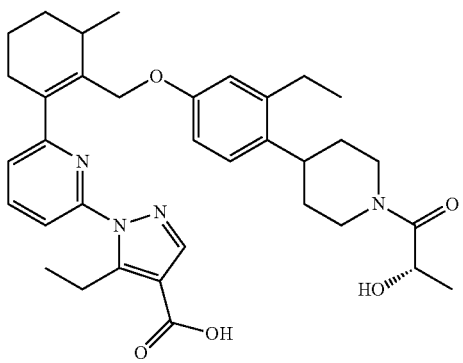 [SMILES: CCc1cc(OCC2=C(c3cccc(-n4ncc(C(=O)O)c4CC)n3)CCCC2C)ccc1C1CCN(C(=O)[C@H](C)O)CC1]

The title compound was synthesized by a saponification of ethyl 5-ethyl-1-(6-(2-((3-ethyl-4-(1-((S)-2-hydroxypropanoyl)piperidin-4-yl)phenoxy)methyl)-3-methylcyclohex-1-en-1-yl)pyridin-2-yl)-1H-pyrazole-4-carboxylate (diastereomer-1, $t_r$=10.1 min) by the method described in Example 16a. $^1$H NMR (400 MHz, DMSO-$d_6$) δ 7.87-8.07 (m, 2H) 7.68 (d, J=7.70 Hz, 1H) 7.36 (d, J=7.58 Hz, 1H) 7.00 (d, J=8.59 Hz, 1H) 6.34-6.74 (m, 2H) 4.79 (br. s., 1H) 4.40-4.56 (m, 3H) 4.36 (d, J=11.37 Hz, 1H) 4.05 (d, J=12.00 Hz, 1H) 3.22-3.30 (m, 2H) 3.08 (t, J=12.57 Hz, 1H) 2.81-2.94 (m, 1H) 2.60-2.72 (m, 1H) 2.54 (d, J=7.45 Hz, 3H) 2.28-2.42 (m, 1H) 1.73-1.89 (m, 2H) 1.57-1.71 (m, 3H) 1.31-1.56 (m, 3H) 1.11-1.26 (m, 9H) 1.07 (t, J=7.52 Hz, 3H). HRMS; calcd. for $C_{36}H_{46}N_4O_6$ (M+H) 601.3390, found 601.3384.

Example 18b. 5-Ethyl-1-(6-(2-((3-ethyl-4-(1-((S)-2-hydroxypropanoyl)piperidin-4-yl)phenoxy)methyl)-3-methylcyclohex-1-en-1-yl)pyridin-2-yl)-1H-pyrazole-4-carboxylic acid (diastereomer-2)

Ethyl 5-ethyl-1-(6-(2-((3-ethyl-4-(1-((S)-2-hydroxypropanoyl)piperidin-4-yl)phenoxy)methyl)-3-methylcyclohex-1-en-1-yl)pyridin-2-yl)-1H-pyrazole-4-carboxylate (diastereomer-2, $t_r$=13.4 min). was saponified as described in Example 16a to afford the title compound. $^1$H-NMR (400 MHz, DMSO-$d_6$) δ 12.48 (br. s., 1H), 7.95-8.03 (m, 2H), 7.67 (d, J=7.50 Hz, 1H), 7.33-7.39 (m, 1H), 6.96-7.03 (m, 1H), 6.56-6.63 (m, 2H), 4.78 (d, J=6.44 Hz, 1H), 4.40-4.54 (m, 3H), 4.35 (d, J=11.37 Hz, 1H), 3.99-4.12 (m, 1H), 3.22-3.30 (m, 3H), 3.02-3.15 (m, 1H), 2.83-2.94 (m, 1H), 2.60-2.72 (m, 1H), 2.52-2.60 (m, 3H), 2.30-2.41 (m, 1H), 1.73-1.86 (m, 2H), 1.30-1.72 (m, 6H), 1.11-1.24 (m, 9H), 1.06 (t, J=7.52 Hz, 3H). HRMS; calcd. for $C_{36}H_{46}N_4O_6$ (M+H) 601.3390, found 601.3391.

Example 19

Example 19-A(a). Ethyl 1-(6-(2-((3-ethyl-4-(1-((S)-2-hydroxypropanoyl)piperidin-4-yl)phenoxy)methyl)-3-methylcyclohex-1-en-1-yl)pyridin-2-yl)-5-methyl-1H-pyrazole-4-carboxylate

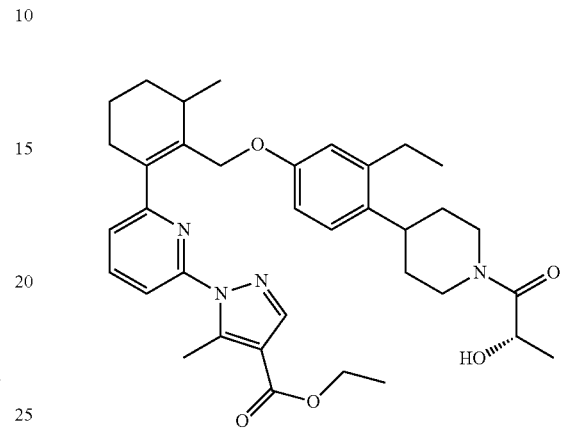

The title compound was synthesized from (±)-ethyl 1-(6-(2-((3-ethyl-4-(piperidin-4-yl)phenoxy)methyl)-3-methylcyclohex-1-en-1-yl)pyridin-2-yl)-5-methyl-1H-pyrazole-4-carboxylate, Example 16-C, by the method described for Example 18-A(a). MS (ESI+) m/z 615.6 (M+H).

Example 18-A(b) Ethyl 1-(6-(2-((3-ethyl-4-(1-((S)-2-hydroxypropanoyl)piperidin-4-yl)phenoxy)methyl)-3-methylcyclohex-1-en-1-yl)pyridin-2-yl)-5-methyl-1H-pyrazole-4-carboxylate (diastereomer-1) and ethyl 1-(6-(2-((3-ethyl-4-(1-((S)-2-hydroxypropanoyl)piperidin-4-yl)phenoxy)methyl)-3-methylcyclohex-1-en-1-yl)pyridin-2-yl)-5-methyl-1H-pyrazole-4-carboxylate (diastereomer-2)

Resolution of the diastereomers of ethyl 1-(6-(2-((3-ethyl-4-(1-((S)-2-hydroxypropanoyl)piperidin-4-yl)phenoxy)methyl)-3-methylcyclohex-1-en-1-yl)pyridin-2-yl)-5-methyl-1H-pyrazole-4-carboxylate was achieved by chiral SFC using a CHIRALPAK® AD-H column with 20% iPrOH in $CO_2$ to afford ethyl 1-(6-(2-((3-ethyl-4-(1-((S)-2-hydroxypropanoyl)piperidin-4-yl)phenoxy)methyl)-3-methylcyclohex-1-en-1-yl)pyridin-2-yl)-5-methyl-1H-pyrazole-4-carboxylate (diastereomer-1, $t_r$=16.0 min) and ethyl 1-(6-(2-((3-ethyl-4-(1-((S)-2-hydroxypropanoyl)piperidin-4-yl)phenoxy)methyl)-3-methylcyclohex-1-en-1-yl)pyridin-2-yl)-5-methyl-1H-pyrazole-4-carboxylate (diastereomer-2, $t_r$=19.5 min).

Example 19a. 1-(6-(2-((3-Ethyl-4-(1-((S)-2-hydroxypropanoyl)piperidin-4-yl)phenoxy)methyl)-3-methylcyclohex-1-en-1-yl)pyridin-2-yl)-5-methyl-1H-pyrazole-4-carboxylic acid (diastereomer-1)

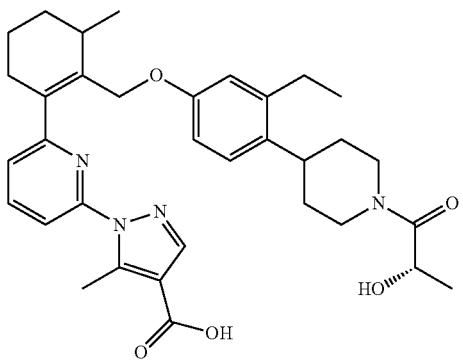 [SMILES: CCc1cc(OCC2=C(c3cccc(-n4ncc(C(=O)O)c4C)n3)CCCC2C)ccc1C1CCN(C(=O)[C@H](C)O)CC1]

The title compound was synthesized by a saponification of ethyl 1-(6-(2-((3-ethyl-4-(1-((S)-2-hydroxypropanoyl)piperidin-4-yl)phenoxy)methyl)-3-methylcyclohex-1-en-1-yl)pyridin-2-yl)-5-methyl-1H-pyrazole-4-carboxylate (diastereomer-1, $t_r$=16.0 min) by the method described in Example 16a. $^1$H NMR (400 MHz, DMSO-$d_6$) δ 7.91-8.04 (m, 2H) 7.63-7.72 (m, 1H) 7.32-7.40 (m, 1H) 7.00 (d, J=8.08 Hz, 1H) 6.49-6.67 (m, 2H) 4.79 (br. s., 1H) 4.35-4.55 (m, 5H) 4.05 (d, J=14.02 Hz, 1H) 3.08 (t, J=11.87 Hz, 1H) 2.88 (t, J=11.68 Hz, 1H) 2.78 (s, 3H) 2.54 (d, J=7.45 Hz, 5H) 1.79 (d, J=7.96 Hz, 2H) 1.62 (d, J=12.88 Hz, 3H) 1.34-1.55 (m, 3H) 1.13-1.24 (m, 6H) 1.07 (t, J=7.52 Hz, 3H). HRMS; calcd. for $C_{34}H_{43}N_4O_6$ (M+H) 587.3233, found 587.3218.

Example 19b. 1-(6-(2-((3-Ethyl-4-(1-((S)-2-hydroxypropanoyl)piperidin-4-yl)phenoxy)methyl)-3-methylcyclohex-1-en-1-yl)pyridin-2-yl)-5-methyl-1H-pyrazole-4-carboxylic acid (diastereomer-2)

Ethyl 1-(6-(2-((3-ethyl-4-(1-((S)-2-hydroxypropanoyl)piperidin-4-yl)phenoxy)methyl)-3-methylcyclohex-1-en-1-yl)pyridin-2-yl)-5-methyl-1H-pyrazole-4-carboxylate (diastereomer-2, $t_r$=19.5 min). was saponified as described in Example 16a to afford the title compound. $^1$H-NMR (400 MHz, DMSO-$d_6$) δ 12.50 (br. s., 1H), 7.94-8.02 (m, 2H), 7.68 (dd, J=0.63, 8.08 Hz, 1H), 7.36 (dd, J=0.69, 7.64 Hz, 1H), 6.97-7.03 (m, 1H), 6.57-6.64 (m, 2H), 4.72-4.86 (m, 1H), 4.37-4.55 (m, 4H), 4.00-4.11 (m, 1H), 3.02-3.15 (m, 1H), 2.84-2.95 (m, 1H), 2.78 (s, 3H), 2.52-2.71 (m, 5H), 2.31-2.42 (m, 1H), 1.73-1.86 (m, 2H), 1.30-1.72 (m, 6H), 1.12-1.24 (m, 6H), 1.07 (t, J=7.52 Hz, 3H). HRMS; calcd. for $C_{34}H_{43}N_4O_6$ (M+H) 587.3233, found 587.3223.

Example 20

Example 20(a). (±)-1-(6-(2-((4-(1-(Cyclopropanecarbonyl)piperidin-4-yl)-3-ethylphenoxy)methyl)-3-methylcyclohex-1-en-1-yl)pyridin-2-yl)-5-(difluoromethyl)-1H-pyrazole-4-carboxylic acid

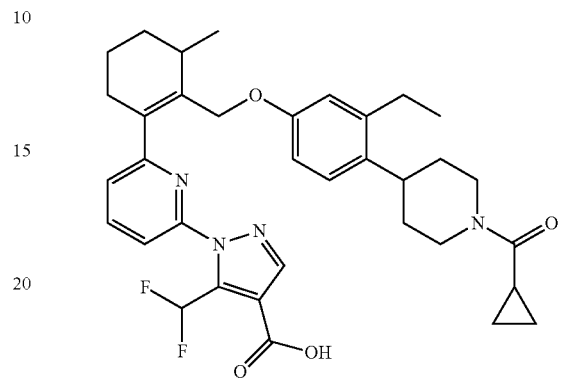

The title compound was synthesized starting from ethyl 1-(6-bromopyridin-2-yl)-5-(difluoromethyl)-1H-pyrazole-4-carboxylate (Intermediate 1-2-3). The sequence began with reaction of Intermediate 1-2-3 with bis(pinacolato)diboron and subsequent Suzuki coupling with (±)-tert-butyl 4-(2-ethyl-4-((6-methyl-2-(((trifluoromethyl)-sulfonyl)oxy)cyclohex-1-en-1-yl)methoxy)phenyl)piperidine-1-carboxylate (Intermediate 10) analogous to the transformation outlined for Example 17-C(a), and then saponification analogous to the method described in Example 16a to afford the title compound. $^1$H NMR (400 MHz, DMSO-$d_6$) δ 13.25 (br. s., 1H) 8.19 (s, 1H) 8.03 (t, J=7.8 Hz, 1H) 7.67 (d, J=8.1 Hz, 1H) 7.62 (t, J=52.4 Hz, 1H) 7.45 (d, J=7.6 Hz, 1H) 7.03 (d, J=8.2 Hz, 1H) 6.56-6.67 (m, 2H) 4.44-4.56 (m, 2H) 4.27-4.44 (m, 2H) 3.09-3.22 (m, 1H) 2.94-2.84 (m, 1H) 2.53-2.71 (m, 5H) 2.28-2.40 (m, 1H) 1.93-2.04 (m, 1H) 1.31-1.86 (m, 8H) 1.15 (d, J=6.8 Hz, 3H) 1.08 (t, J=7.5 Hz, 3H) 0.62-0.83 (m, 4H). HRMS; calcd. for $C_{35}H_{41}F_2N_4O_4$ (M+H) 619.3096, found 619.3074.

Example 20(b). (+) and (−)-1-(6-(2-((4-(1-(Cyclopropanecarbonyl)piperidin-4-yl)-3-ethylphenoxy)methyl)-3-methylcyclohex-1-en-1-yl)pyridin-2-yl)-5-(difluoromethyl)-1H-pyrazole-4-carboxylic acid Resolution of the enantiomers of (±)-1-(6-(2-((4-(1-(cyclopropanecarbonyl)piperidin-4-yl)-3-ethylphenoxy)methyl)-3-methylcyclohex-1-en-1-yl)pyridin-2-yl)-5-(difluoromethyl)-1H-pyrazole-4-carboxylic acid was achieved by chiral SFC using a CHIRALPAK® AD-H column with 25% MeOH in $CO_2$ to afford (+)-1-(6-(2-((4-(1-(cyclopropanecarbonyl)piperidin-4-yl)-3-ethylphenoxy)methyl)-3-methylcyclohex-1-en-1-yl)pyridin-2-yl)-5-(difluoromethyl)-1H-pyrazole-4-carboxylic acid (enantiomer-1, $t_r$=3.6 min) and (−)-1-(6-(2-((4-(1-(cyclopropanecarbonyl)piperidin-4-yl)-3-ethylphenoxy)methyl)-3-methylcyclohex-1-en-1-yl)pyridin-2-yl)-5-(difluoromethyl)-1H-pyrazole-4-carboxylic acid (enantiomer-2, $t_r$=4.4 min).

Example 21

Example 21-A. Ethyl 1-(6-(2-(hydroxymethyl)cyclopent-1-en-1-yl)pyridin-2-yl)-5-(trifluoromethyl)-1H-pyrazole-4-carboxylate

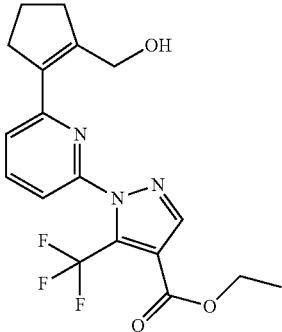 [SMILES: CCOC(=O)c1cnn(-c2cccc(C3=C(CO)CCC3)n2)c1C(F)(F)F]

The title compound was synthesized employing the method described for the synthesis of Intermediate 9 starting from ethyl 1-(6-bromopyridin-2-yl)-5-(trifliuoromethyl)-1H-pyrazole-4-carboxylate (Intermediate 1-1) and using ((2-bromocyclopent-1-en-1-yl)methoxy)(tert-butyl)dimethylsilane (Intermediate 12) in the place of Intermediate 4. MS (ESI+) m/z 382.2 (M+H).

Example 21-B. Ethyl 1-(6-(2-((4-(1-cyclopropanecarbonyl)piperidin-4-yl)-2-methylphenoxy)methyl)cyclopent-1-en-1-yl)pyridin-2-yl)-5-(trifluoromethyl)-1H-pyrazole-4-carboxylate

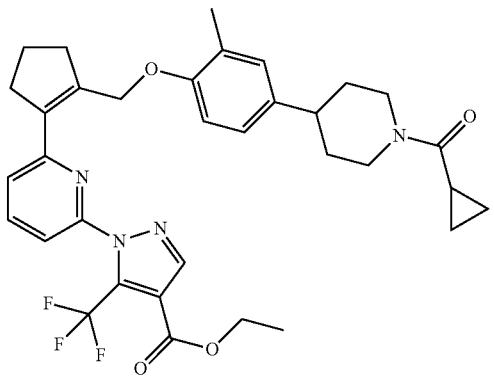 [SMILES: CCOC(=O)c1cnn(-c2cccc(C3=C(COc4ccc(C5CCN(C(=O)C6CC6)CC5)cc4C)CCC3)n2)c1C(F)(F)F]

To a suspension of cyclopropyl(4-(4-hydroxy-3-methylphenyl)piperidin-1-yl)methanone (Intermediate 2-4) (50 mg, 0.19 mmol), ethyl 1-(6-(2-(hydroxymethyl)cyclopent-1-en-1-yl)pyridin-2-yl)-5-(trifluoromethyl)-1H-pyrazole-4-carboxylate and cyclopropyl(4-(4-hydroxy-3-methylphenyl)piperidin-1-yl)methanone (77 mg, 0.20 mmol) in toluene (2.7 mL) was added tri-n-butyl cyanomethylenephosphorane (CAS#157141-27-0, 0.11 mL, 0.39 mmol). The mixture was then stirred at 100° C. for 40 min, and then cooled to room temperature. The mixture was directly purified by silica gel flash column chromatography (0-20% EtOAC in DCM) to afford the title compound. MS (ESI+) m/z 623.3 (M+H).

Example 21. 1-(6-(2-((4-(1-(Cyclopropanecarbonyl)piperidin-4-yl)-2-methylphenoxy)methyl)cyclopent-1-en-1-yl)pyridin-2-yl)-5-(trifluoromethyl)-1H-pyrazole-4-carboxylic acid

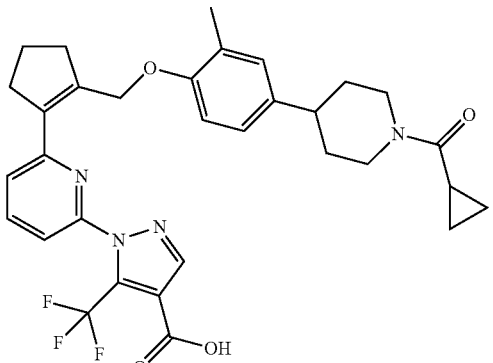

Saponification of ethyl 1-(6-(2-((4-(1-(cyclopropanecarbonyl)piperidin-4-yl)-2-methylphenoxy)methyl)cyclopent-1-en-1-yl)pyridin-2-yl)-5-(trifluoromethyl)-1H-pyrazole-4-carboxylate by the method described in Example 7 followed by RP-HPLC (HC-B) to furnish the title compound. $^1$H NMR (400 MHz, CD$_3$OD) δ 13.44 (br. s., 1H), 8.29 (s, 1H), 8.14 (t, J=7.9 Hz, 1H), 7.64 (d, J=7.8 Hz, 1H), 7.59 (d, J=7.8 Hz, 1H), 7.00 (d, J=1.8 Hz, 1H), 6.87 (dd, J=2.1, 8.3 Hz, 1H), 6.62 (d, J=8.4 Hz, 1H), 5.04 (s, 2H), 4.49 (d, J=12.1 Hz, 1H), 4.34 (d, J=12.2 Hz, 1H), 3.12 (t, J=12.1 Hz, 1H), 2.88 (t, J=7.2 Hz, 2H), 2.73 (t, J=7.2 Hz, 2H), 2.69-2.61 (m, 2H), 2.11 (s, 3H), 2.02-1.88 (m, 3H), 1.82-1.66 (m, 2H), 1.55-1.31 (m, 2H), 0.80-0.66 (m, 4H). HRMS; calcd. for C$_{32}$H$_{34}$F$_3$N$_4$O$_4$ (M+H) 595.2532, found 595.2549.

Example 22

Example 22-A. (±)-Ethyl 1-(6-(2-(hydroxymethyl)-3-methylcyclopent-1-en-1-yl)pyridin-2-yl)-5-(trifluoromethyl)-1H-pyrazole-4-carboxylate

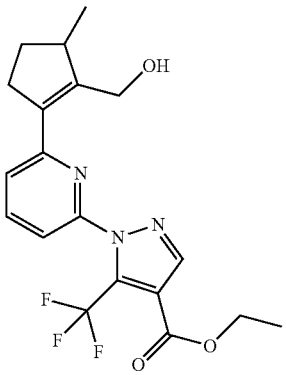 [SMILES: CCOC(=O)c1cnn(-c2cccc(C3=C(CO)C(C)CC3)n2)c1C(F)(F)F]

The title compound was synthesized as outlined for the synthesis of Intermediate 9 starting from ethyl 1-(6-bromopyridin-2-yl)-5-(trifliuoromethyl)-1H-pyrazole-4-carboxylate (Intermediate 1-1) and using (±)-2-(((tert-butyldimethylsilyl)oxy)methyl)-3-methylcyclopent-1-en-1-yl trifluoromethanesulfonate (Intermediate 11-C) in the place of Intermediate 4. MS (ESI+) m/z 396.3 (M+H).

Example 22(a). (±)-1-(6-(2-((4-(1-(Cyclopropanecarbonyl)piperidin-4-yl)-3-ethylphenoxy)methyl)-3-methylcyclopent-1-en-1-yl)pyridin-2-yl)-5-(trifluoromethyl)-1H-pyrazole-4-carboxylic acid

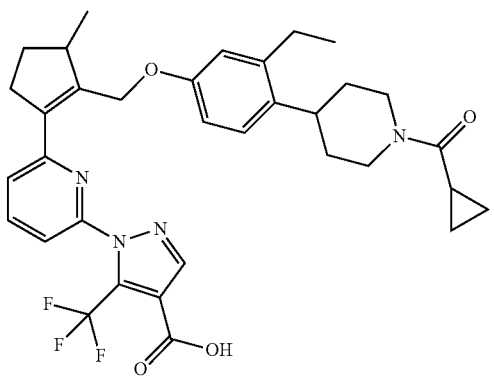 [SMILES: CCc1cc(OCC2=C(c3cccc(-n4ncc(C(=O)O)c4C(F)(F)F)n3)CCC2C)ccc1C1CCN(C(=O)C2CC2)CC1]

The title compound was synthesized starting from (±)-ethyl 1-(6-(2-(hydroxymethyl)-3-methylcyclopent-1-en-1-yl)pyridin-2-yl)-5-(trifluoromethyl)-1H-pyrazole-4-carboxylate, which was reacted with tert-butyl 4-(2-ethyl-4-hydroxyphenyl)piperidine-1-carboxylate (Intermediate 2-2) by the method described for Example 14. Purification was accomplished by RP-HPLC (HC-B) to furnish the title compound. $^1$H NMR (400 MHz, DMSO-$d_6$) δ 13.43 (s, 1H), 8.28 (s, 1H), 8.14 (t, J=7.9 Hz, 1H), 7.66 (d, J=7.9 Hz, 1H) 7.59 (m, 1H), 7.02 (d, J=8.5 Hz, 1H), 6.65-6.56 (m, 2H), 5.25 (d, J=13.2 Hz, 1H), 4.72 (d, J=13.2 Hz, 1H), 4.61-4.22 (m, 2H), 3.21-3.11 (m, 1H), 3.05 (q, J=7.2 Hz, 1H), 2.97-2.73 (m, 3H), 2.70-2.57 (m, 1H), 2.10-2.21 (m, 1H), 2.05-1.92 (m, 1H), 1.77-1.29 (m, 6H), 1.16 (d, J=6.9 Hz, 3H), 1.04 (t, J=7.5 Hz, 3H), 0.80-0.64 (m, 4H). HRMS; calcd. for $C_{34}H_{37}F_3N_4O_4$ (M+H) 623.2845, found 623.2818.

Example 22(b). (+)- and (−)-1-(6-(2-((4-(1-(Cyclopropanecarbonyl)piperidin-4-yl)-3-ethylphenoxy) methyl)-3-methylcyclopent-1-en-1-yl)pyridin-2-yl)-5-(trifluoromethyl)-1H-pyrazole-4-carboxylic acid Resolution of the enantiomers of (±)-1-(6-(2-((4-(1-(cyclopropanecarbonyl)piperidin-4-yl)-3-ethylphenoxy) methyl)-3-methylcyclopent-1-en-1-yl)pyridin-2-yl)-5-(trifluoromethyl)-1H-pyrazole-4-carboxylic acid was achieved by chiral SFC using a CHIRALPAK® AD-H column with 5-55% MeOH in $CO_2$ to afford (+)-1-(6-(2-((4-(1-(cyclopropanecarbonyl)piperidin-4-yl)-3-ethylphenoxy)methyl)-3-methylcyclopent-1-en-1-yl)pyridin-2-yl)-5-(trifluoromethyl)-1H-pyrazole-4-carboxylic acid (enantiomer-1, $t_r$=3.9 min) and (−)-1-(6-(2-((4-(1-(cyclopropanecarbonyl)piperidin-4-yl)-3-ethylphenoxy)methyl)-3-methylcyclopent-1-en-1-yl)pyridin-2-yl)-5-(trifluoromethyl)-1H-pyrazole-4-carboxylic acid (enantiomer-2, $t_r$=4.2 min).

Example 23

Example 23-A. tert-Butyl 4-(4-((2-(6-(4-(ethoxycarbonyl)-5-(trifluoromethyl)-1H-pyrazol-1-yl)pyridin-2-yl)cyclopent-1-en-1-yl)methoxy)-3-methylphenyl) piperidine-1-carboxylate

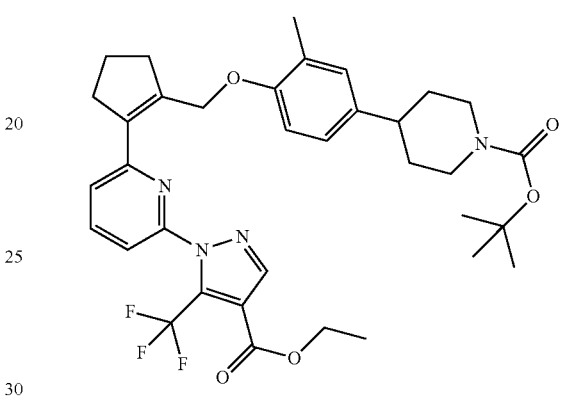

The title compound was synthesized by reaction of ethyl 1-(6-(2-(hydroxymethyl)cyclopent-1-en-1-yl)pyridin-2-yl)-5-(trifluoromethyl)-1H-pyrazole-4-carboxylate (Example 21-A) with tert-butyl 4-(4-hydroxy-3-methylphenyl)piperidine-1-carboxylate (Intermediate 2-1) by a similar manner as described in the synthesis of Example 1-A. MS (ESI+) m/z 655.4 (M+H).

Example 23-B. Ethyl 1-(6-(2-((2-methyl-4-(piperidin-4-yl)phenoxy)methyl)cyclopent-1-en-1-yl)pyridin-2-yl)-5-(trifluoromethyl)-1H-pyrazole-4-carboxylate

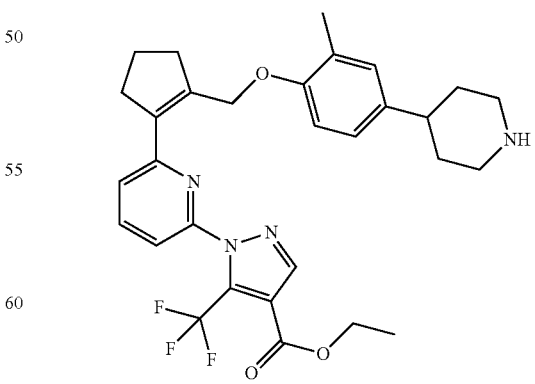

The title compound was synthesized by removal of the Boc group with the method described for the synthesis of Example 1-B. MS (ESI+) m/z 555.3 (M+H).

Example 23. 1-(6-(2-((4-(1-(Dimethylcarbamoyl)piperidin-4-yl)-2-methylphenoxy)methyl)cyclopent-1-en-1-yl)pyridin-2-yl)-5-(trifluoromethyl)-1H-pyrazole-4-carboxylic acid

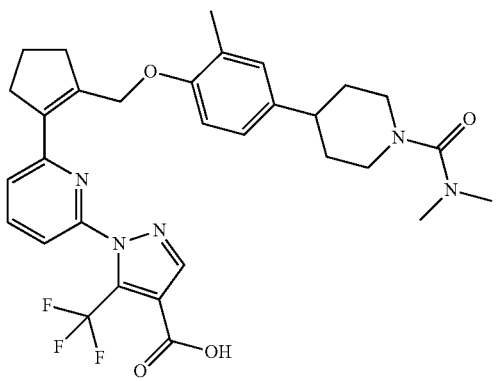 [SMILES: Cc1cc(C2CCN(C(=O)N(C)C)CC2)ccc1OCC1=C(c2cccc(-n3ncc(C(=O)O)c3C(F)(F)F)n2)CCC1]

To a solution of ethyl 1-(6-(2-((2-methyl-4-(piperidin-4-yl)phenoxy)methyl)cyclopent-1-en-1-yl)pyridin-2-yl)-5-(trifluoromethyl)-1H-pyrazole-4-carboxylate (19 mg, 0.034 mmol) in DCM (2 mL) was added DIPEA (0.024 mL, 0.14 mmol) followed by dimethylcarbamyl chloride (CAS#79-44-7, 7.4 mg, 0.069 mmol). The mixture was then stirred at room temperature for 1 h, and then concentrated. The resulting residue was dissolved in THF/MeOH (1 mL/0.1 mL). To the mixture was added 1N aq. NaOH (0.2 mL, 0.2 mmol), and then the mixture was stirred at 50° C. for 1 h. To the mixture was then added 1N aq. NaOH (0.4 mL), and then the mixture was stirred at 50° C. for another 1 h, and then cooled to room temperature. The mixture was then rendered acidic by conc. HCl, which was then purified by RP-HPLC (HC-B) to afford the title compound. $^1$H NMR (400 MHz, DMSO-$d_6$) δ 13.50 (br. s., 1H), 8.17 (br. s., 1H), 8.12 (t, J=7.9 Hz, 1H), 7.62 (d, J=7.8 Hz, 1H), 7.56 (d, J=7.7 Hz, 1H), 7.00 (d, J=1.8 Hz, 1H), 6.87 (dd, J=2.1, 8.4 Hz, 1H), 6.63 (d, J=8.4 Hz, 1H), 5.04 (s, 2H), 3.62 (d, J=13.1 Hz, 2H), 2.88 (t, J=7.5 Hz, 2H), 2.77-2.69 (m, 10H), 2.6-2.5 (2H, m), 2.12 (s, 3H), 1.92 (app. quin, J=7.6 Hz, 2H), 1.68 (dd, J=1.8, 12.8 Hz, 2H), 1.50 (dq, J=3.7, 12.5 Hz, 2H). HRMS; calcd. for $C_{31}H_{35}F_3N_5O_4$ (M+H) 598.2641, found 598.2655.

Example 24

The following compounds were prepared by similar methods as described for the synthesis of Example 23 by using Intermediate 23-B, and Reagent-A instead of dimethylcarbamyl chloride, as delineated in the table below.

| Example | Structure/Name | Reagent-A | Analytical Data |
|---|---|---|---|
| 24-1 | 1-(6-(2-((4-(1-(2-Hydroxyacetyl)piperidin-4-yl)-2-methylphenoxy)methyl)cyclopent-1-en-1-yl)pyridin-2-yl)-5-(trifluoromethyl)-1H-pyrazole-4-carboxylic acid | 2-chloro-2-oxoethyl acetate (CAS# 13831-31-7) | $^1$H NMR (400 MHz, DMSO-$d_6$) δ 13.45 (br. s, 1H) 8.06-8.16 (m, 2H) 7.60 (d, J = 7.8 Hz, 1H) 7.55 (d, J = 7.8 Hz, 1H) 6.99 (s, 1H) 6.87 (dd, J = 8.4, 2.2 Hz, 1H) 6.63 (d, J = 8.4 Hz, 1H) 5.04 (s, 2H) 4.37-4.52 (m, 2H) 4.02-4.17 (m, 2H) 3.74 (br. d, J = 13.0 Hz, 1H) 3.01 (app. t, J = 12.3 Hz, 1H) 2.84-2.92 (m, 2 H) 2.69-2.76 (m, 2H) 2.58-2.65 (m, 2H) 2.11 (s, 3H) 1.92 (quin, J = 7.5 Hz, 2H) 1.67-1.77 (m, 2H) 1.28-1.58 (m, 2H) HRMS calcd. for $C_{30}H_{32}F_3N_4O_5$ (M + H) 585.2325, found 585.2339. |

| Example | Structure/Name | Reagent-A | Analytical Data |
|---|---|---|---|
| 24-2 | 1-(6-(2-((2-Methyl-4-(1-propionylpiperidin-4-yl)phenoxy)methyl)cyclopent-1-en-1-yl)pyridin-2-yl)-5-(trifluoromethyl)-1H-pyrazole-4-carboxylic acid | Propionic anhydride (CAS# 123-62-6) | $^1$H NMR (400 MHz, DMSO-$d_6$) δ 13.48 (br. s., 1H), 8.20-8.04 (m, 2H), 7.61 (d, J = 7.8 Hz, 1H), 7.55 (d, J = 7.7 Hz, 1H), 6.99 (d, J = 1.7 Hz, 1H), 6.87 (dd, J = 2.2, 8.3 Hz, 1H), 6.63 (d, J = 8.4 Hz, 1H), 5.04 (s, 2H), 4.52 (d, J = 12.3 Hz, 1H), 3.92 (d, J = 13.3 Hz, 1H), 3.04 (t, J = 12.0 Hz, 1H), 2.88 (t, J = 6.6 Hz, 2H), 2.76-2.69 (m, 2H), 2.63-2.56 (m, 2H), 2.33 (q, J = 7.4 Hz, 2H), 2.11 (s, 3H), 1.92 (quin, J = 7.7 Hz, 2H), 1.71 (t, J = 12.1 Hz, 2H), 1.54-1.29 (m, 2H), 0.99 (t, J = 7.4 Hz, 3H). HRMS calcd. for $C_{31}H_{34}F_3N_4O_4$ (M + H) 583.2532, found 583.2552. |
| 24-3 | 1-(6-(2-((4-(1-(Methoxycarbonyl)piperidin-4-yl)-2-methylphenoxy)methyl)cyclopent-1-en-1-yl)pyridin-2-yl)-5-(trifluoromethyl)-1H-pyrazole-4-carboxylic acid | Methyl chloroformate (CAS# 79-22-1) | $^1$H NMR (400 MHz, DMSO-$d_6$) δ 13.43 (br. s., 1H), 8.29 (s, 1H), 8.14 (t, J = 7.9 Hz, 1H), 7.65 (d, J = 7.7 Hz, 1H), 7.59 (d, J = 7.8 Hz, 1H), 6.99 (d, J = 1.8 Hz, 1H), 6.86 (dd, J = 2.1, 8.3 Hz, 1H), 6.62 (d, J = 8.4 Hz, 1H), 5.04 (s, 2H), 4.06 (d, J = 10.3 Hz, 2H), 3.60 (s, 3H), 2.92-2.85 (m, J = 7.2 Hz, 2H), 2.85-2.77 (m, 2H), 2.72 (t, J = 7.3 Hz, 2H), 2.61-2.55 (m, 1H), 2.11 (s, 3H), 1.92 (quin, J = 7.5 Hz, 2H), 1.69 (d, J = 12.5 Hz, 2H), 1.43 (dq, J = 4.3, 12.6 Hz, 2H). HRMS calcd. for $C_{30}H_{32}F_3N_4O_5$ (M + H) 585.2325, found 585.2341. |
| 24-4 | 1-(6-(2-((2-Methyl-4-(1-(methylsulfonyl)piperidin-4-yl)phenoxy)methyl)cyclopent-1-en-1-yl)pyridin-2-yl)-5-(trifluoromethyl)-1H-pyrazole-4-carboxylic acid | methanesulfonyl chloride (CAS # 124-63-0) | $^1$H NMR (400 MHz, CD$_3$OD) δ 13.49 (br. s, 1H), 8.21-8.08 (m, 2H), 7.62 (d, J = 7.9 Hz, 1H), 7.56 (d, J = 7.7 Hz, 1H), 7.02 (s, 1H), 6.90 (d, J = 8.2 Hz, 1H), 6.64 (d, J = 8.4 Hz, 1H), 5.05 (br. s., 2H), 3.64 (d, J = 11.5 Hz, 2H), 2.88 (br. s, 5H), 2.8 -2.65 (m, 5H), 2.12 (s, 3H), 1.92 (quin, J = 7.4 Hz, 2H), 1.80 (d, J = 12.1 Hz, 2H), 1.59 (dq, J = 3.9, 12.6 Hz, 2H). HRMS calcd. for $C_{29}H_{32}F_3N_4O_5S$ (M + H) 605.2046, found 605.2072. |

Example 25. 1-(6-(2-((2-Methyl-4-(1-(2,2,2-trifluoroethyl)piperidin-4-yl)phenoxy)methyl)cyclopent-1-en-1-yl)pyridin-2-yl)-5-(trifluoromethyl)-1H-pyrazole-4-carboxylic acid

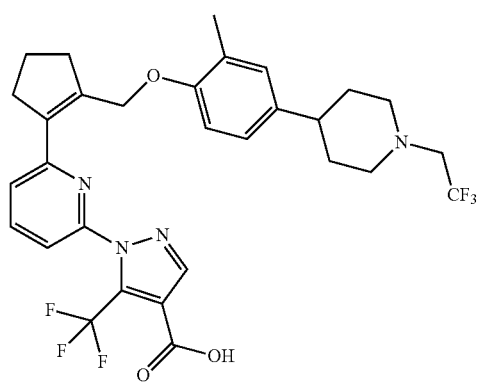 [SMILES: Cc1cc(C2CCN(CC(F)(F)F)CC2)ccc1OCC1=C(c2cccc(-n3ncc(C(=O)O)c3C(F)(F)F)n2)CCC1]

To a solution of ethyl 1-(6-(2-((2-methyl-4-(piperidin-4-yl)phenoxy)methyl)cyclopent-1-en-1-yl)pyridin-2-yl)-5-(trifluoromethyl)-1H-pyrazole-4-carboxylate (Example 23-B) (19 mg, 0.034 mmol) in THF (2 mL) was added K$_2$CO$_3$ (14.2 mg, 0.11 mmol) followed by 2,2,2-trifluoroethyl trifluoromethanesulfonate (12.7 mg, 0.055 mmol). The mixture was then stirred at 45° C. for 1 h. To the mixture was then added MeOH (0.1 mL), followed by 1N aq. NaOH (0.2 mL, 0.2 mmol), and then the mixture was stirred at 50° C. for 1 h. To the mixture was then added 1N aq. NaOH (0.4 mL), and then the mixture was stirred at 50° C. for another 1 h, and then cooled to room temperature. The mixture was then rendered acidic by conc. HCl, which was then purified by RP-HPLC (HC-B) to afford the title compound. $^1$H NMR (400 MHz, DMSO-d$_6$) δ 13.55 (br. s., 1H), 8.11 (s, 2H), 7.60 (d, J=7.8 Hz, 1H), 7.54 (d, J=7.7 Hz, 1H), 7.00 (d, J=2.0 Hz, 1H), 6.88 (dd, J=2.1, 8.4 Hz, 1H), 6.63 (d, J=8.4 Hz, 1H), 6.41-6.41 (m, 1H), 5.03 (s, 2H), 3.16 (q, J=10.3 Hz, 2H), 2.97 (d, J=11.5 Hz, 2H), 2.88 (t, J=7.2 Hz, 2H), 2.72 (t, J=7.3 Hz, 2H), 2.45-2.36 (m, 2H), 2.11 (s, 3H), 1.92 (quin, J=7.5 Hz, 2H), 1.70-1.53 (m, 4H). HRMS; calcd. for C$_{30}$H$_{31}$F$_6$N$_4$O$_3$ (M+H) 609.2300, found 609.2318.

Example 26

Example 26-A. Ethyl 1-(6-(2-formylcyclohex-1-en-1-yl)pyridin-2-yl)-5-(trifluoromethyl)-1H-pyrazole-4-carboxylate

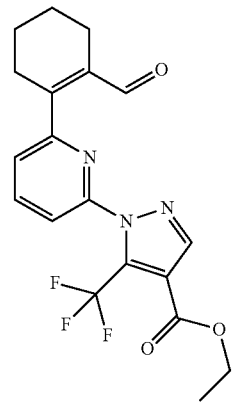 [SMILES: CCOC(=O)c1cnn(-c2cccc(C3=C(C=O)CCCC3)n2)c1C(F)(F)F]

A DCM (10 mL) suspension of Intermediate 9 (744 mg, 1.88 mmol) and manganese dioxide (CAS #1313-13-9, 3.27 g, 37.6 mmol) was vigorously stirred at room temperature for 16 h. The suspension was filtered through a plug of Celite® and the resulting DCM eluent was used directly in the next step without concentration or additional purification. MS (ESI+) m/z 394.3 (M+H).

Example 26-B. tert-butyl 4-(4-(((2-(6-(4-(ethoxycarbonyl)-5-(trifluoromethyl)-1H-pyrazol-1-yl)pyridin-2-yl)cyclohex-1-en-1-yl)methyl)amino)-2-ethylphenyl)piperidine-1-carboxylate

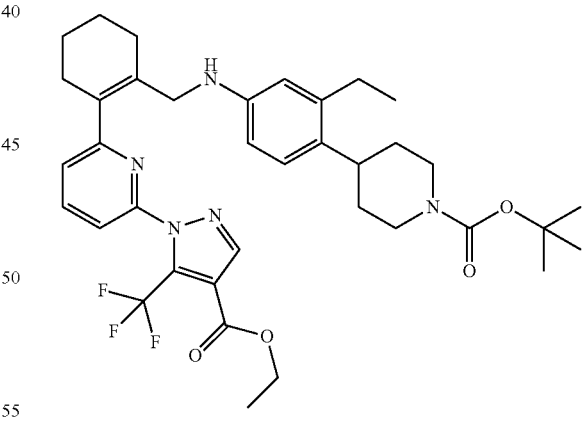

The DCM eluent from Example 26-A was added to an acetic acid solution (15 mL) of Intermediate 13 (0.57 g, 1.9 mmol) at room temperature. The mixture was partially concentrated under reduced pressure to remove most of the DCM and afford a volume of 15 mL. Sodium triacetoxyborohydride (CAS #56553-60-7, 558 mg, 2.63 mmol) was then added to the mixture, and then the mixture was stirred at room temperature for 30 min. The reaction mixture was diluted with EtOAc (25 mL). A solution of 28% aq. NH$_4$OH was then added to the mixture to achieve a pH 10. The resulting layers were then separated and the organic phase was washed with water, brine, and dried over sodium sulfate. The resulting residue was purified by silica gel flash column chromatography (0% to 100% EtOAc in heptane) to afford the title compound. MS (ESI+) m/z 682.7 (M+H).

Example 26. 1-(6-(2-(((4-(1-(Cyclopropanecarbonyl)piperidin-4-yl)-3-ethylphenyl)amino)methyl)cyclohex-1-en-1-yl)pyridin-2-yl)-5-(trifluoromethyl)-1H-pyrazole-4-carboxylic acid

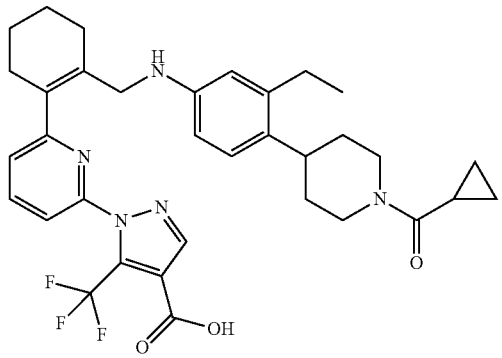 [SMILES: CCc1cc(NCC2=C(c3cccc(-n4ncc(C(=O)O)c4C(F)(F)F)n3)CCCC2)ccc1C1CCN(C(=O)C2CC2)CC1]

The title compound was synthesized starting from tert-butyl 4-(4-(((2-(6-(4-(ethoxycarbonyl)-5-(trifluoromethyl)-1H-pyrazol-1-yl)pyridin-2-yl)cyclohex-1-en-1-yl)methyl)amino)-2-ethylphenyl)piperidine-1-carboxylate, which was treated with TFA, in a fashion analogous Example 14-D, to afford the unprotected piperidine, which was then reacted with cyclopropanecarboxylic acid in an analogous fashion to the transformation outlined in Example 3-A. The resulting product was saponified as described in Example 14 to furnish the title compound. $^1$H NMR (400 MHz, DMSO-$d_6$) δ 13.41 (br. s., 1H) 8.27 (s, 1H) 8.09 (app. t, J=7.8 Hz, 1H) 7.63-7.69 (m, 1H) 7.54-7.59 (m, 1H) 6.78 (d, J=8.4 Hz, 1H) 6.23 (br. dd, J=8.4, 2.4 Hz, 1H) 6.17 (br. d, J=2.4 Hz, 1H) 4.27-4.55 (m, 2H) 3.54 (s, 2H) 3.05-3.21 (m, 1H) 2.73-2.84 (m, 1H) 2.54-2.65 (m, 1H) 2.35-2.46 (m, 4H) 2.19 (br. s., 2H) 1.93-2.02 (m, 1H) 1.64 (br. s., 5H) 1.25-1.59 (m, 4H) 1.01 (t, J=7.5 Hz, 3H) 0.62-0.79 (m, 4H). HRMS calcd. for $C_{34}H_{39}F_3N_6O_3$ (M+H) 622.3005, found 622.2986.

Example 27

The following compounds were prepared with similar methods as described for Example 26. A reductive amination between Intermediate 25-A and the requisite aniline (Aniline-A), as delineated in the table below, afforded the coupling product employing the method described for Example 26-B, which was subsequently saponified by the method described in Example 14.

| Example | Structure/Name | Aniline-A | Analytical Data |
|---|---|---|---|
| 27-1 | 1-(6-(2-(((4-(1-(Cyclopropanecarbonyl)piperidin-4-yl)-2-methylphenyl)amino)methyl)cyclohex-1-en-1-yl)pyridin-2-yl)-5-(trifluoromethyl)-1H-pyrazole-4-carboxylic acid | Intermediate 14 | $^1$H NMR (400 MHz, DMSO-$d_6$) δ 8.15 (s, 1H), 8.07 (t, J = 7.8 Hz, 1H), 7.62 (d, J = 7.9 Hz, 1H), 7.57 (d, J = 7.7 Hz, 1H), 6.79 (d, J = 2.1 Hz, 1H), 6.69 (d, J = 8.9 Hz, 1H), 6.13 (d, J = 8.3 Hz, 1H), 4.76 (s, 1H), 4.46 (s, 1H), 4.31 (s, 1H), 3.65 (s, 2H), 3.11 (s, 1H), 2.47-2.41 (m, 1H), 2.38 (s, 2H), 2.17 (s, 2H), 2.01 (s, 3H), 2.00-1.92 (m, 1H), 1.63 (s, 5H), 1.78-1.70 (m, 1H), 1.51-1.22 (m, 2H), 0.68 (d, J = 7.9 Hz, 4H). HRMS calcd. for $C_{33}H_{37}F_3N_5O_3$ (M + H) 608.2848, found 608.2872. |

| Example | Structure/Name | Aniline-A | Analytical Data |
|---|---|---|---|
| 27-2 | 1-(6-(2-(((4-(1-(Cyclopropanecarbonyl)piperidin-4-yl)phenyl)amino)methyl)cyclohex-1-en-1-yl)pyridin-2-yl)-5-(trifluoromethyl)-1H-pyrazole-4-carboxylic acid | Intermediate 15 | $^1$H NMR (400 MHz, DMSO-d$_6$) δ 7.99 (t, J = 7.8 Hz, 1H), 7.82 (s, 1H), 7.55 (dd, J = 8.0, 0.8 Hz, 1H), 7.47 (dd, J = 7.7, 0.9 Hz, 1H), 6.90-6.80 (m, 2H), 6.42-6.32 (m, 2H), 5.57 (s, 1H), 4.46 (s, 1H), 4.34 (s, 1H), 3.55 (d, J = 3.6 Hz, 2H), 3.11 (s, 1H), 2.63-2.53 (m, 2H), 2.39 (s, 2H), 2.20 (s, 2H), 1.98 (p, J = 6.5 Hz, 1H), 1.74 (s, 1H), 1.70-1.58 (m, 5H), 1.44 (s, 1H), 1.32 (s, 1H), 0.68 (d, J = 8.7 Hz, 4H). HRMS calcd. for C$_{32}$H$_{35}$F$_3$N$_5$O$_3$ (M + H) 594.2692, found 594.2728. |

Example 28

Example 28-A. (±)-Ethyl 1-(6'-(hydroxymethyl)-3'-methyl-2',3',4',5'-tetrahydro-[1,1-biphenyl]-3-yl)-5-(trifluoromethyl)-1H-pyrazole-4-carboxylate

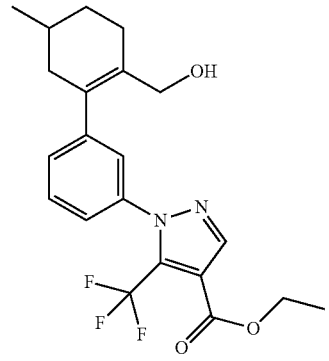 [SMILES: CCOC(=O)c1cnn(-c2cccc(C3=C(CO)CCC(C)C3)c2)c1C(F)(F)F]

To a suspension of (±)-2-(((tert-butyldimethylsilyl)oxy)methyl)-5-methylcyclohex-1-en-1-yl trifluoromethanesulfonate (Intermediate 6) (1 g, 2.6 mmol), ethyl 1-(3-(4,4,5,5-tetramethyl-1,3,2-dioxaborolan-2-yl)phenyl)-5-(trifluoromethyl)-1H-pyrazole-4-carboxylate (Intermediate 1-4) (1.6 g, 3.9 mmol) and K$_3$PO$_4$ (1.5 g, 7.1 mmol) in toluene/H$_2$O (10 mL/7 mL) was added PdCl$_2$(dppf)-CH$_2$Cl$_2$ adduct (0.4 g, 0.49 mmol). The mixture was stirred at 100° C. for 16 h, and then cooled to room temperature, and then diluted with EtOAc. The mixture was then washed successively with H$_2$O and brine, and then dried over Na$_2$SO$_4$. The extracts were filtered through a plug of silica gel, which was rinsed with EtOAc. The filtrate was concentrated. The resulting residue was charged with a solution of TBAF in THF (5 mL, 5 mmol) and was stirred at 40° C. for 2 h. The reaction mixture was diluted with EtOAc, and then washed successively with H$_2$O and brine, and then dried over Na$_2$SO$_4$. The extracts were filtered through a plug of silica gel, which was rinsed with EtOAc. The filtrate was concentrated. The resulting residue was purified by silica gel flash column chromatography (heptane/EtOAc=78/22 to 56/44) to afford the title compound. MS (ESI+) m/z 391.2 (M-OH)$^+$.

Example 28. (±)-1-(6'-((4-(1-(Cyclopropanecarbonyl)piperidin-4-yl)-2-methylphenoxy)methyl)-3'-methyl-2',3',4',5'-tetrahydro-[1,1-biphenyl]-3-yl)-5-(trifluoromethyl)-1H-pyrazole-4-carboxylic acid The title compound was synthesized by the method as outlined in the preparation of Example 12a, but using (±)-ethyl 1-(6'-(hydroxymethyl)-3'-methyl-2',3',4',5'-tetrahydro-[1,1'-biphenyl]-3-yl)-5-(trifluoromethyl)-1H-pyrazole-4-carboxylate in the place of Example 12-B. $^1$H NMR (400 MHz, CD$_3$OD) δ 8.11 (s, 1H), 7.47-7.53 (m, 1H), 7.31-7.41 (m, 2H), 7.19-7.24 (m, 1H), 6.90-6.93 (m, 1H), 6.85 (dd, J=2.2, 8.31 Hz, 1H), 6.49 (d, J=8.3 Hz, 1H), 4.61 (br. d, J=12.1 Hz, 1H), 4.42 (br. d, J=13.0 Hz, 1H), 4.25-4.33 (m, 2H), 3.16-3.28 (m, 1H), 2.62-2.76 (m, 2H), 2.40-2.51 (m, 2H), 2.29-2.40 (m, 1H), 2.11 (s, 3H), 1.94-2.07 (m, 2H), 1.73-1.91 (m, 4H), 1.42-1.65 (m, 2H), 1.27-1.42 (m, 1H), 1.04 (d, J=6.4 Hz, 3H), 0.73-0.93 (m, 4H). HRMS; calcd. for C$_{35}$H$_{39}$F$_3$N$_3$O$_4$(M+H) 622.2893, found 622.2872.

Example 29

The following compounds were prepared with similar methods as described for Example 7 using Alcohol-A, as delineated in the table below in the place of Intermediate 9 and Phenol-A, as delineated in the table below, instead of Intermediate 2-5-1.

compounds for 1 h room temperature, then assayed for cGMP production using Cisbio cGMP HTRF kit (62GM2PEC) according to manufacturer's instructions.

| Example | Structure/Name | Starting Materials Alcohol-A and Phenol-A | Analytical Data |
|---|---|---|---|
| 29-1 | (±)-1-(6-(3-Methyl-2-(((2-(pyridin-2-ylmethyl)-1,2,3,4-tetrahydroisoquinolin-6-yl)oxy)methyl)cyclohex-1-en-1-yl)pyridin-2-yl)-5-(trifluoromethyl)-1H-pyrazole-4-carboxylic acid | Example 13-B (Alcohol-A) and Intermediate 3-2 (Phenol-A) | $^1$H NMR (400 MHz, DMSO-$d_6$) δ 8.64 (ddd, J = 4.9, 1.8, 0.9 Hz, 1H), 8.00-7.91 (m, 2H), 7.89 (td, J = 7.7, 1.8 Hz, 1H), 7.62-7.50 (m, 2H), 7.47-7.37 (m, 2H), 6.92 (d, J = 8.5 Hz, 1H), 6.65 (dd, J = 8.5, 2.6 Hz, 1H), 6.56 (d, J = 2.5 Hz, 1H), 4.56 (d, J = 11.7 Hz, 1H), 4.44 (d, J = 11.7 Hz, 1H), 4.34 (s, 2H), 4.14 (s, 2H), 3.39 (ddt, J = 20.0, 3.3, 1.7 Hz, 2H), 3.0-2.79 (m, 2H), 2.56 (dd, J = 15.0, 8.8 Hz, 2H), 2.34 (d, J = 17.8 Hz, 1H), 1.85 (dd, J = 10.2, 5.0 Hz, 2H), 1.67 (dt, J = 7.5, 4.9 Hz, 1H), 1.53 (td, J = 9.8, 9.3, 6.1 Hz, 1H), 1.22 (d, J = 6.9 Hz, 3H). HRMS calcd. for $C_{33}H_{33}F_3N_5O_3$ (M + H) 604.2535, found 604.2540. |
| 29-2 | (±)-1-(6-(2-((4-((3,4-tans)-1-(cyclopropanecarbonyl)-3-hydroxypiperidin-4-yl)phenoxy)methyl)cyclohex-1-en-1-yl)pyridin-2-yl)-5-(trifluoromethyl)-1H-pyrazole-4-carboxylic acid | Intermediate 9 (Alcohol-A) and Intermediate 16 (Phenol-A) | $^1$H NMR (400 MHz, CD$_3$OD) δ 8.16 (s, 1H), 7.97 (t, J = 7.8 Hz, 1H), 7.57 (dd, J = 0.8, 8.0 Hz, 1H), 7.47 (dd, J = 0.8, 7.7 Hz, 1H), 7.11 (d, J = 8.7 Hz, 2H), 6.75 (d, J = 8.7 Hz, 2H), 4.66-4.76 (m, 1H), 4.30-4.59 (m, 4H), 3.49-3.70 (m, 1H), 2.94-3.25 (m, 1H), 2.42-2.75 (m, 4H), 2.34 (br. s., 2H), 1.95-2.06 (m, 1H), 1.72-1.92 (m, 5H), 1.49-1.72 (m, 1H), 0.76-0.95 (m, 4H). HRMS; calc. for $C_{32}H_{34}F_3N_4O_5$ (M + H) 611.2476, found 611.2527. |

Biological Example—1. CHO Cellular Assay

Chinese hamster ovary (CHO) cells overexpressing soluble guanylate cyclase were generated to test the effect of sGC activators in a cellular context. Human cDNAs for GUCYA3 (RefSeq: NM_000856.3) and GUCYB3 (RefSeq: NM_000857.1) were amplified by PCR from a HUVEC (Human Umbilical Vein Endothelial Cells) cDNA library and cloned into mammalian expression vectors. CHO K1 cells (ATCC CCL-61) were transfected using Lipofectamine 2000 following manufacturer's instructions and stably expressing clones were identified by antibiotic selection. CHO GUCY clone 8E10 was used for subsequent experiments.

Cells were seeded at a density of 3000 cells/well in white 384-well proxyplates (Perkin Elmer) and incubated overnight, then the medium was removed and cells were washed with assay buffer (HBSS, 0.1% BSA, 1 mM IBMX, 20 uM ODQ). sGC activators were serially diluted in DMSO, then diluted in assay buffer prior to adding to cells (10 ul/well, final DMSO concentration 0.5%). Cells were incubated with The EC50s are calculated based on the amount of cGMP interpolated from the standard curve, using a 4-parameter sigmoidal dose-response.

Compounds of invention are active on sGC activation. Data on Table 1 collected using the assay of Biological Example 1. The minimum $EC_{50}$ quantification limit of the assay is 0.5 nM, therefore any compound listed as having an $EC_{50}$ value of 0.5 nM has a actual $EC_{50}$ of ≤0.5 nM.

TABLE 1

| Example number | $EC_{50}$ (nM) |
|---|---|
| Example 1 | 0.5 |
| Example 2-1 | 0.5 |
| Example 2-2 | 1 |
| Example 2-3 | 1 |
| Example 2-4 | 1 |
| Example 2-5 | 2.4 |
| Example 2-6 | 6.3 |
| Example 2-7 | 2 |
| Example 2-8 | 0.5 |
| Example 2-9 | 1 |

TABLE 1-continued

| Example number | EC$_{50}$ (nM) |
| --- | --- |
| Example 2-10 | 0.5 |
| Example 2-11 | 1 |
| Example 2-12 | 14 |
| Example 2-13 | 110 |
| Example 3 | 0.5 |
| Example 4-1 | 164 |
| Example 4-2 | 8.4 |
| Example 5 | 10 |
| Example 6-1 | 2.8 |
| Example 6-2 | 16 |
| Example 6-3 | 374 |
| Example 7 | 1 |
| Example 8-1 | 5.5 |
| Example 8-2 | 34 |
| Example 9 | 0.5 |
| Example 10 | 1 |
| Example 11 | 110 |
| Example 12 (+) | 0.5 |
| Example 12 (−) | 0.5 |
| Example 13a | 1 |
| Example 13b | 9 |
| Example 14 | 1 |
| Example 15a | 0.5 |
| Example 15b | 1 |
| Example 16a | 0.5 |
| Example 16b | 3 |
| Example 17a | 0.5 |
| Example 17b | 1.4 |
| Example 18a | 0.5 |
| Example 18b | 8.9 |
| Example 19a | 0.5 |
| Example 19b | 8 |
| Example 20(b) (+) | 0.5 |
| Example 20b (−) | 2 |
| Example 21 | 2.4 |
| Example 22(b) (+) | 1 |
| Example 22(b) (−) | 5.5 |
| Example 23 | 3.5 |
| Example 24-1 | 19 |
| Example 24-2 | 2.4 |
| Example 24-3 | 22 |
| Example 24-4 | 2.4 |
| Example 25 | 5 |
| Example 26 | 0.5 |
| Example 27-1 | 2.4 |
| Example 27-2 | 5 |
| Example 28 | 22 |
| Example 29-1 | 3.9 |
| Example 29-2 | 420 |

What is claimed is:

1. A compound according to Formula (I)

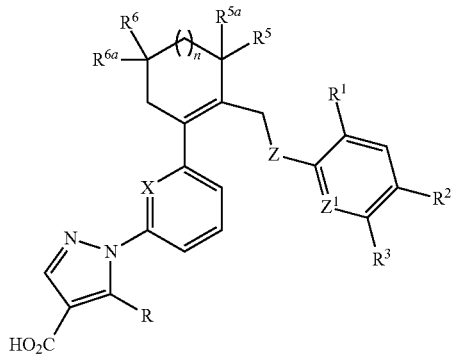

Or a pharmaceutically acceptable salt thereof, wherein
n is 0 or 1;
X is N or CH;
Z is N(H), O or CH$_2$;
Z$^1$ is CR$^4$ or N;
R is hydrogen, C$_1$-C$_4$alkyl, monofluoromethyl, difluoromethyl or trifluoromethyl;
R$^1$ is hydrogen, halogen, C$_1$-C$_4$alkyl or trifluoromethyl
R$^2$ is piperidinyl which is N-substituted with C$_1$-C$_4$alkyl, C$_3$-C$_6$cycloalkyl, haloC$_1$-C$_4$alkyl, C(O)C$_1$-C$_4$alkyl, S(O)$_2$C$_1$-C$_4$alkyl, C(O)C$_3$-C$_6$cycloalkyl, C(O)haloC$_1$-C$_4$alkyl, C(O)C$_1$-C$_4$alkoxy, C(O)C$_1$-C$_4$alkenoxy, heteroaryl or CO(O)$_2$benzyl, wherein each cycloalkyl is optionally substituted by hydroxy and each alkyl or alkoxy is optionally substituted by hydroxyl, C$_1$-C$_4$alkoxy or C$_3$-C$_6$cycloalkyl and wherein each heteroaryl has 5 or 6 ring atoms, 1, 2 or 3 ring heteroatoms independently selected from N, O and S and is optionally substituted with 1 or 2 C$_1$-C$_4$alkyl substituents, which piperidinyl ring is further optionally substituted by hydroxyl;
R$^3$ is hydrogen, halogen or C$_1$-C$_4$alkyl; or
R$^2$ and R$^3$, taken in combination, form a 5 or 6 member fused saturated azacyclic ring optionally substituted with benzyl or 5 or 6 member heteroarylmethyl, which heteroaryl has 1 or 2 ring heteroatoms independently selected from N, O and S;
R$^4$ is hydrogen or C$_1$-C$_4$alkyl;
R$^5$ and R$^{5a}$ are independently selected from the group consisting of hydrogen and C$_1$-C$_4$alkyl; or
R$^5$ and R$^{5a}$, taken in combination form a spirocyclic cyclopropyl ring; and
when n is 0, R$^6$ and R$^{6a}$ are each hydrogen and when n is 1, R$^6$ and R$^{6a}$ are independently selected from the group consisting of hydrogen and C$_1$-C$_4$alkyl; or
R$^6$ and R$^{6a}$, taken in combination form a spirocyclic cyclopropyl ring.

2. A compound according to Formula (Ia)

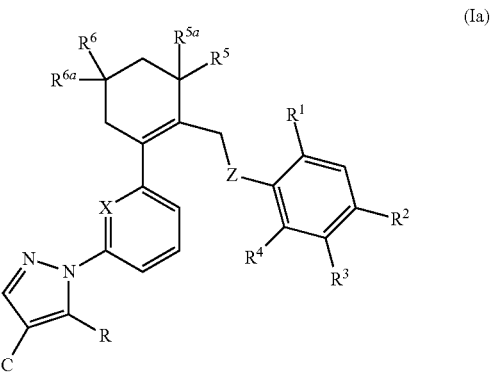

Or a pharmaceutically acceptable salt thereof, wherein
X is N or CH;
Z is O or CH$_2$;
R is C$_1$-C$_4$alkyl or trifluoromethyl;
R$^1$ and R$^4$ are each independently selected from hydrogen, halogen or C$_1$-C$_4$alkyl; or
R$^4$ is haloC$_1$-C$_4$alkyl;
R$^2$ is piperidinyl which is N-substituted with C$_1$-C$_4$alkyl, haloC$_1$-C$_4$alkyl, C$_3$-C$_6$cycloalkyl, C(O)C$_1$-C$_4$alkyl which is optionally substituted with hydroxyl or amino, C(O)C$_3$-C$_6$cycloalkyl, C(O)C$_1$-C$_4$alkoxy, C(O)NH(C$_1$-C$_4$alkyl), C(O)N(C$_1$-C$_4$alkyl)$_2$, S(O)$_2$C$_1$-C$_4$alkyl, S(O)$_2$ C$_3$-C$_6$cycloalkyl or C(O)heteroaryl which heteroaryl has 5 or 6 ring atoms and 1 or 2 ring heteroatoms independently selected from the group consisting of N, O and S;

R³ is hydrogen or C₁-C₄alkyl; or

R² and R³, taken in combination form a 6 member fused saturated azacyclic ring optionally substituted with benzyl or 5, 6, 9 or 10 member heteroarylmethyl, which heteroaryl has 1 or 2 rings and 1 or 2 ring heteroatoms independently selected from N, O and S;

R⁵ and R⁵ᵃ are independently selected from the group consisting of hydrogen and C₁-C₄alkyl; or R⁵ and R⁵ᵃ, taken in combination form a spirocyclic cyclopropyl ring; and R⁶ and R⁶ᵃ are independently selected from the group consisting of hydrogen and C₁-C₄alkyl; or R⁶ and R⁶ᵃ, taken in combination form a spirocyclic cyclopropyl ring.

3. The compound of claim 2, or a pharmaceutically acceptable salt thereof, wherein Z is O.

4. The compound of claim 2, or a pharmaceutically acceptable salt thereof, wherein R² is N-substituted piperidin-4-yl wherein the N-substituent is haloC₁-C₄alkyl, C(O)cyclopropyl, S(O)₂cyclopropyl, S(O)₂C₁-C₄alkyl, C(O)cyclobutyl, C(O)N(C₁-C₄alkyl)₂, C(O)C₁-C₄alkyl, C(O)C₁-C₄alkoxy or C(O)C₁-C₄alkyl substituted with hydroxyl or amino.

5. The compound of claim 2, or a pharmaceutically acceptable salt thereof, wherein R² is N-substituted piperidin-4-yl wherein the N-substituent is 2,2,2-trifluoroethyl, C(O)cyclopropyl, C(O)(1-hydroxyethyl), S(O)₂ethyl, S(O)₂cyclopropyl, C(O)ethyl, C(O)iso-propyl, C(O)N(methyl)₂ or C(O)N(ethyl)₂.

6. The compound of claim 2, or a pharmaceutically acceptable salt thereof, wherein R¹ is methyl and R³ and R⁴ are hydrogen.

7. The compound of claim 2, or a pharmaceutically acceptable salt thereof, wherein R¹ and R⁴ are hydrogen; and R³ is ethyl.

8. The compound of claim 2, wherein R⁵ is methyl and R⁵ᵃ, R⁶ and R⁶ᵃ are hydrogen; or R⁶ is methyl and R⁵, R⁵ᵃ and R⁶ᵃ are hydrogen.

9. The compound of claim 2, wherein R⁵ and R⁵ᵃ are methyl, or R⁵ and R⁵ᵃ, taken in combination form a spirocyclic cyclopropyl ring; and R⁶ and R⁶ᵃ are hydrogen.

10. The compound of claim 2, wherein R is methyl or ethyl.

11. The compound of claim 2, wherein R is trifluoromethyl.

12. The compound of claim 2, wherein X is N.

13. A pharmaceutical composition comprising a compound of claim 2, or a salt thereof, and a pharmaceutically acceptable excipient.

14. A method of treating glaucoma and controlling intraocular pressure comprising: applying a therapeutically effective amount of a pharmaceutical composition comprising a compound of claim 2, or a pharmaceutically acceptable salt thereof to an affected eye of a patient in need of said treatment.

15. A compound according to claim 1 which is 1-(6-(2-((4-(1-(cyclopropanecarbonyl)piperidin-4-yl)-3-ethylphenoxy)methyl)-3-methylcyclohex-1-en-1-yl)pyridin-2-yl)-5-methyl-1H-pyrazole-4-carboxy c acid having the following formula:

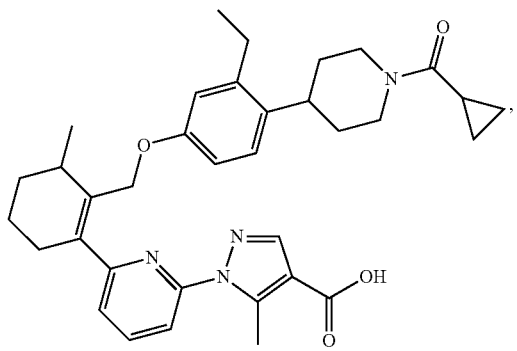 [SMILES: CCc1cc(OCC2=C(c3cccc(-n4ncc(C(=O)O)c4C)n3)CCCC2C)ccc1C1CCN(C(=O)C2CC2)CC1]

or a pharmaceutically acceptable salt thereof.

16. A compound according to claim 1 which is 1-(6-(2-((4-(1-(Cyclopropanecarbonyl)piperidin-4-yl)-3-ethylphenoxy)methyl)-3-methylcyclohex-1-en-1-yl)pyridin-2-yl)-5-ethyl-1H-pyrazole-4-carboxylic acid having the following formula:

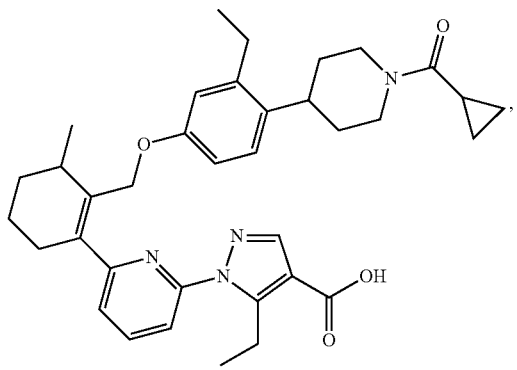 [SMILES: CCc1cc(OCC2=C(c3cccc(-n4ncc(C(=O)O)c4CC)n3)CCCC2C)ccc1C1CCN(C(=O)C2CC2)CC1]

or a pharmaceutically acceptable salt thereof.

17. A compound according to claim 1 which is 1-(6-(2-((4-(1-(cyclopropanecarbonyl)piperidin-4-yl)-2-methylphenoxy)methyl)-3-methylcyclohex-1-en-1-yl)pyridin-2-yl)-5-(trifluoromethyl)-1H-pyrazole-4-carboxylic acid having the following formula:

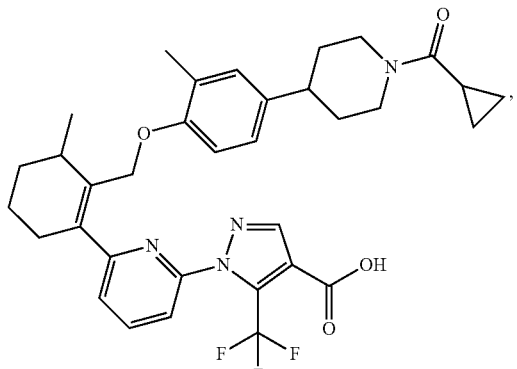

or a pharmaceutically acceptable salt thereof.

* * * * *